United States Patent [19]

Shimizu et al.

[11] Patent Number: 5,730,901
[45] Date of Patent: Mar. 24, 1998

[54] SILACYCLOHEXANE COMPOUNDS, PREPARATION THEREOF LIQUID CRYSTAL COMPOSITIONS COMPRISING THE SAME, AND LIQUID CRYSTAL DEVICES COMPRISING THE COMPOSITION

[75] Inventors: Takaaki Shimizu; Tsutomu Ogihara; Tatsushi Kaneko; Takanobu Takeda; Koji Hasegawa, all of Niigata-ken, Japan

[73] Assignee: Shin-Etsu Chemical Co., Ltd., Tokyo, Japan

[21] Appl. No.: 644,775

[22] Filed: May 10, 1996

[30] Foreign Application Priority Data

May 11, 1995 [JP] Japan .................. 7-137330

[51] Int. Cl.$^6$ ............ C09K 19/52; G02F 1/13; C07F 7/08
[52] U.S. Cl. ............ 252/299.61; 252/299.63; 349/182; 556/406
[58] Field of Search ............ 252/299.01, 299.63, 252/299.61; 556/406; 349/182

[56] References Cited

U.S. PATENT DOCUMENTS

| | | | |
|---|---|---|---|
| 5,454,977 | 10/1995 | Shimizu et al. | 252/299.61 |
| 5,496,501 | 3/1996 | Shimizu et al. | 252/299.61 |
| 5,498,737 | 3/1996 | Ogihara et al. | 556/406 |
| 5,514,824 | 5/1996 | Kinsho et al. | 556/406 |
| 5,519,156 | 5/1996 | Kinsho et al. | 556/406 |
| 5,523,439 | 6/1996 | Ogihara et al. | 556/406 |
| 5,523,440 | 6/1996 | Nakashima et al. | 556/406 |
| 5,527,490 | 6/1996 | Kinsho et al. | 252/299.61 |
| 5,543,539 | 8/1996 | Shimizu et al. | 556/406 |
| 5,560,866 | 10/1996 | Ogihara et al. | 252/299.61 |
| 5,582,765 | 12/1996 | Kinsho et al. | 252/299.61 |

FOREIGN PATENT DOCUMENTS

| | | |
|---|---|---|
| 1175947 | 7/1989 | Japan . |
| 4226589 | 8/1992 | Japan . |
| 4504880 | 8/1992 | Japan . |
| 4505477 | 9/1992 | Japan . |
| 5500680 | 2/1993 | Japan . |
| 5500681 | 2/1993 | Japan . |
| 5500682 | 2/1993 | Japan . |
| 6501520 | 3/1993 | Japan . |
| 5331464 | 12/1993 | Japan . |
| 6500343 | 1/1994 | Japan . |

Primary Examiner—Shean C. Wu
Attorney, Agent, or Firm—Lowe, Price, LeBlanc & Becker

[57] ABSTRACT

A silacyclohexane compound of the formulas (I)

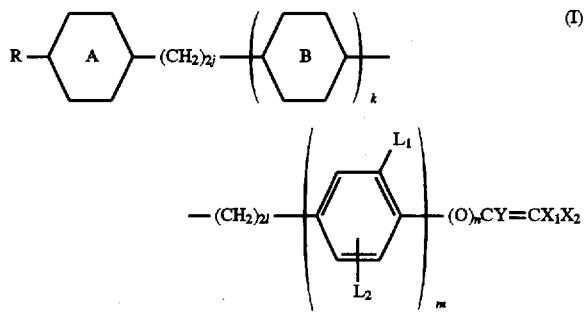

wherein R represents an organic residue,

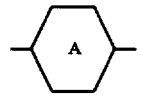

represents an unsubstituted or substituted silicon-containing cyclohexylene group or a 1,4-cyclohexylene group,

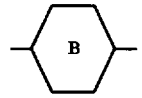

represents an unsubstituted or substituted phenylene, an unsubstituted or substituted silicon-containing cyclohexylene group or trans-4-sila-1,4-cyclohexylene group, or a 1,4-cyclohexylene group provided that at least one of these residues represents a silicon-containing cyclohexylene group, m, n, i, k and l are, respectively, 0 or 1 provided that j+l=0 or 1 and m+k=1 or 2, $L_1$ and $L_2$, respectively, represent H or F, m and n are, respectively, 0 or 1, $X_1$ and Y independently represent H, F or Cl, and $X_2$ represents F or Cl. A liquid crystal composition comprising the silacyclohexane compound of the above formula is also described, along with a liquid crystal device comprising the composition.

26 Claims, No Drawings

SILACYCLOHEXANE COMPOUNDS, PREPARATION THEREOF LIQUID CRYSTAL COMPOSITIONS COMPRISING THE SAME, AND LIQUID CRYSTAL DEVICES COMPRISING THE COMPOSITION

BACKGROUND OF THE INVENTION

1. Field of the Invention

This invention relates to novel silacyclohexane compounds. The invention also relates to liquid crystal compositions comprising the silacyclohexane compound or compounds, and to devices comprising the compositions.

2. Description of the Prior Art

The liquid crystal display devices utilize optical and dielectric anisotropies of liquid crystal substances. Depending on the mode of display, different types of display systems are known including those of a twisted nematic type (TN type), a supertwisted nematic type (STN type), a super birefringence type (SBE type), a dynamic scattering type (DS type), a guest/host type, a type of deformation of aligned phase (DAP type), and an optical mode interference type (OMI type). The most popular display device is one which is based on the Schadt-Helfrich effect and has a twisted nematic structure.

Although the properties of the liquid crystal substances used in these liquid crystal devices depend, more or less, on the type of display, it is commonly required that the liquid crystal substances have a wide range of temperatures working as a liquid crystal and that they be stable against moisture, air, light, heat, electric field and the like. Moreover, the liquid crystal substances should desirably be low in viscosity and should ensure a short address time, a low threshold voltage and a high contrast in cells.

At present, liquid substances which can satisfy all the requirements have never been known when used singly. In practice, several to ten and several liquid compounds and/or latent liquid crystal compounds are used in the form of mixtures. To this end, it is important that constituent components be readily compatible with one another.

Among the various types of display modes, the twisted nematic mode which is driven with an active matrix (AM) using a TFT (thin film transistor) element array or an MIM (metal insulator metal) element array has now been in extensive use owing to its high image display qualifies including high definition, high contrast and high response speed. This is because the DRAM making techniques in the industry of silicon semiconductors have been applied to and developed in the liquid crystal panel making techniques, thus leading to reduction of costs and promoting the advancement of the techniques.

The nematic liquid crystal substances employed in the active matrix liquid crystal devices (AM-LCD) should have not only the above-mentioned properties, but also a signal voltage retention characteristic which is essentially required for the drive system of the devices. This signal voltage retention characteristic indicates a degree of lowering of the signal voltage applied to TFT pixels including a liquid crystal within a given frame period. Accordingly, when the signal voltage does not drop at all wherein the voltage retention rate is 100%, the liquid crystal molecules are kept as they are in arrangement and any lowering of contrast does not take place. The voltage holding characteristic is, more or less, influenced by the environment in which the liquid crystal is used. More particularly, in environments where the liquid crystal is exposed to light of high intensity such as in liquid crystal panel projectors, or where it is exposed to high temperatures such as in on-vehicle liquid crystal panels, the life characteristic is liable to be shortened.

In order to attain a low drive voltage, i.e. a low threshold voltage of a liquid crystal composition, it will be sufficient to increase a dielectric anisotropy ($\Delta\epsilon$) of the liquid crystal composition. From this point of view, compositions of liquid crystal compounds which have a positive value of dielectric anisotropy ($\Delta\epsilon$) and core structures constituted of a cyclohexane ring or rings and a benzene ring or rings have been proposed for use in AM-LCD, for example, in Japanese Laid-open Patent Application Nos. 4-226589, 4-505477, 4-504880, 5-331464, 5-500680, 5-500681, 5-500682 and 6-501520.

Liquid crystal compounds which contain a haloolefin group as a polar group are known, including those compounds shown below:

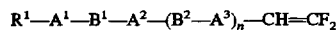

wherein $R^1$ represents a $C_1$ to $C_{20}$ alkyl or alkenyl group which may contains O in the chain, $A^1$, $A^2$ and $A^3$ independently represents

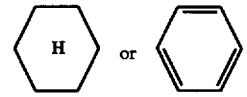

wherein the phenyl group may be unsubstituted or substituted with F, Cl or methyl, $B^1$ and $B^2$ independently represent —$CH_2CH_2$—, —$CH_2O$—, —$OCH_2$— or single bond, and n is 0 or 1 as proposed in Japanese Laid-open Patent Application No. 1-175947; and

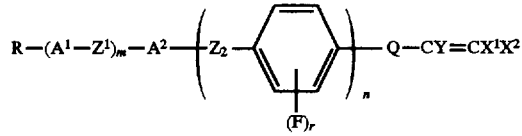

wherein R represents H or a $C_1$ to $C_{15}$ alkyl or alkenyl group which may be unsubstituted or substituted with CN, $CF_3$ or a halogen, $A^1$ or $A^2$ independently represent a trans-1,4-cyclohexylene group wherein one or more of non-adjacent $CH_2$ group may be substituted with —O— and/or —S—, a 1,4-phenylene group wherein one or two CH groups may be substituted with N, or a group selected from 1,4-cyclohexenylene, 1,4-bicyclo(2,2,2)octylene, pyperidin-1,4-diyl, naphthalen-2,6-diyl, decahydronapthalen-2,6-diyl and 1,2,3,4-tetrahydronaphthalen-2,6-diyl, $Z^1$ and $Z^2$ independently represent —CO—O—, —O—CO—, —$CH_2O$—, —$OCH_2$—, —$CH_2CH_2$—, —CH=CH—, —C≡C— or single bond, Q represents —O—, —$CH_2CH_2$—, —C≡C—, trans —CH=CH—, —COO— or —$CH_2O$—, $X^1$ represents H, F or Cl, $X^2$ F, Cl, $CF_3$, $OCF_3$, $OCHF_2$ or $SF_5$, m is 0, 1, 2 or 3, or n is 0 or 1, r is 0, 1, 2, 3, or 4 as set out in Japanese Laid-open Patent Application No. 6-500343.

As liquid crystal display devices have now wider utility in various fields, the characteristic properties required for liquid crystal materials become severer. Especially, with portable liquid crystal devices whose electric power is based on batteries, reduced consumption power is essential. To this end, it is beneficial to lower a drive voltage of liquid crystal devices. The increase in dielectric anisotropy ($\Delta\epsilon$) of liquid crystal materials enables one to permit lower voltage drive. However, the liquid crystal materials whose dielectric anisotropy is great are deficient in that their nematic-isotropic transition temperatures ($T_{NI}$) are commonly low.

SUMMARY OF THE INVENTION

It is accordingly an object of the invention to provide hitherto unknown compounds which have an Si-containing silacyclohexane ring structure in the molecule, and which serve as a liquid crystal substance as having a relatively high dielectric anisotropy, ($\Delta\epsilon$), and a high nematic-isotropic transition temperature, $T_{NI}$, along with a high voltage retention rate under severe environmental conditions.

It is another object of the invention to provide novel compounds which exhibit a nematic liquid crystal phase over a wide temperature range, a low viscosity, a high speed response and good miscibility with one another and also with other types of liquid crystal compounds.

It is a further object of the invention to provide novel liquid crystal compounds which are stable against moisture, air, heat and electric field.

It is a still further object of the invention to provide a liquid crystal composition which comprise at least a compound of the type as set out above.

It is another object of the invention to provide a liquid crystal display device comprising the composition.

The above objects can be achieved, according to one embodiment of the invention, by a silacyclohexane compound of the formula (I)

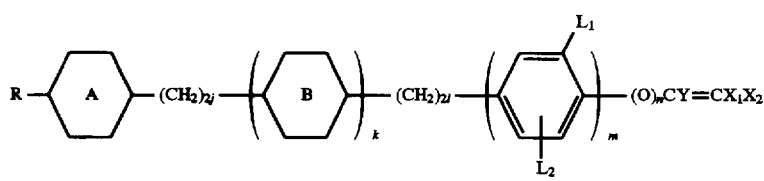

wherein R represents a linear alkyl group having from 1 to 10 carbon atoms, a branched alkyl group having from 3 to 8 carbon atoms, an alkoxyalkyl group having from 2 to 7 carbon atoms, an alkenyl group having from 2 to 8 carbon atoms, or a mono or difluoroalkyl group having from 1 to 10 carbon atoms;

represents a trans-1-sila-1,4-cyclohexylene group or a trans-4-sila-1,4-cyclohexylene group wherein the silicon atom at the 1 or 4 position has H, F, Cl or $CH_3$, or a 1,4-cyclohexylene group,

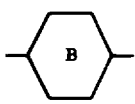

represents an unsubstituted or substituted phenylene group having, if substituted, one or two fluorine atoms, a trans-1-sila-1,4-cyclohexylene group or a trans-4-sila-1,4-cyclohexylene group wherein the silicon atom at the 1 or 4 position has H, F, Cl or $CH_3$, or a 1,4-cyclohexylene group provided that at least one of

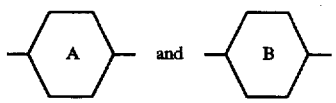

represents a trans-1-sila-1,4-cyclohexylene group or a trans-4-sila-1,4-cyclohexylene group wherein the silicon atom at the 1 or 4 position has H, F, Cl or $CH_3$, m, n, i, k and l are, respectively, 0 or 1 provided that j+l=0 or 1 and m+k=1 or 2, $L_1$ and $L_2$, respectively, represent H or F, m and n are, respectively, 0 or 1, $X_1$ and Y independently represent H, F or Cl, and $X_2$ represents F or Cl.

According to another embodiment of the invention, there is also provided a liquid crystal composition which comprises the liquid crystal compound of the formula (I) defined above. As will be apparent from the definition of the formula (I), the compound of the formula (I) may have a two-ring structure wherein m+k=1. Alternatively, the compound may have a three-ring structure wherein m+k=2. In view of the temperature range working as a liquid crystal phase when applied as a liquid crystal composition, the compounds having the three-ring structure are preferred and specific formulas of these compounds will be particularly described hereinafter. In the sense, it is preferred that the liquid crystal composition comprises at least one compound of the formula (I) which has a three-ring structure. The compounds of the formula (I) having three-ring structures may be used as they are or in combination with other types of known liquid crystal compounds. If the compounds of the formula (I) having three-ring structures are used in combination with other types of liquid crystal compounds, it is preferred to use at least one member selected from other types of compounds having three-ring structures of the following formulas (III) to (VI)

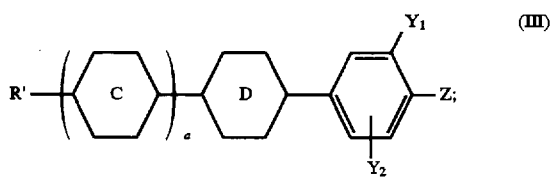

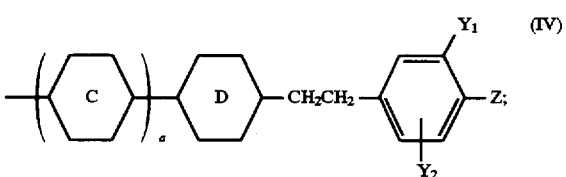

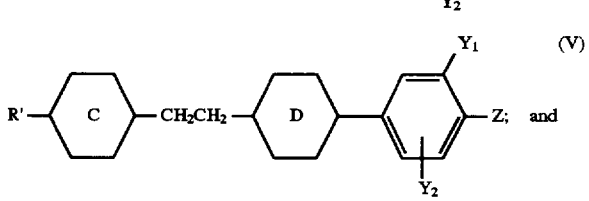

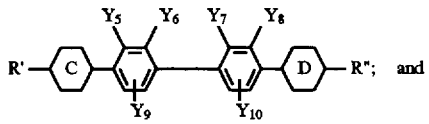

(VII)

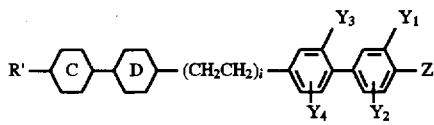

(VIII)

wherein R' and Z are, respectively, as defined in the forgoing formulas,

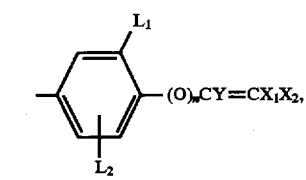

are respectively, as defined in the formulas (II) to (VI), R" has the same meaning as R', $Y_1$ to $Y_4$ are, respectively, as defined above, $Y_5$ to $Y_{10}$ are, respectively, H or F like $Y_1$ to $Y_4$, and i is 0 or 1.

The invention further provides a liquid crystal display device which comprises at least one of the liquid crystal compositions defined above.

The liquid crystal composition of the invention exhibits a nematic liquid crystal phase over a wide working temperature range and has a low viscosity, high response speed, good miscibility with one another or other types of liquid crystal compounds, and good stability against moisture, air, light, heat and electric field. Especially, when using the compounds of the invention have a polar group of the following formula

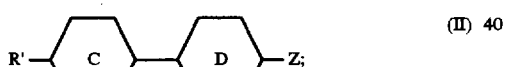

the resultant liquid crystal compositions exhibit a nematic-isotropic phase temperatures which is as high as 80° C. or over. The compounds of the invention having a silacyclohexane ring or rings are advantageous in their low threshold voltage, high voltage holding rate under severe conditions, and good nematic phase stability at low temperatures while preventing formation of a smectic or crystal phase.

DETAILED DESCRIPTION OF THE INVENTION

The novel compounds of the invention serving as a liquid crystal substance are those of the formula (I) defined hereinbefore.

Specific examples of the compound of the formula (I) include those compounds of the formulas ($I_1$) to ($I_{30}$) which have, respectively, novel ring structures containing a trans-1- or trans-4-silacyclohexane ring

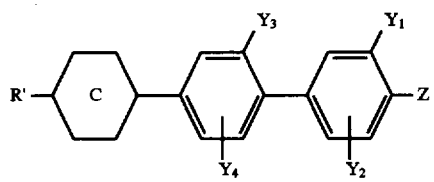

(VI)

wherein each R' represents an alkyl group having from 1 to 7 carbon atoms, an alkoxyalkyl group having from 2 to 7 carbon atoms, a mono or difluoroalkyl group having from 2 to 7 carbon atoms, or an alkenyl group having from 2 to 8 carbon atoms,

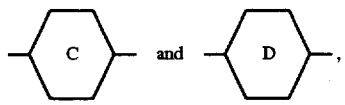

respectively, represent a trans-1-sila-1,4-cyclohexylene group, a trans-4-sila-1,4-cyclohexylene group or a trans-1,4-cyclohexylene group, Z represents F, Cl, $OCHF_2$, $OCF_3$, $O(CH_2)_p(CF_2)_qM$ in which p and q are, respectively, 0, 1 or 2 provided that p+q are 2, 3 or 4, and M is H, F or Cl, or $(O)_nCY=CX_1X_2$ in which n, Y, $X_1$ and $X_2$ are, respectively, as defined in the formula (I), $Y_1$, $Y_2$, $Y_3$ and $Y_4$, respectively, represent H or F, and a is 0 or 1. In the above formulas (III) and (IV), the three-ring structure is obtained when a is 1 although compounds of the formulas (III) to (IV) having two-ring structures may also be used.

Moreover, the liquid crystal composition defined above may further comprise at least one liquid crystal compound of having a two-ring structure by which a high response speed and a low threshold voltage can be attained. The compounds having the two-ring structure may be of the formula (I) wherein m+k=1 and of the formulas (II), (III) and (IV) provided that a=0 in the formulas (III) and (IV)

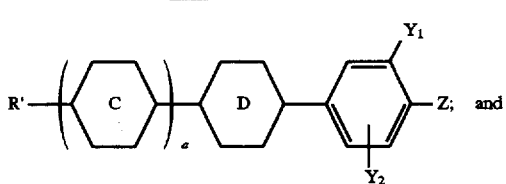

(II)

(III)

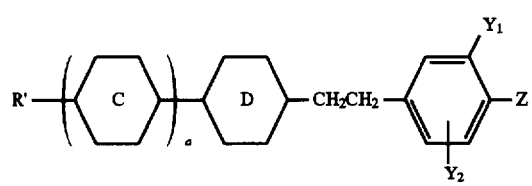

(IV)

The liquid crystal composition of the invention exhibits a nematic liquid crystal phase over a wide temperature range. In order to further extend the working temperature of the nematic liquid crystal phase to a higher level, it is preferred to further add at least one member selected from compounds of the formulas (VII) to (VIII):

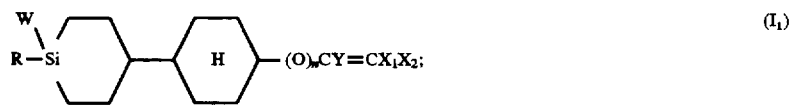 (I₁)
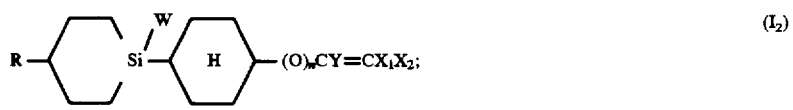 (I₂)
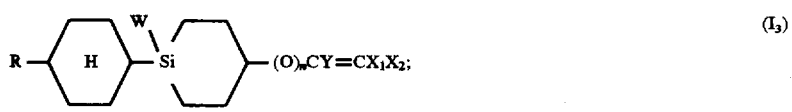 (I₃)
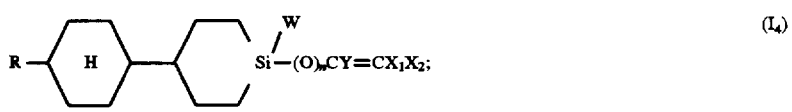 (I₄)
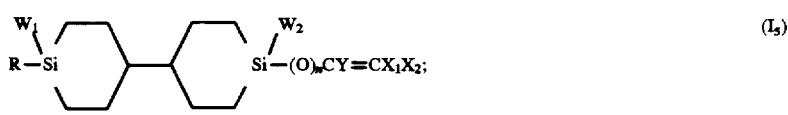 (I₅)
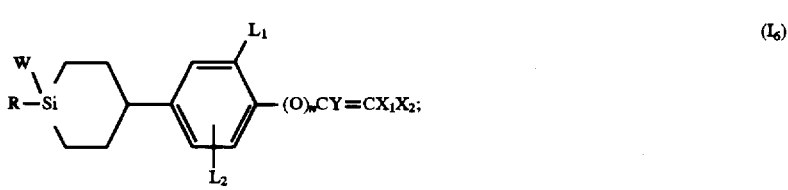 (I₆)
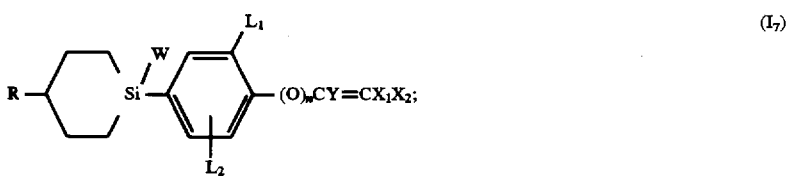 (I₇)
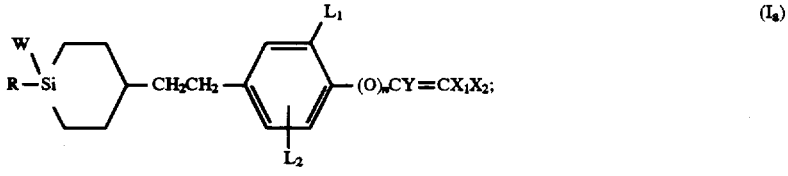 (I₈)
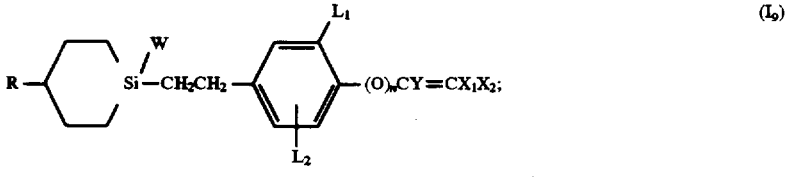 (I₉)
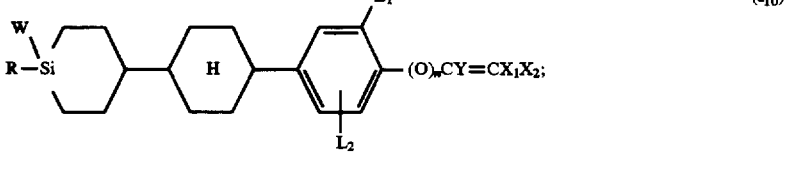 (I₁₀)
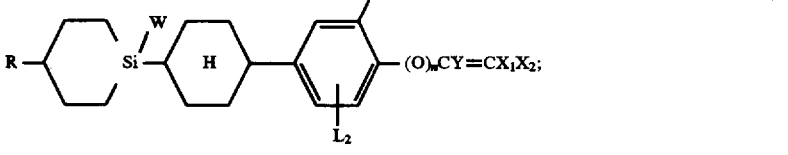 (I₁₁)

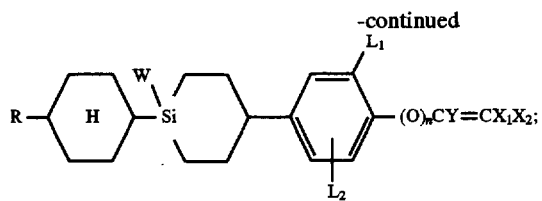 (I₁₂)
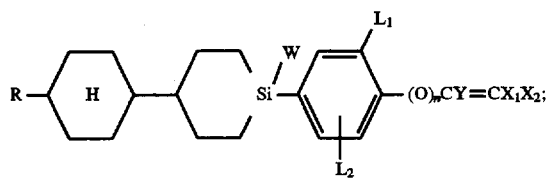 (I₁₃)
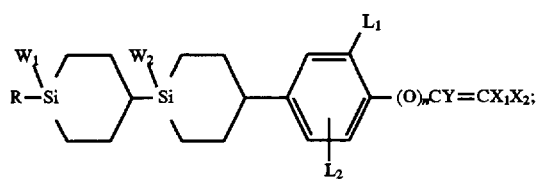 (I₁₄)
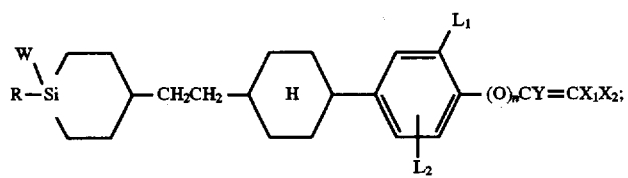 (I₁₅)
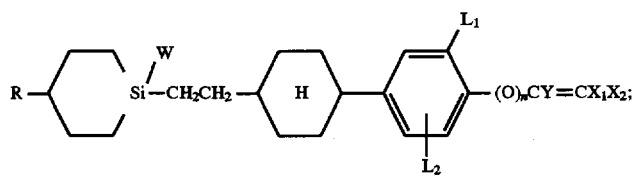 (I₁₆)
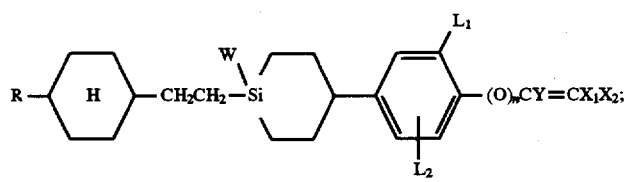 (I₁₇)
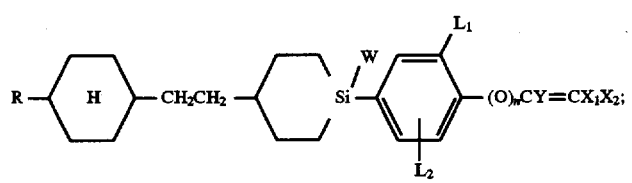 (I₁₈)
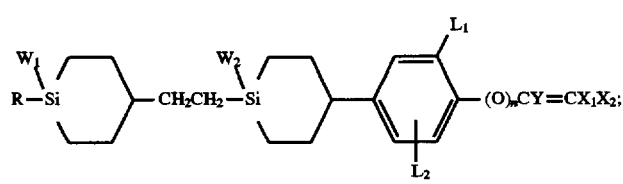 (I₁₉)
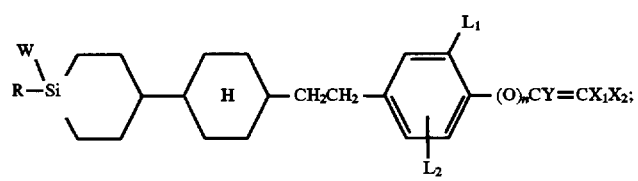 (I₂₀)

-continued
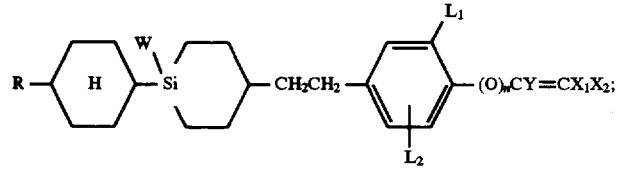 (I₂₂)
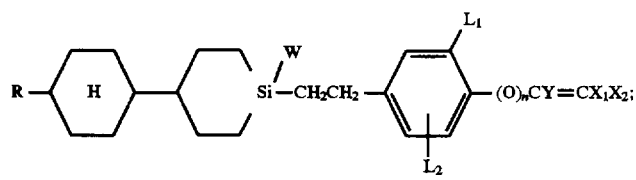 (I₂₃)
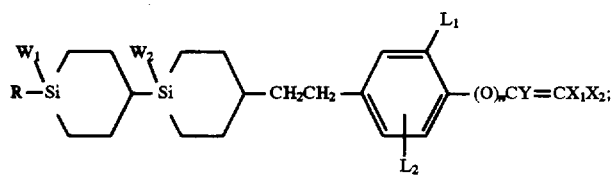 (I₂₄)
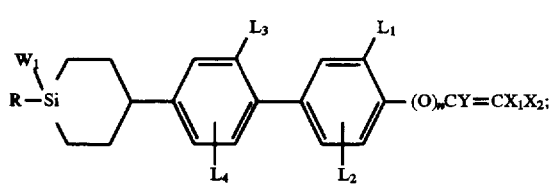 (I₂₅)
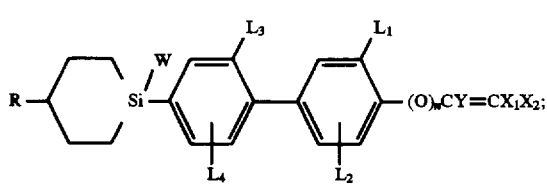 (I₂₆)
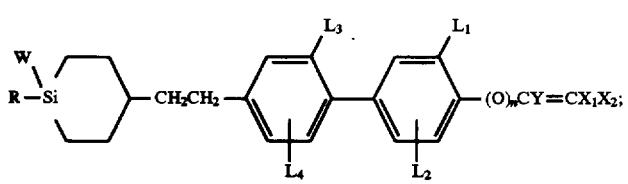 (I₂₇)
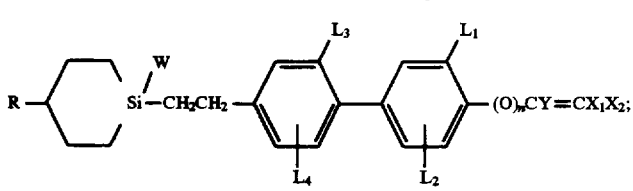 (I₂₈)
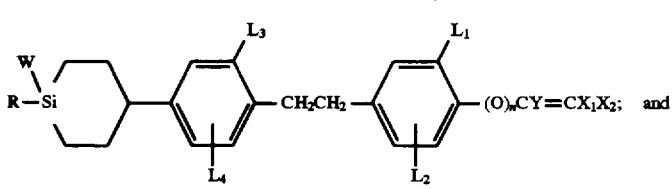 (I₂₉) and
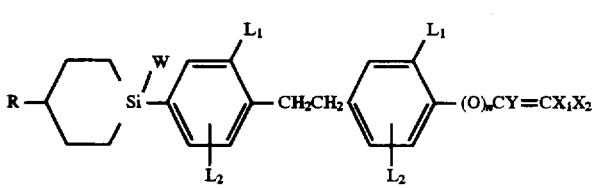 (I₃₀)

wherein R, $L_1$, $L_2$, $X_1$, $X_2$, $L_1$, $L_2$, and n are, respectively, as defined in the formula (I), W, $W_1$ and $W_2$ are, respectively, H, F, Cl or $CH_3$, and $L_3$ and $L_4$ are, respectively, H or F, like $L_1$ and $L_2$.

More particularly, in the formulas ($I_1$) to ($I_{30}$), R represents a linear alkyl group having from 1 to 10 carbon atoms, a branched alkyl group having from 3 to 8 carbon atoms, an alkoxyalkyl group having from 2 to 7 carbon atoms, an alkenyl group having from 2 to 8 carbon atoms, or a mono or difluoroalkyl group having from 1 to 10 carbon atoms.

Specific examples of the linear alkyl group include methyl, ethyl, n-propyl, n-butyl, n-pentyl, n-hexyl, n-heptyl, n-octyl, n-nonyl, and n-decyl.

Specific examples of the branched alkyl group include isopropyl, sec-butyl, isobutyl, 1-methylbutyl, 2-methylbutyl, 3-methylbutyl, 1-methylpentyl, 2-methylpentyl, 3-methylpentyl, 1-ethylpentyl, 1-methylhexyl, 2-methylhexyl, 3-methylhexyl, 2-ethylhexyl, 3-ethylhexyl, 1-methylheptyl, 2-methylheptyl, and 3-methylheptyl.

Specific examples of the alkoxyalkyl group include methoxymethyl, ethoxymethyl, propoxymethyl, butoxymethyl, pentoxymethyl, hexyloxymethyl, methoxyethyl, ethoxyethyl, propoxyethyl, butoxyethyl, methoxypropyl, ethoxypropyl, propoxypropyl, butoxypropyl, methoxybutyl, ethoxybutyl, propoxybutyl, methoxypentyl, ethoxypentyl, and methoxyhexyl.

Specific examples of the alkenyl group include vinyl, 1-propenyl, allyl, 1-butenyl, 3-butenyl, isoprenyl, 1-pentenyl, 3-pentenyl, 4-pentenyl, dimethylallyl, 1-hexenyl, 3-hexenyl, 5-hexenyl, 1-heptenyl, 3-heptenyl, 6-heptenyl, and 7-octenyl.

Specific examples of the mono or difluoroalkyl group include fluoromethyl, 1-fluoroethyl, 1-fluoropropyl, 1-fluorobutyl, 1-fluoropentyl, 1-fluorohexyl, 1-fluoroheptyl, 1-fluorooctyl, 1-fluorononyl, 1-fluorodecyl, 2-fluoroethyl, 2-fluoropropyl, 2-fluorobutyl, 2-fluoropentyl, 2-fluorohexyl, 2-fluoroheptyl, 2-fluorooctyl, 2-fluorononyl, 2-fluorodecyl, 3-fluoropropyl, 3-fluorobutyl, 3-fluoropentyl, 3-fluorohexyl, 3-fluoroheptyl, 3-fluorooctyl, 3-fluorononyl, 3-fluorodecyl, 4-fluorobutyl, 4-fluoropentyl, 4-fluorohexyl, 4-fluoroheptyl, 4-fluorooctyl, 4-fluorononyl, 4-fluorodecyl, 5-fluoropentyl, 5-fluorohexyl, 5-fluoroheptyl, 5-fluorooctyl, 5-fluorononyl, 5-fluorodecyl, 6-fluorohexyl, 6-fluoroheptyl, 6-fluorooctyl, 6-fluorononyl, 6-fluorodecyl, 7-fluoroheptyl, 7-fluorooctyl, 7-fluorononyl, 7-fluorodecyl, 8-fluorooctyl, 8-fluorononyl, 8-fluorodecyl, 9-fluorononyl, 9-fluorodecyl, 10-fluorodecyl, difluoromethyl, 1,1-difluoroethyl, 1,1-difluoropropyl, 1,1-difluorobutyl, 1,1-difluoropentyl, 1,1-difluorohexyl, 1,1-difluoroheptyl, 1,1-difluorooctyl, 1,1-difluorononyl, 1,1-difluorodecyl, 2,2-difluoroethyl, 2,2-difluoropropyl, 2,2-difluorobutyl, 2,2-difluoropentyl, 2,2-difluorohexyl, 2,2-difluoroheptyl, 2,2-difluorooctyl, 2,2-difluorononyl, 2,2-difluorodecyl, 3,3-difluoropropyl, 3,3-difluorobutyl, 3,3-difluoropentyl, 3,3-difluorohexyl, 3,3-difluoroheptyl, 3,3-difluorooctyl, 3,3-difluorononyl, 3,3-difluorodecyl, 4,4-difluorobutyl, 4,4-difluoropentyl, 4,4-difluorohexyl, 4,4-difluoroheptyl, 4,4-difluorooctyl, 4,4-difluorononyl, 4,4-difluorodecyl, 5,5-difluoropentyl, 5,5-difluorohexyl, 5,5-difluoroheptyl, 5,5-difluorooctyl, 5,5-difluorononyl, 5,5-difluorodecyl, 6,6-difluorohexyl, 6,6-difluoroheptyl, 6,6-difluorooctyl, 6,6-difluorononyl, 6,6-difluorodecyl, 7,7-difluoroheptyl, 7,7-difluorooctyl, 7,7-difluorononyl, 7,7-difluorodecyl, 8,8-difluorooctyl, 8,8-difluorononyl, 8,8-difluorodecyl, 9,9-difluorononyl, 9,9-difluorodecyl, and 10,10-difluorodecyl.

W, $W_1$ and $W_2$ are, respectively, H, F, Cl or $CH_3$, $L_1$, $L_2$, $L_3$ and $L_4$ are, respectively, H or F, $X_1$ and Y, respectively, represents H, F or Cl, $X_2$ represents F or Cl, n is 0 or 1.

Specific examples of the moiety represented by the formula $—(O)_nCY=CX_1X_2$ include $—CH=CHF$, $—CH=CF_2$, $—OCH=CF_2$, $—CF=CF_2$, $—CF=CHF$, $—OCF=CF_2$, $—CF=CHCl$, $—CF=CCl_2$, $—CCl=CHCl$, $—CH=CCl_2$ and the like.

Examples of the moiety of the formula

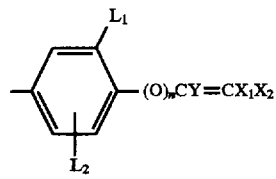

include ones mentioned below:

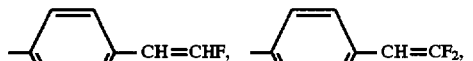
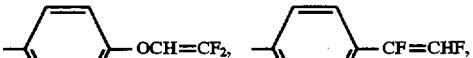
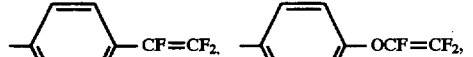
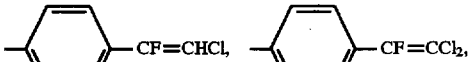
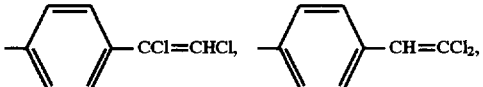
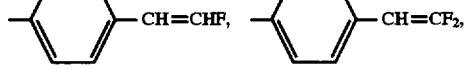
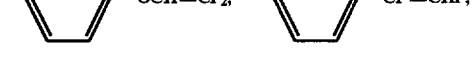
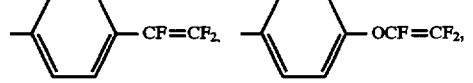
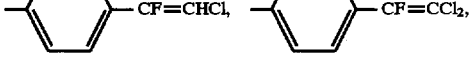
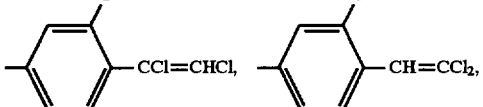

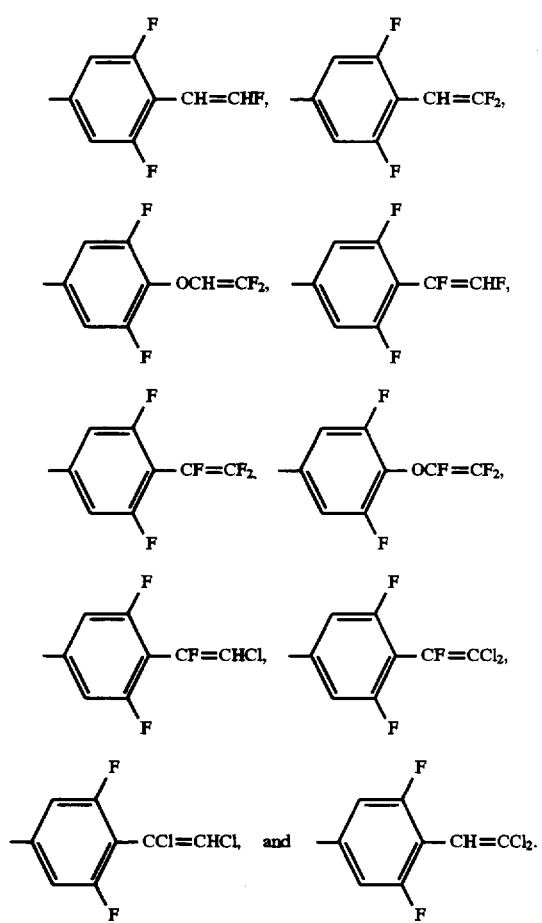
The moieties of the formula
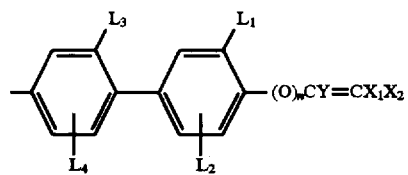
include, for example, ones shown below:
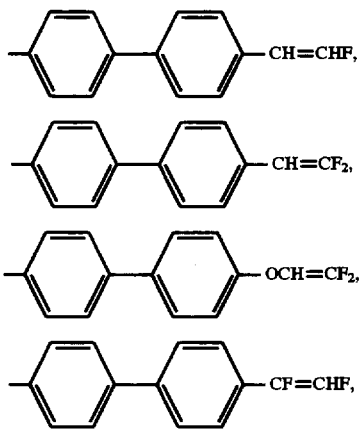
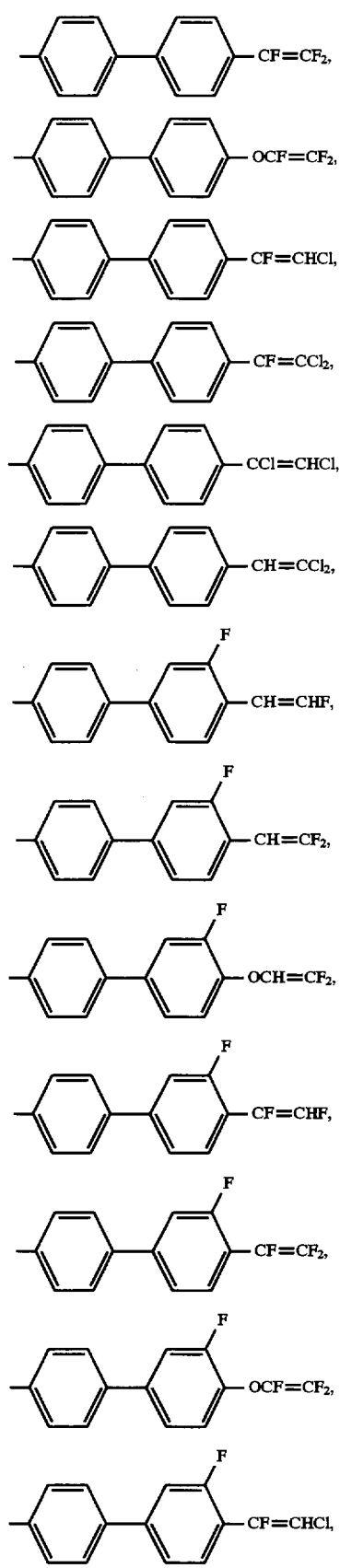

-continued
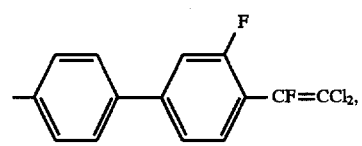
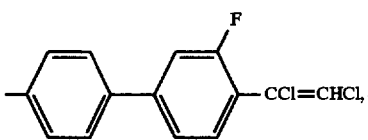
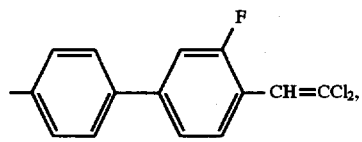
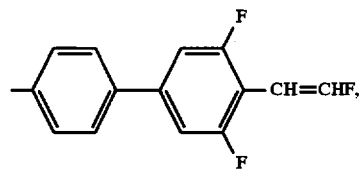
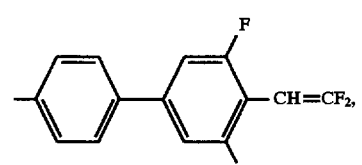
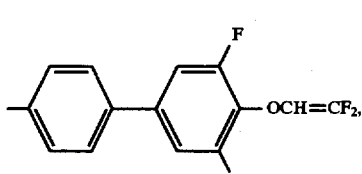
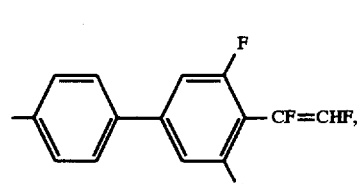
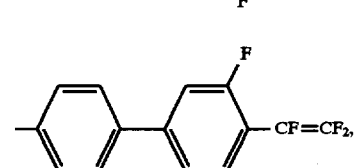
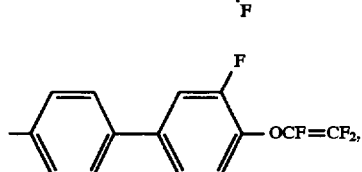
-continued
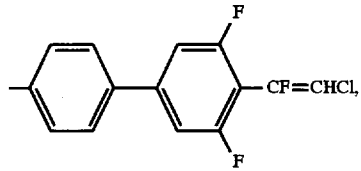
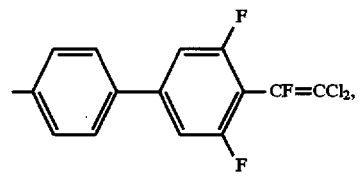
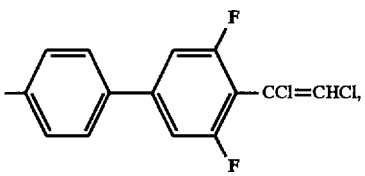
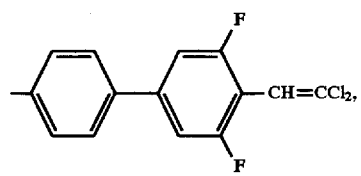
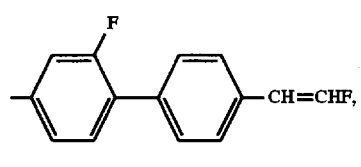
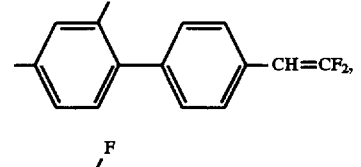
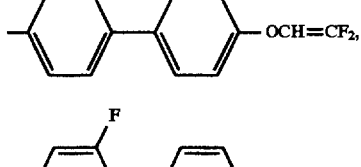
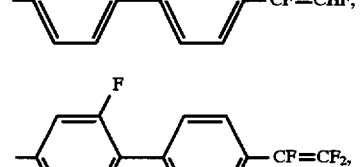
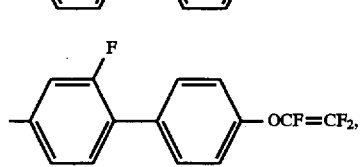

-continued
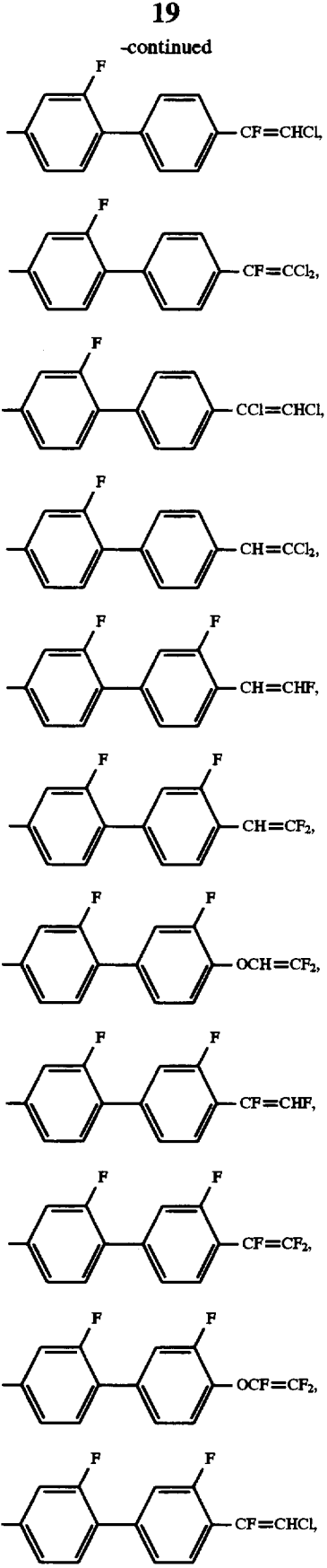
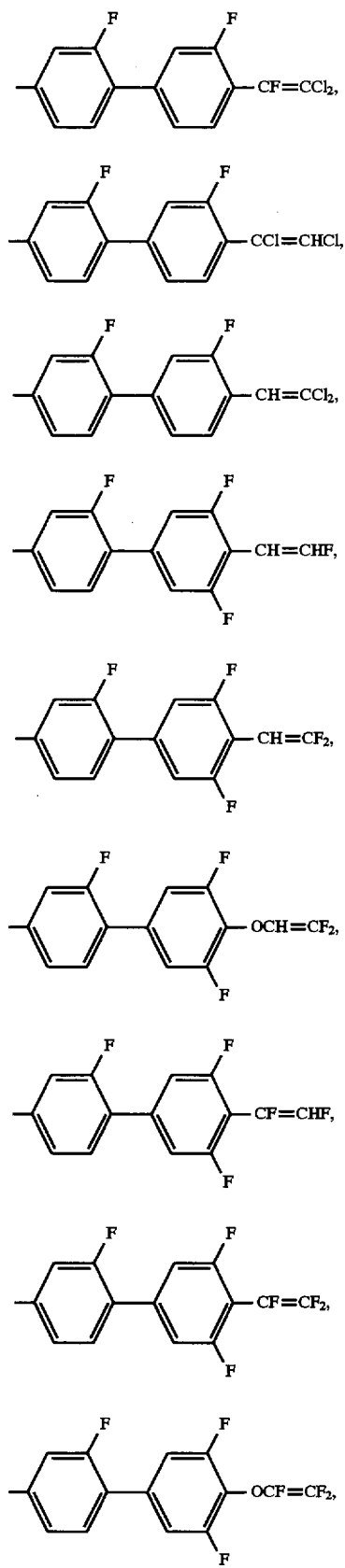

-continued
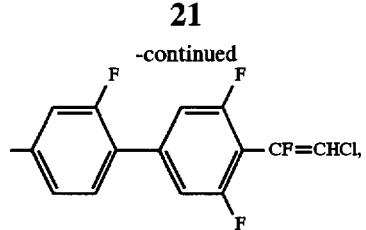
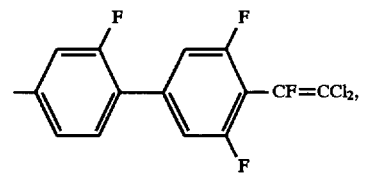
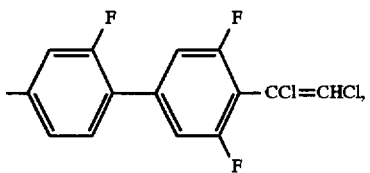
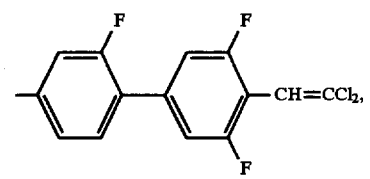
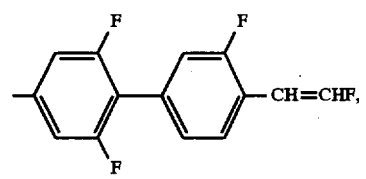
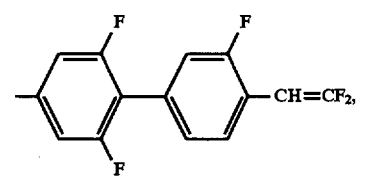
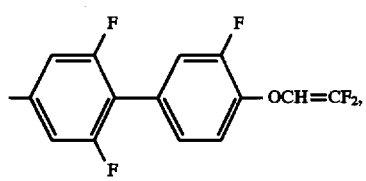
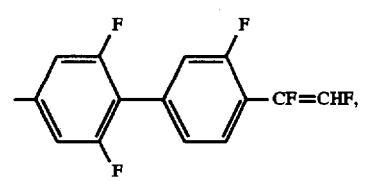
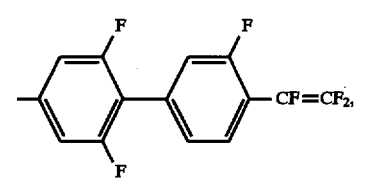
-continued
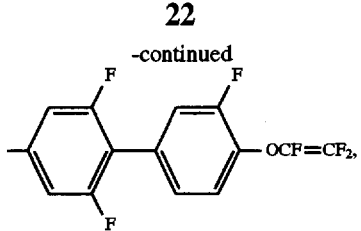
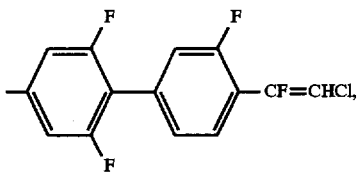
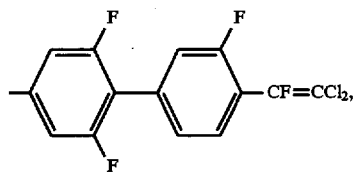
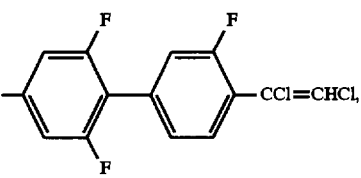
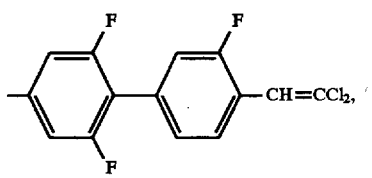
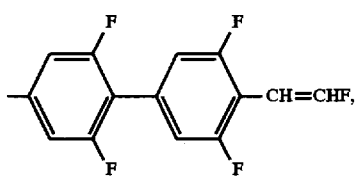
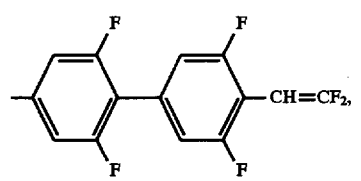
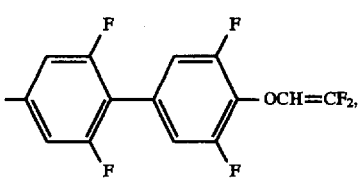
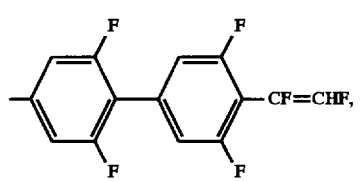

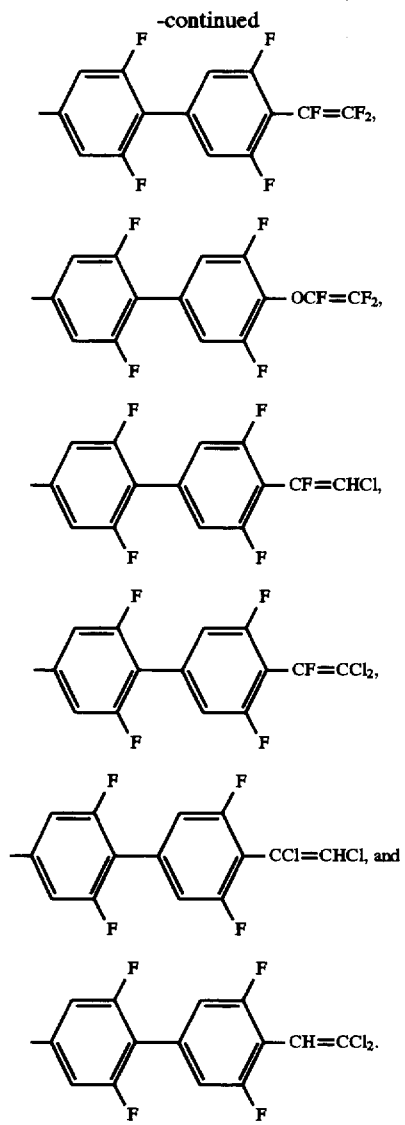
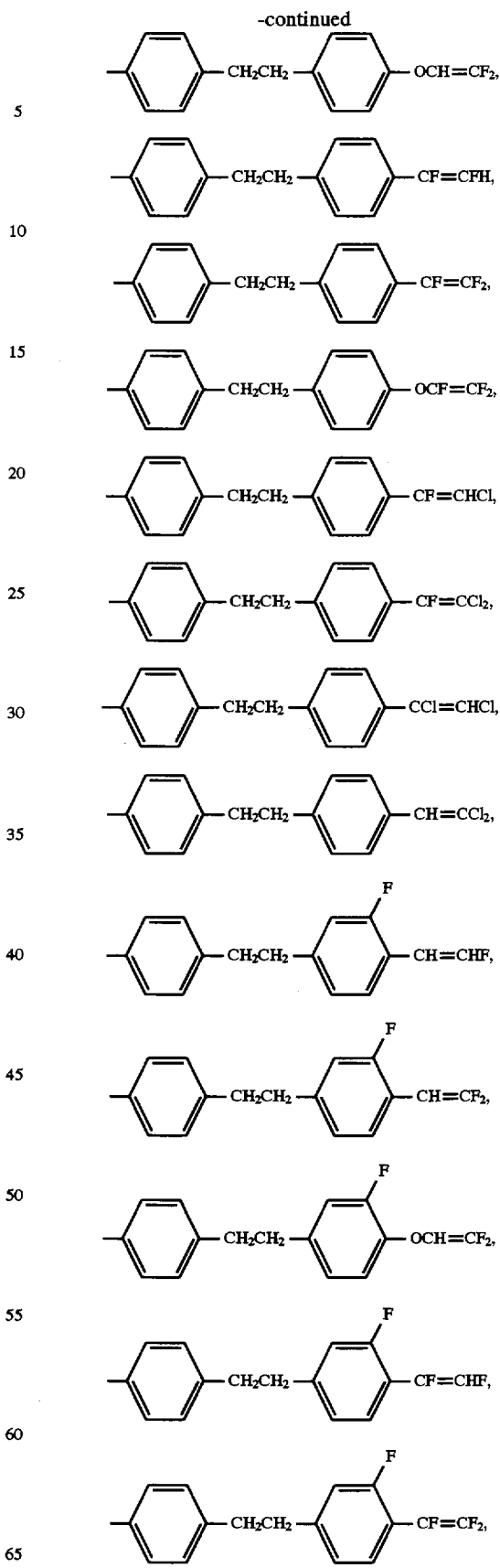
Examples of the moiety of the formula
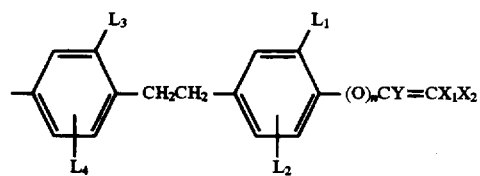
include those indicated below:
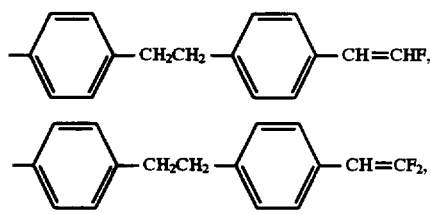

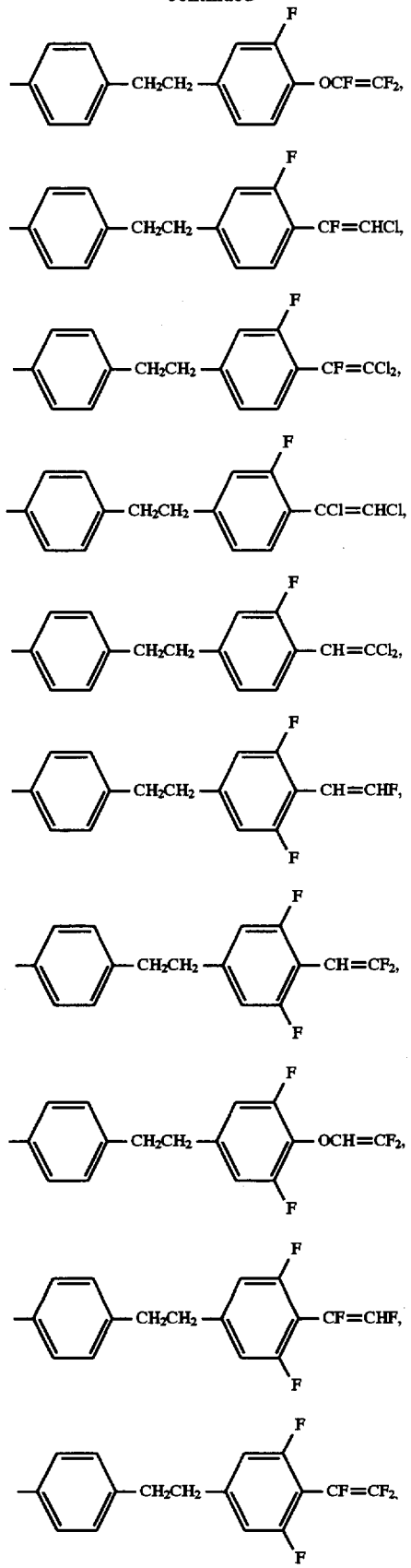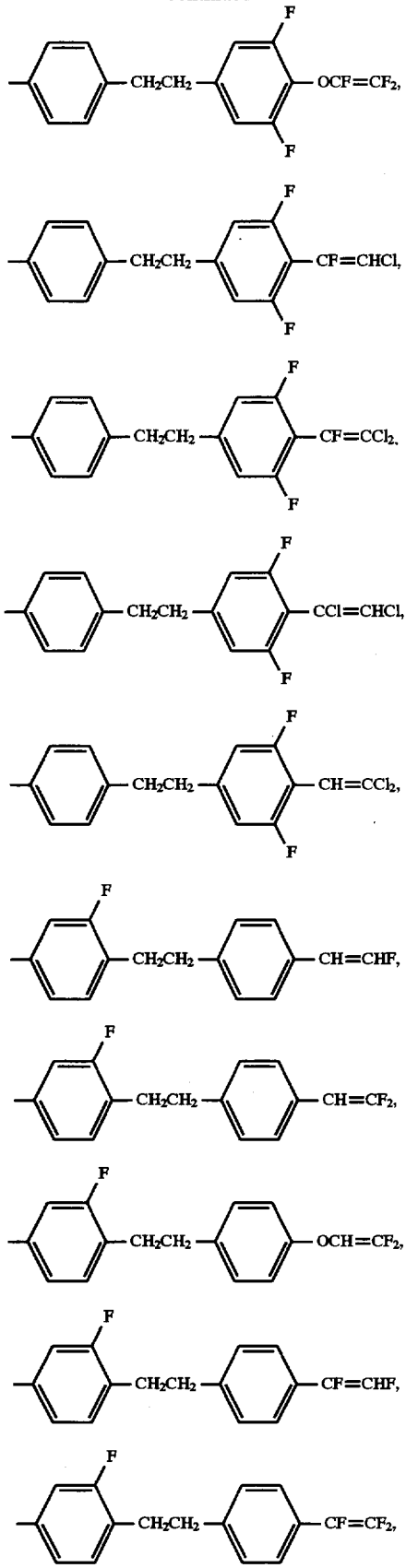

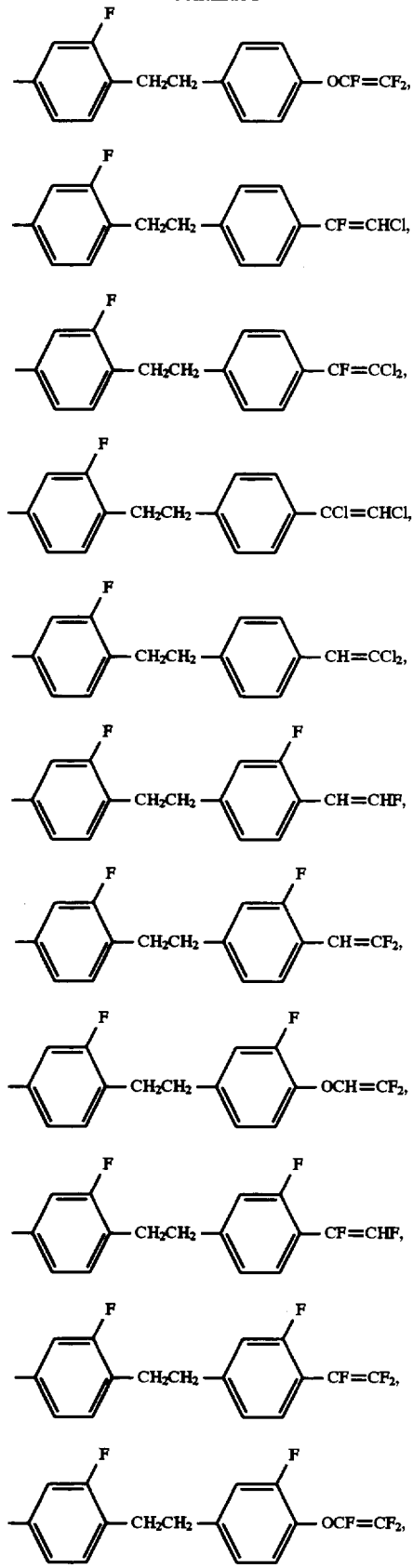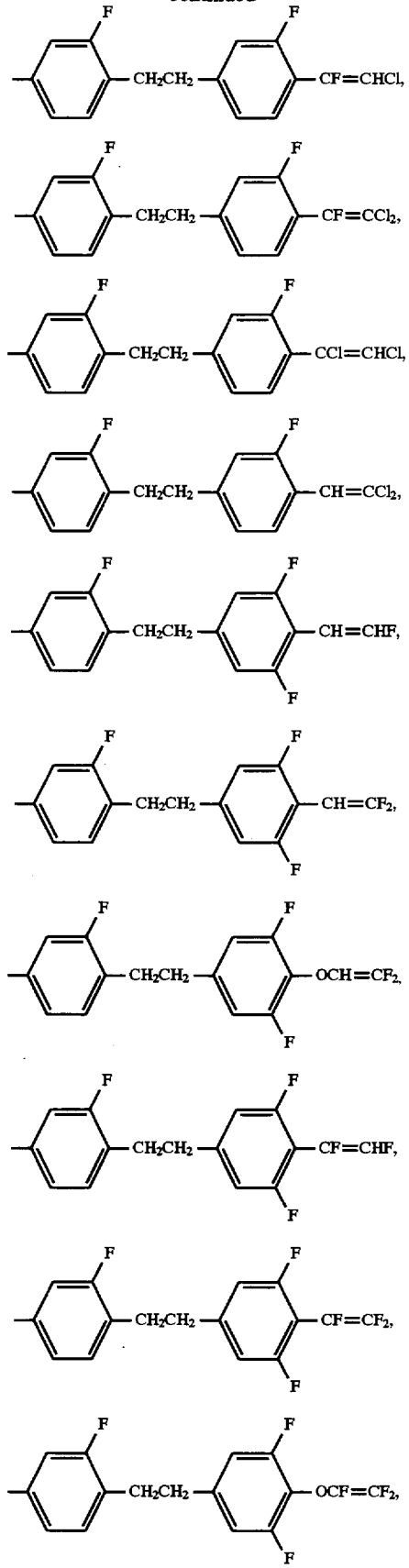

-continued
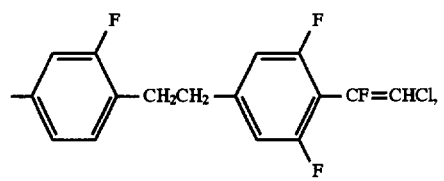
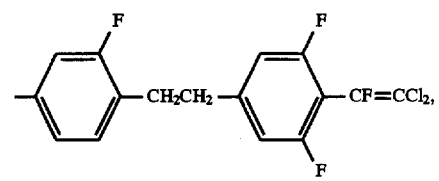
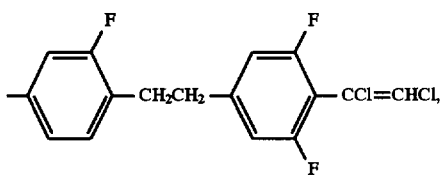
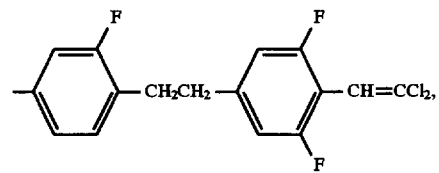
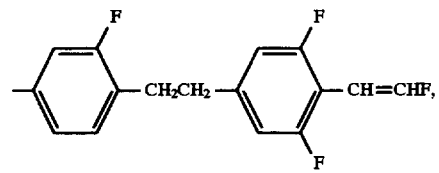
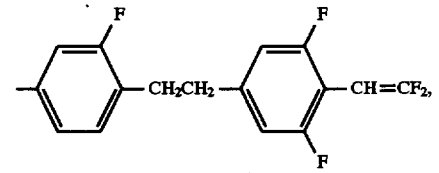
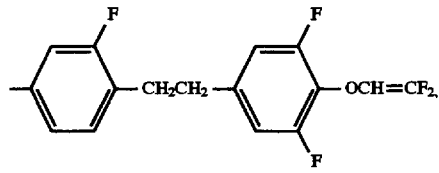
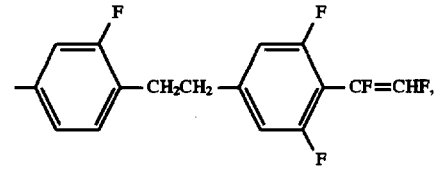
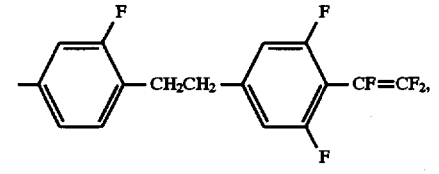
-continued
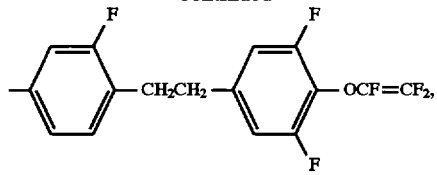
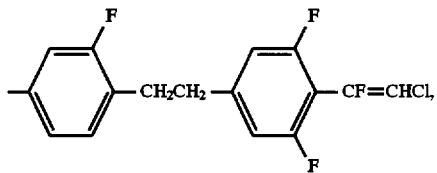
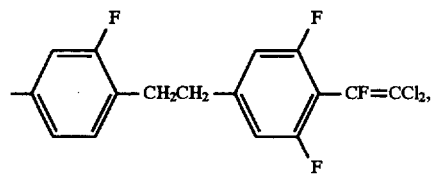
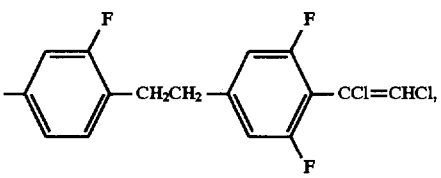
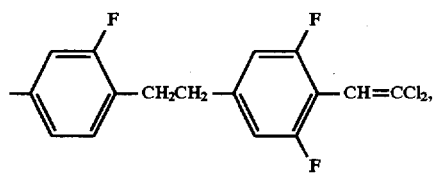
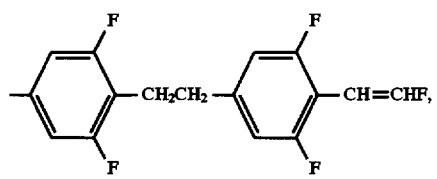
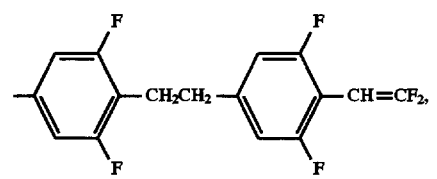
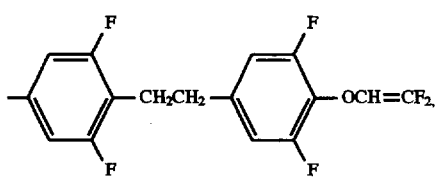
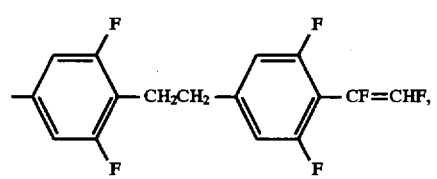

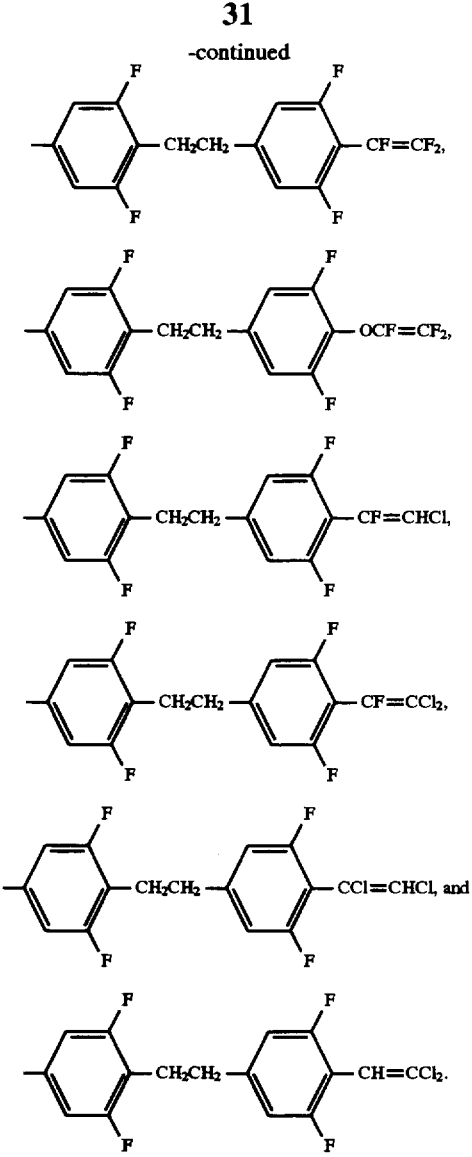

7-fluoroheptyl, 2,2-difluoroethyl, 2,2-difluoropropyl, 2,2-difluorobutyl, 2,2-difluoropentyl, 2,2-difluorohexyl, 2,2-difluoroheptyl, 4,4-difluorobutyl, 4,4-difluoropentyl, 4,4-difluorohexyl, 4,4-difluoroheptyl, 5,5-difluoropentyl, 5,5-difluorohexyl, 5,5-difluoroheptyl, 6,6-difluorohexyl, 6,6-difluoroheptyl, and 7,7-difluoroheptyl.

Preferred groups or atoms represented by W, $W_1$ and $W_2$ include H, F or $CH_3$.

Preferred examples of the moiety of the formula,

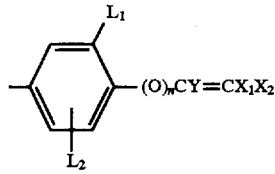

are as follows:

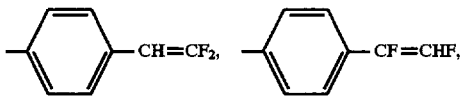

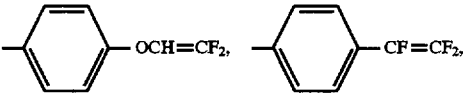

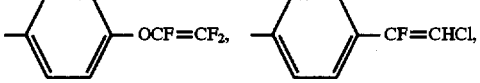

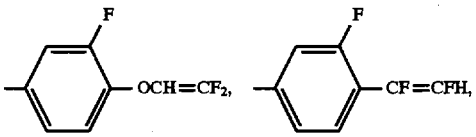

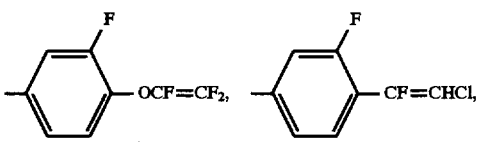

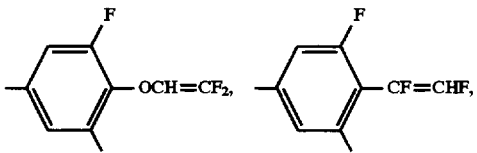

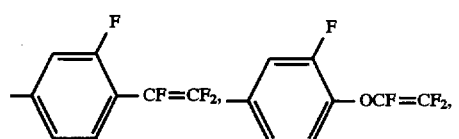

Among the compounds of the general formulas ($I_1$) to ($I_{30}$), the compounds of the formulas ($I_1$), ($I_4$), ($I_5$), ($I_6$), ($I_8$), ($I_{10}$), ($I_{12}$),($I_{15}$), ($I_{17}$), ($I_{20}$), ($I_{22}$), ($_{25}$), ($I_{27}$), and ($I_{29}$) are preferred.

The preferred groups represented by R include: linear alkyl groups having from 2 to 7 carbon atoms such as ethyl, n-propyl, n-butyl, n-pentyl, n-hexyl, and n-heptyl; branched alkyl groups having from 3 to 8 carbon atoms such as isopropyl, 1-methylbutyl, sec-butyl, isobutyl, 1-methylbutyl, 2-methylbutyl, 3-methylbutyl, 1-methylpentyl, 2-methylpentyl and 2-ethylhexyl; alkoxyalkyl groups having from 2 to 4 carbon atoms such as methoxymethyl, methoxyethyl, methoxypropyl, methoxypentyl, ethoxymethyl, ethoxyethyl, propoxymethyl, and pentoxymethyl; alkenyl groups having from 2 to 8 carbon atoms such as vinyl, 1-propenyl, 3-butenyl, 1-pentenyl, 3-pentenyl, 4-pentenyl, 1-hexenyl, 5-hexenyl, 6-heptenyl, and 7-octenyl; and mono or difluoroalkyl groups having from 1 to 10 carbon atoms such as 2-fluoroethyl, 2-fluoropropyl, 2-fluorobutyl, 2-fluoropentyl, 2-fluorohexyl, 2-fluoroheptyl, 4-fluorobutyl, 4-fluoropentyl, 4-fluorohexyl, 4-fluoroheptyl, 5-fluoropentyl, 5-fluorohexyl, 5-fluoroheptyl, 6-fluorohexyl, 6-fluoroheptyl, 6-fluorooctyl, -continued
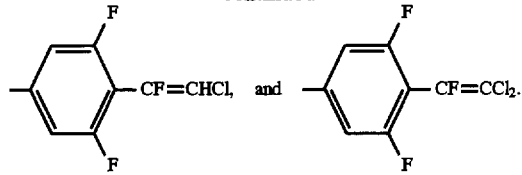
Preferred examples of the moiety of the formula
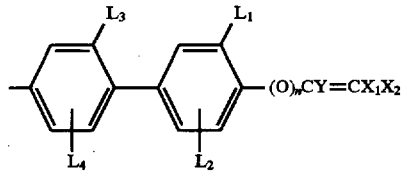
include:
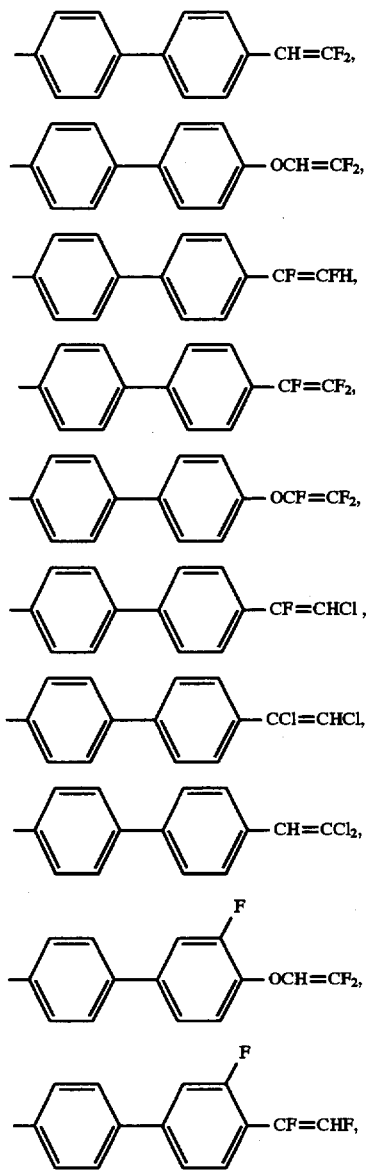
-continued
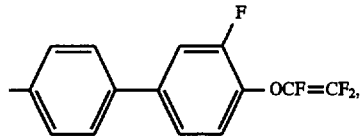
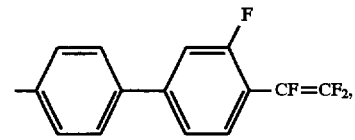
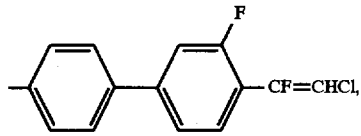
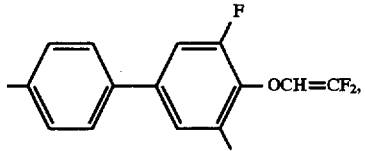
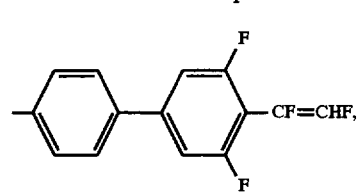
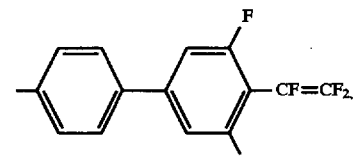
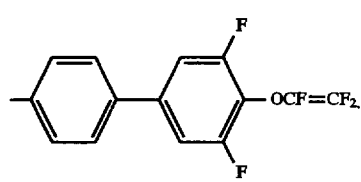
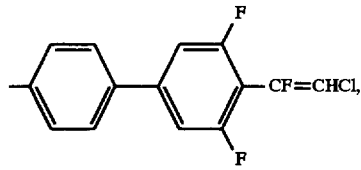
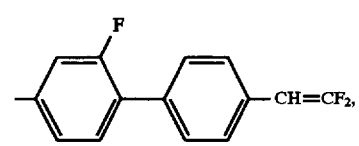
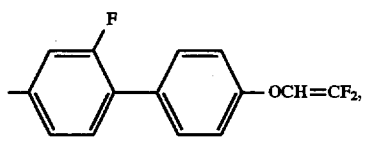

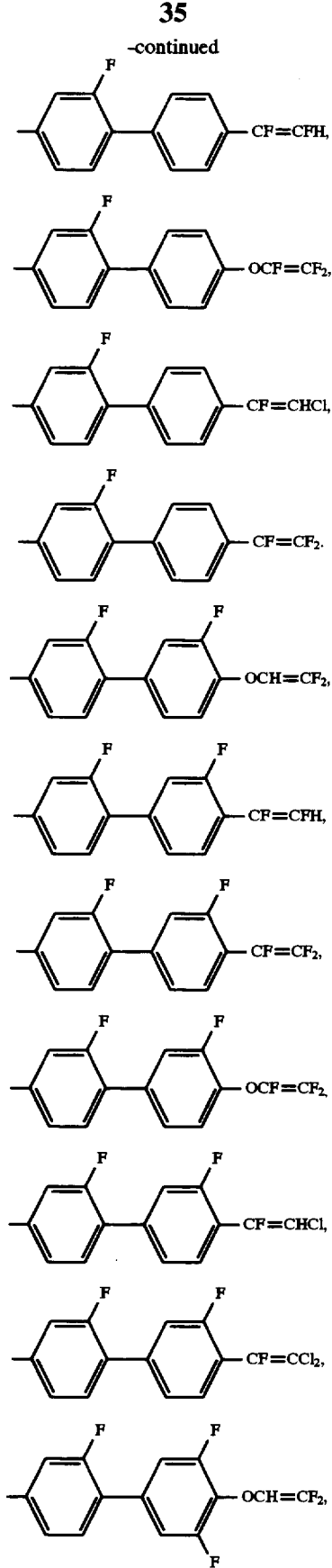
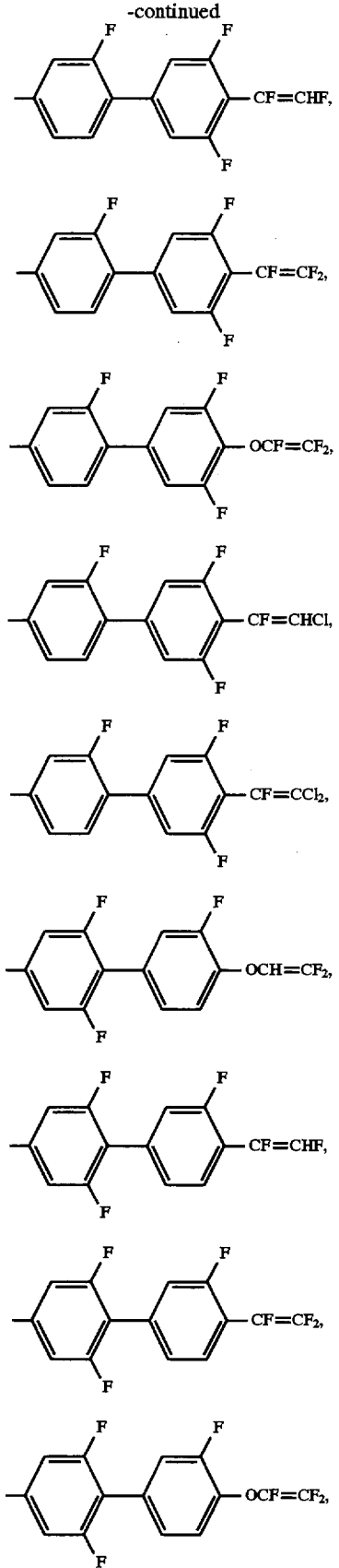

-continued
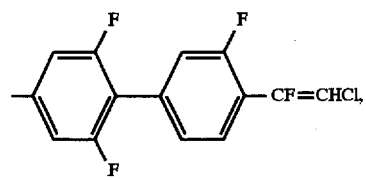
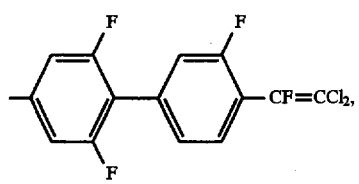
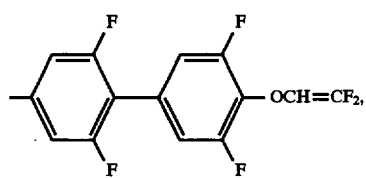
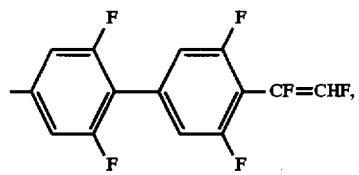
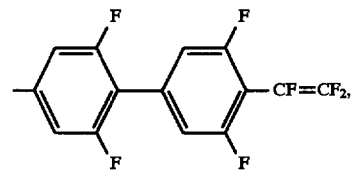
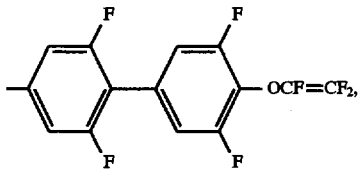
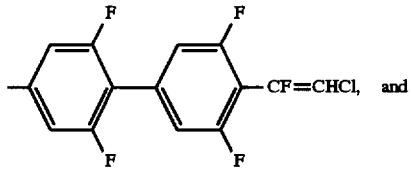
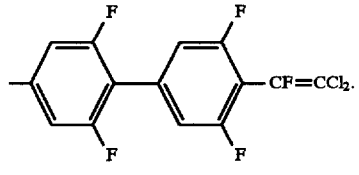
Preferred examples of the moiety of the formula
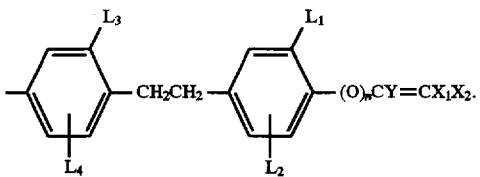
include:
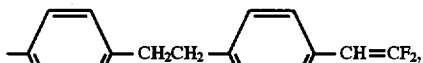
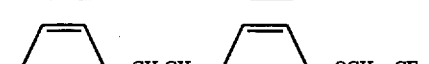
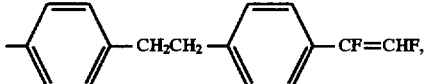
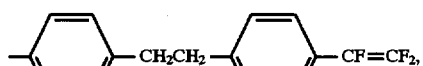
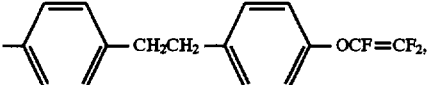
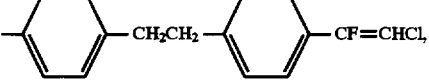
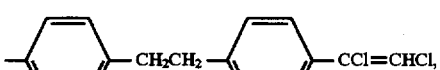
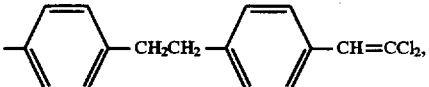
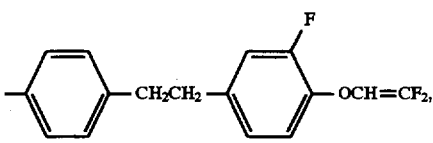
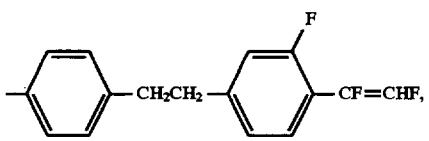

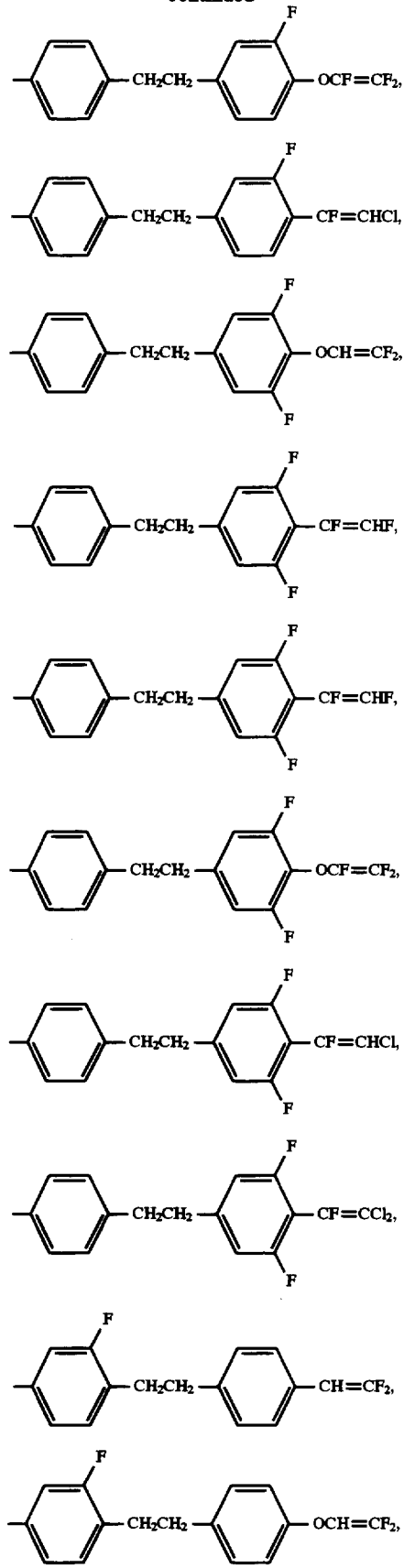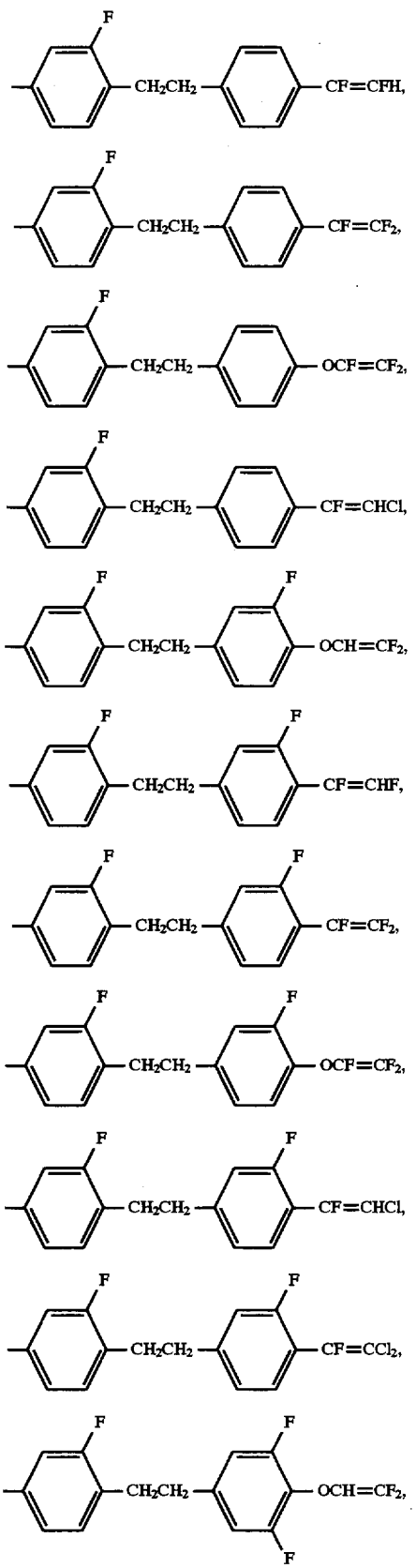

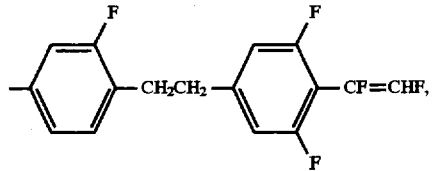

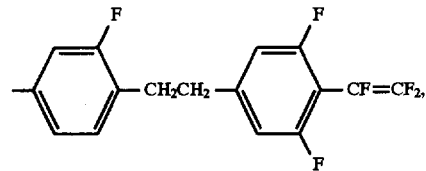

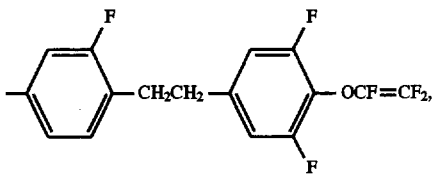

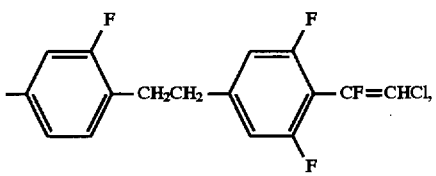

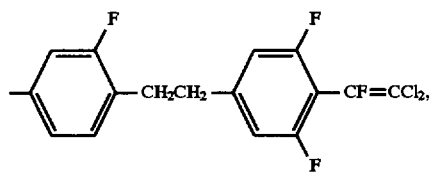

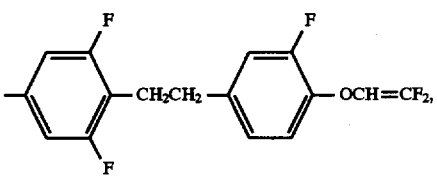

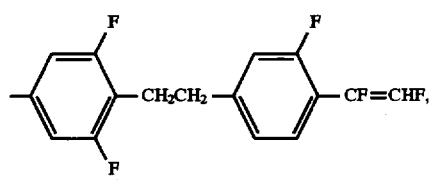

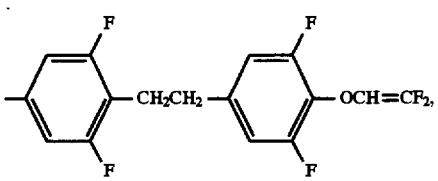

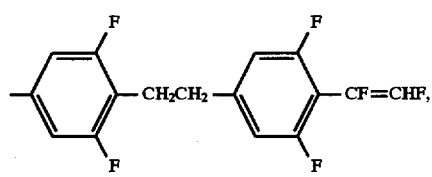

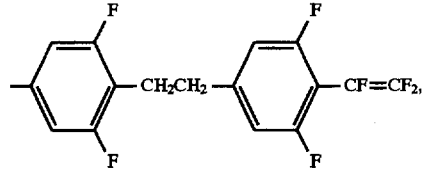

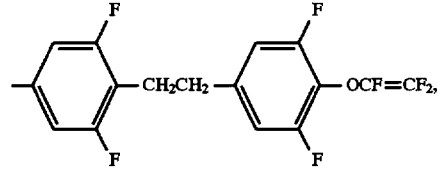

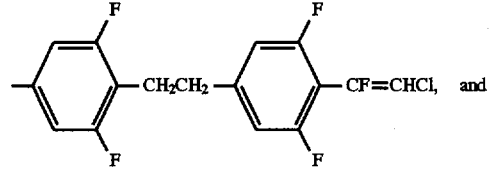

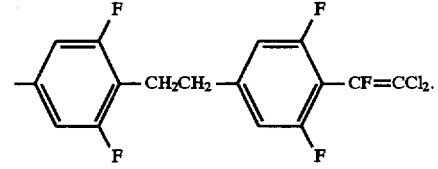

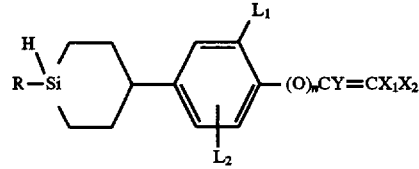

Typical processes for preparing the silacyclohexane compounds of the formula (I) according to the invention are described. In the following procedures, compounds of the formulas $(I_1)$ to $(I_{30})$ wherein W, $W_1$ and $W_2$ are, respectively, H are prepared for illustration. As a matter of course, other substituents such as F, Cl or $CH_3$ may be readily obtained as will be described hereinafter.

(1) Reaction 1-1: preparation of compounds of the formula

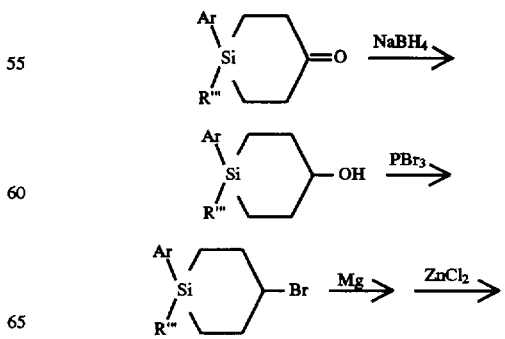

This type of compound can be prepared according to the following reaction sequence

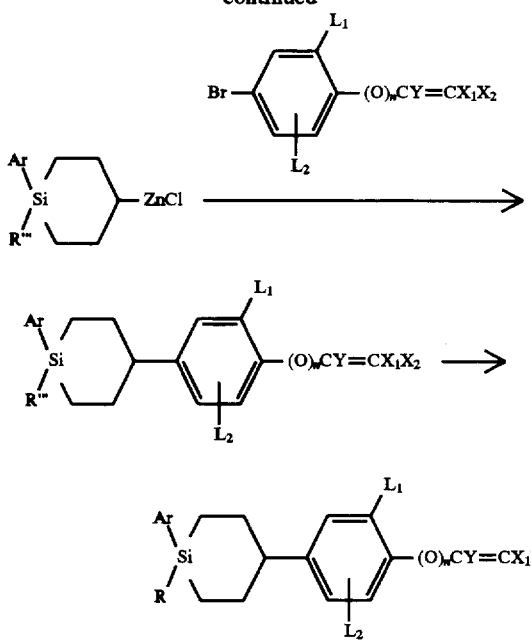

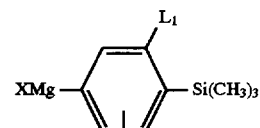

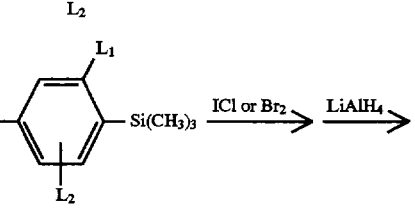

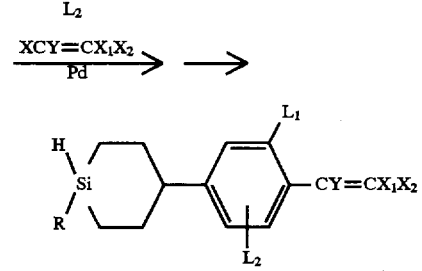

wherein Ar represents phenyl or tolyl, R''' represents Ar, a linear alkyl group having from 1 to 10 carbon atoms, a branched alkyl group having from 3 to 8 carbon atoms, an alkenyl group having from 2 to 8 carbon atoms, an alkoxyalkyl group having from 2 to 7 carbon atoms or a mono or difluoroalkyl group having from 1 to 10 carbon atoms.

In the above reaction sequence, a silacyclohexanone having the substituents at the silicon atom is reduced with hydrogen and then brominated such as with $PBr_3$ to obtain a silacyclohexyl bromide. Thereafter, the bromide product is reacted with Mg to provide a Grignard reagent and subjected to metal exchange to obtain an organozinc compound. Subsequently, the organozinc compound is subjected to coupling reaction with a corresponding bromide to obtain a silacyclohexylphenyl compound. The resultant compound is de-silylated with an electrophilic reagent such as a halide, a halogen or the like to obtain a halosilacyclohexane compound, followed by reduction to obtain the intended compound.

(2) Reaction 1-2: preparation of compounds of the formula

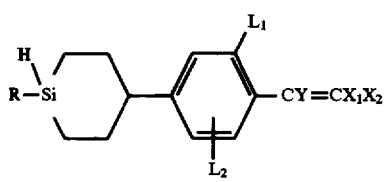

The compound may also be prepared according to the following procedure:

In the above reaction sequence, the silacyclohexanone having the substituents joined to the silicon atom is reacted with a silyl-protected Grignard reagent to obtain a tertiary alcohol. The alcohol is dehydrated and hydrogenated to obtain a silacyclohexylphenyl compound. The compound is de-silylated with an electrophilic reagent such as ICl or $Br_2$ to obtain a halosilane, followed by reduction with a metal hydride such as $LiAlH_4$ to obtain a hydrosilane. The thus obtained hydrosilane is reacted with Mg to obtain a Grignard reagent, followed by reaction with $ZnCl_2$ to obtain an organozinc reagent. This reagent is reacted with a haloethylene halide of the formula, $XCY=CX_1X_2$ wherein X is Br, Cl or I, to obtain a haloethylene-substituted silacyclohexylphenyl compound.

It should be noted that in the above reaction sequence, the single ring silacyclohexanone is used, and when a silacyclohexylcyclohexanone or silacyclohexylsilacyclohexanone having a two ring structure is used as a starting hexanone, silacyclohexane compounds having a three-ring structure are prepared in a similar way.

(3) Reaction 2: preparation of compounds of the formula

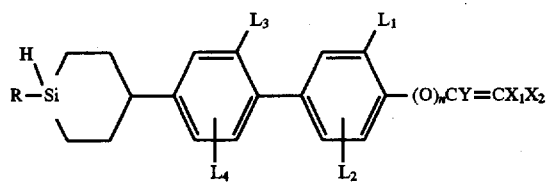

This compound is prepared according to the following procedure:

tion in the presence of an acid catalyst and hydrogenation of the resulting double bond to obtain a silacyclohexylphenyl compound.

Subsequently, the compound is subjected to de-silylation reaction with an electrophilic reagent to convert the Ar group and the —Si(CH$_3$)$_3$ protective group to a halogen at the same time to obtain a halosilane. The halosilane is reduced into a hydrosilane. The thus obtained hydrosilane is reacted with a metal such as Mg for conversion to an organometallic reagent such as a Grignard reagent. The reagent is coupled with a phenyl halide having an intended substituent of —(O)$_n$CY=CX$_1$X$_2$ to obtain the intended compound.

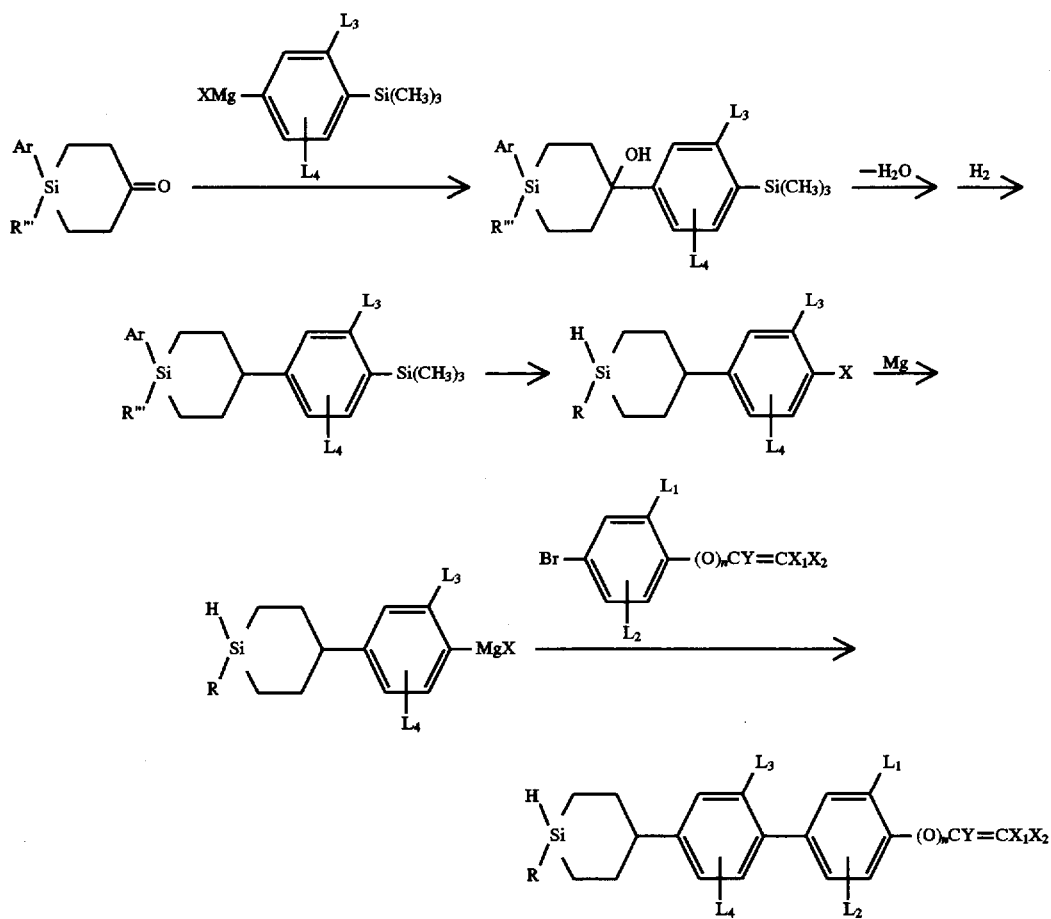

wherein X represents a halogen such as Cl, Br or I.

In the above procedure, a silacyclohexanone having the substituents joined to the silicon atom is reacted with an organometallic reagent such as a Grignard reagent to provide a tertiary alcohol, followed by hydrolysis or dehydra- (4) Reaction 3: preparation of compounds of the formulas

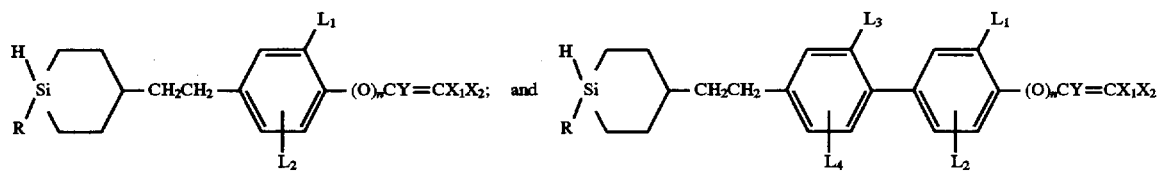

These compounds are prepared according to the following procedures:

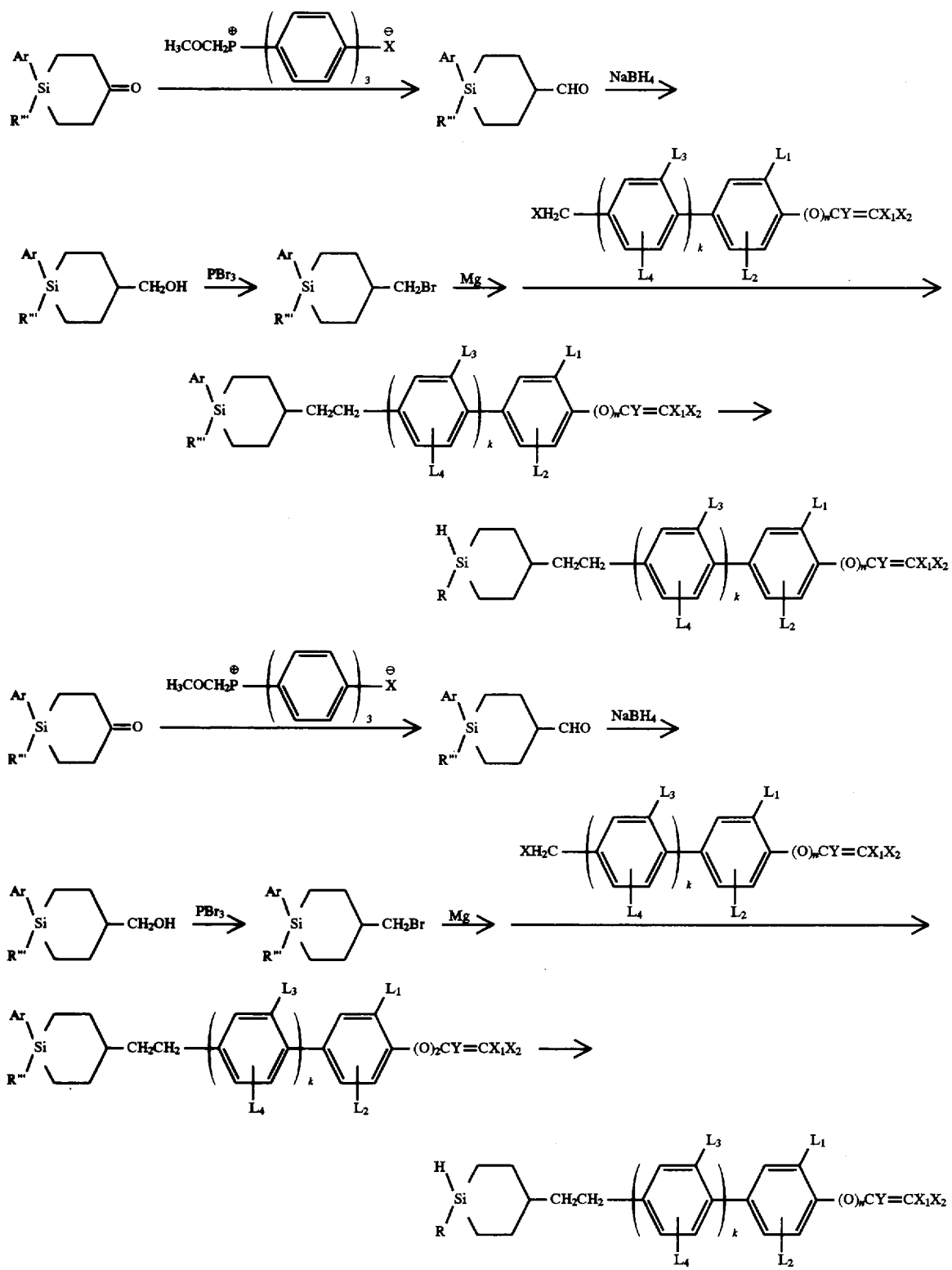

wherein X represents Cl, Br or I, and k is 0 or 1.

In the above reaction sequence, a silacyclohexanone having the substituents joined to the silicon atom is subjected to the Wittig reaction with a phosphonium salt as shown, thereby obtaining a silacyclohexane carbaldehyde. Thereafter, the carbaldehyde is reduced with a metal hydride such as sodium borohydride and then halogenated with a halogenating reagent such as phosphorus tribromide to obtain a silacyclohexylmethyl halide. The halide compound is reacted with Mg to obtain a Grignard reagent, followed by coupling reaction with a corresponding benzyl halide to obtain a silacyclohexylethylphenyl compound. The compound is then reduced to obtain the intended compound.

(5) Reaction 4-1: preparation of compounds of the formula

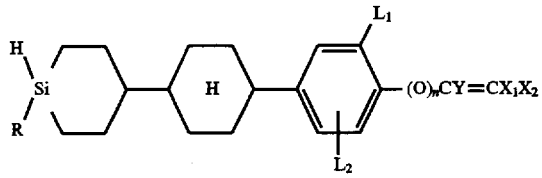

The compound is prepared according to the following procedure:

In the above reaction sequence, a silacylohexylcyclhexanone having the substituents joined to the silicon atom is reduced with a metal hydride such as sodium borohydride and then halogenated with a halogenating reagent such as phosphorus tribromide to obtain a silacyclohexylcyclohexyl halide. The halide is reaction with metallic magnesium to obtain a Grignard reagent, followed by metal exchange to obtain an organozinc reagent. Subsequently, the organozinc reagent is subjected to coupling reaction with a corresponding phenyl halide to obtain a silacyclohexylcyclohexylphenyl compound as shown. The thus obtained compound is de-silylated with an electrophilic reagent to obtain a halosilacyclohexane compound, followed by reduction to obtain the intended compound.

(6) Reaction 4-2: preparation of compounds of the formula

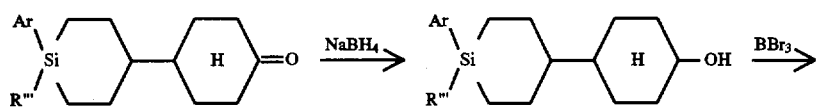

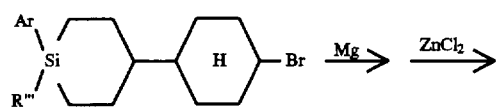

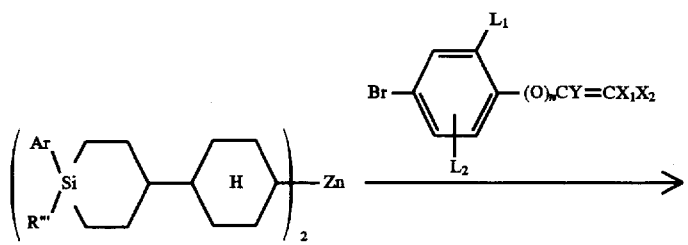

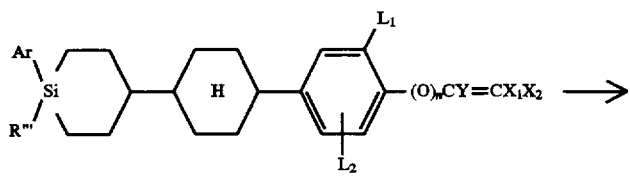

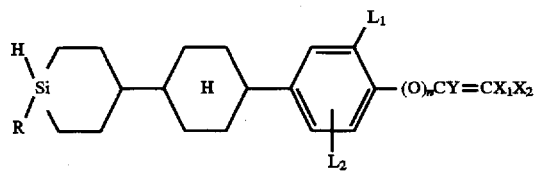

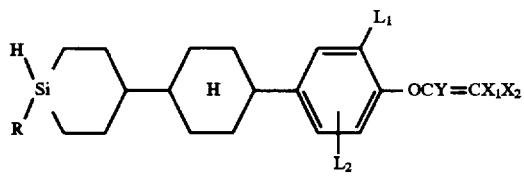

The compound may be obtained according to another procedure shown below:

nium fluoride (TBAF) to provide a phenol compound. Then, the compound is reacted with NaH to obtain a sodium phenolate, followed by further reaction with a fluoroalkyl bromide to obtain a fluoroalkyl phenol ether. Subsequently, the ether is dehydrofluorinated with a base such as t-$C_4H_9$OK, followed by de-silylation with an electrophilic reagent such as a halide and reduction to obtain the intended compound.

In the Reactions 4-1 and 4-2, the compounds obtained have the cyclohexylene group as the intermediate ring, and those compounds having an intermediate silacyclohexylene

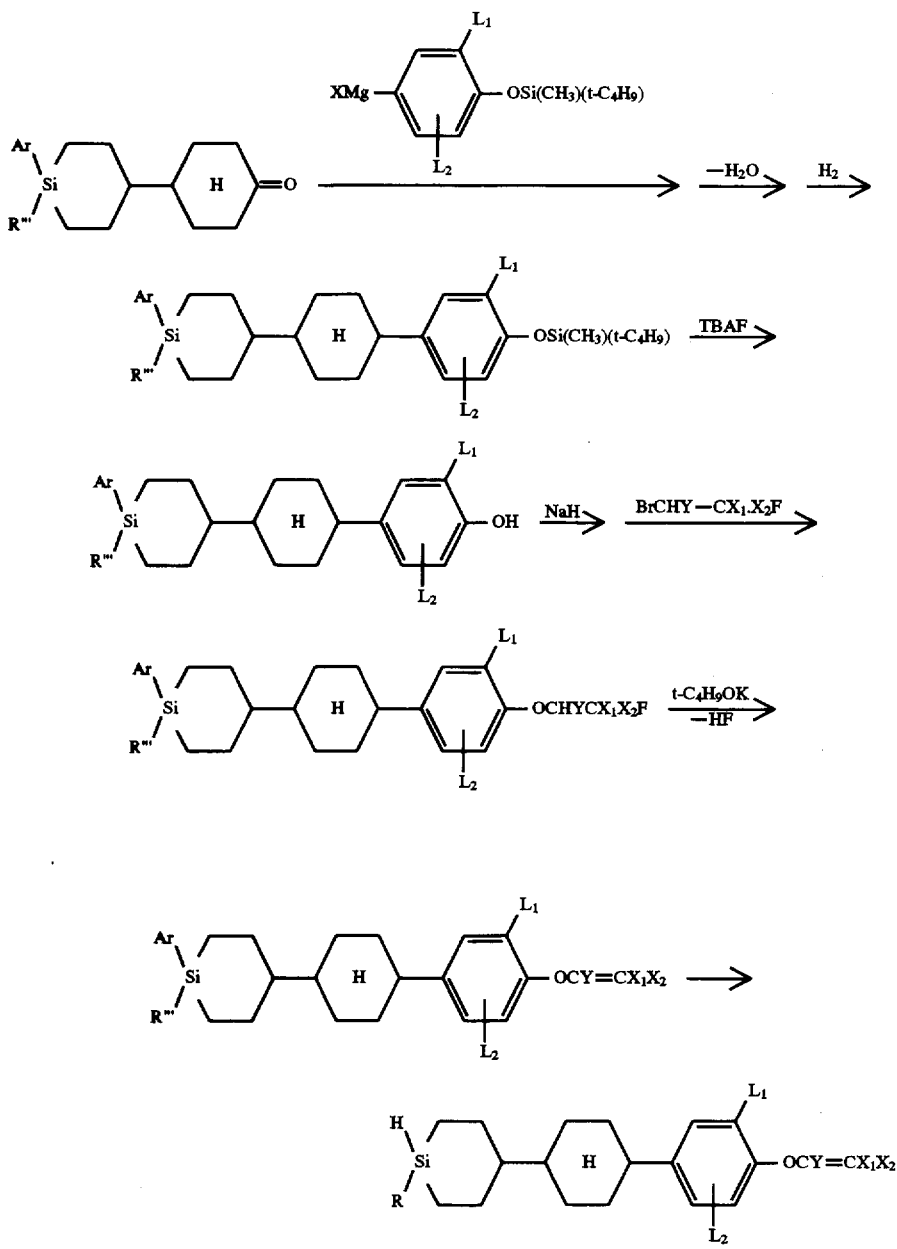

A silacyclohexylcyclohexanone having the substituents joined to the silicon atom is reacted with a silyl-protected Grignard reagent in the same manner as in Reaction 1-2, followed by dehydration and hydrogenation. Thereafter, the protective group is eliminated by use of tetrabutylammo- group having the silicon atom at the 1 or 4 position may be readily obtained in a similar way. This is true of sequences of Reactions 5, 6, 7-1 and 7-2 appearing hereinafter.

(5) Reaction 5: preparation of compounds of the formula

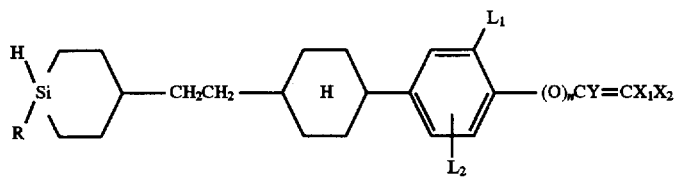

The compound is prepared according to the following procedure:

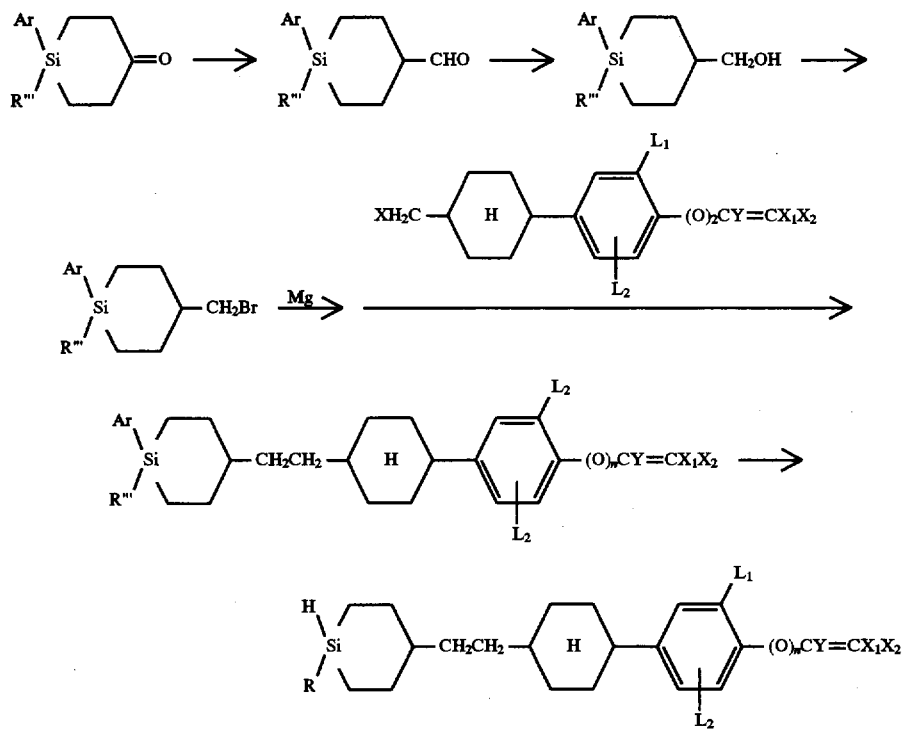

Like the reaction 3, a silacyclohexylmethyl halide is obtained from a silacyclohexanone compound having the substituents joined to the silicon atom. The halide is reacted with Mg to obtain a Grignard reagent, followed by reaction with a corresponding phenylcyclohexylmethyl halide to obtain a silacyclohexylethylcyclohexylphenyl compound. The compound is de-silylated and reduced to obtain the intended compound.

(8) Reaction 6: preparation of compounds of the formula

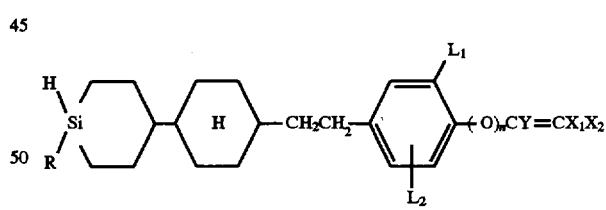

This compound is prepared according to the following procedure:

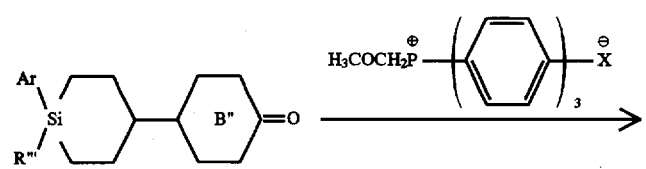

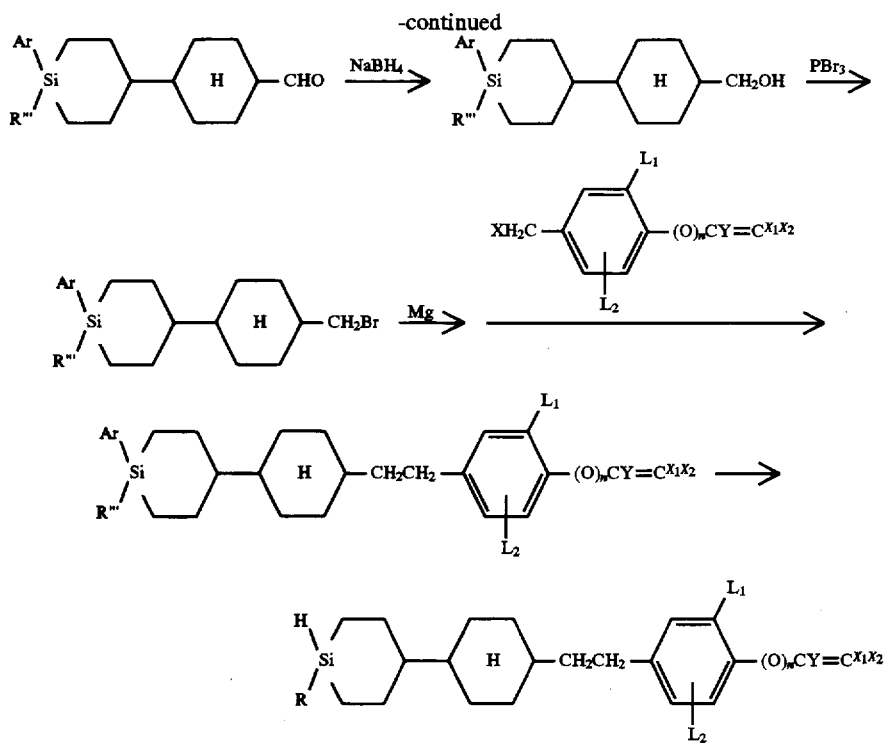

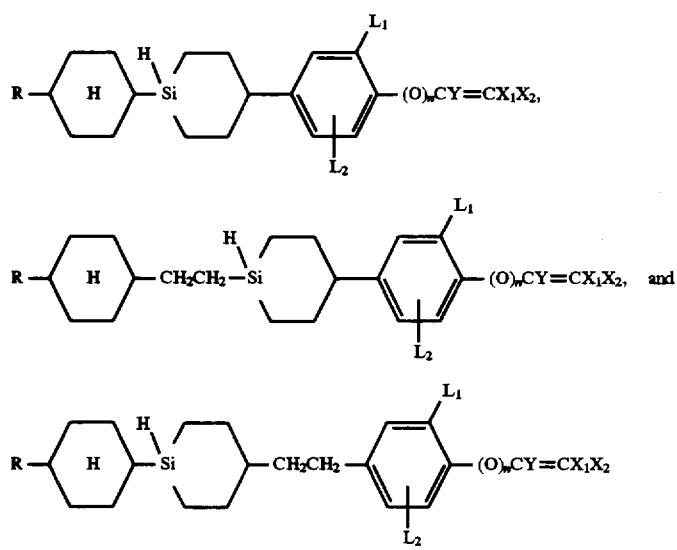

Like the reaction 3, a silacyclohexylcyclohexylmethyl halide is prepared from a silacyclohexylcyclohexanone having the substituents joined to the silicon atom. The halide is reacted with Mg to provide a Grignard reagent, followed by coupling reaction with a corresponding benzyl halide to obtain a silacyclohexylcyclohexylphenyl compound. The compound is de-silylated and reduced to obtain the intended compound.

(9) Reaction 7-1: preparation of compounds of the following formulas

These compounds are prepared according to the following reaction sequence:

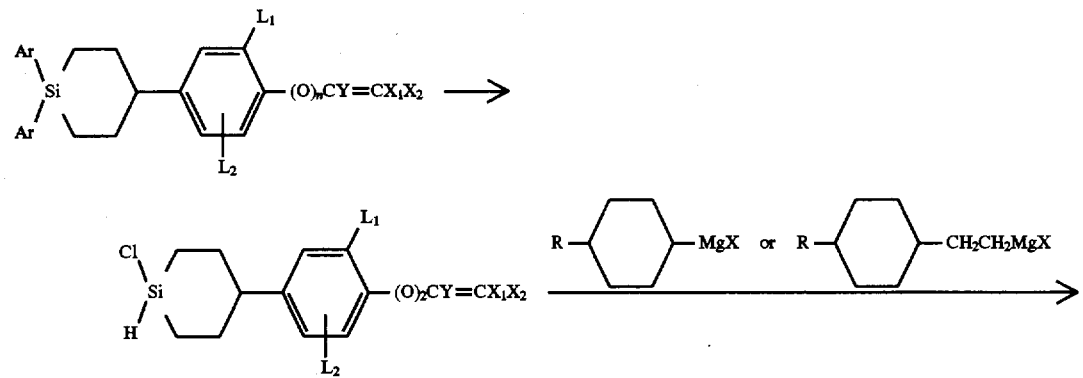

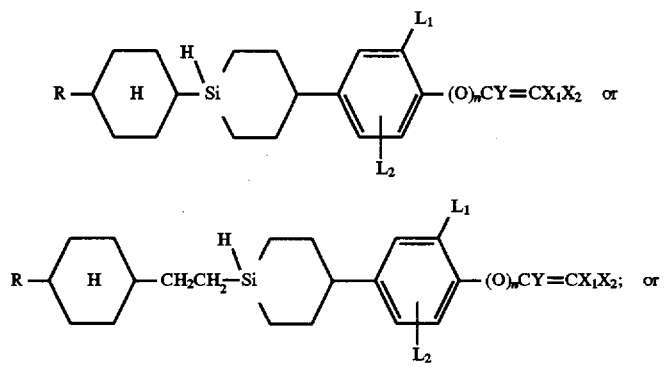

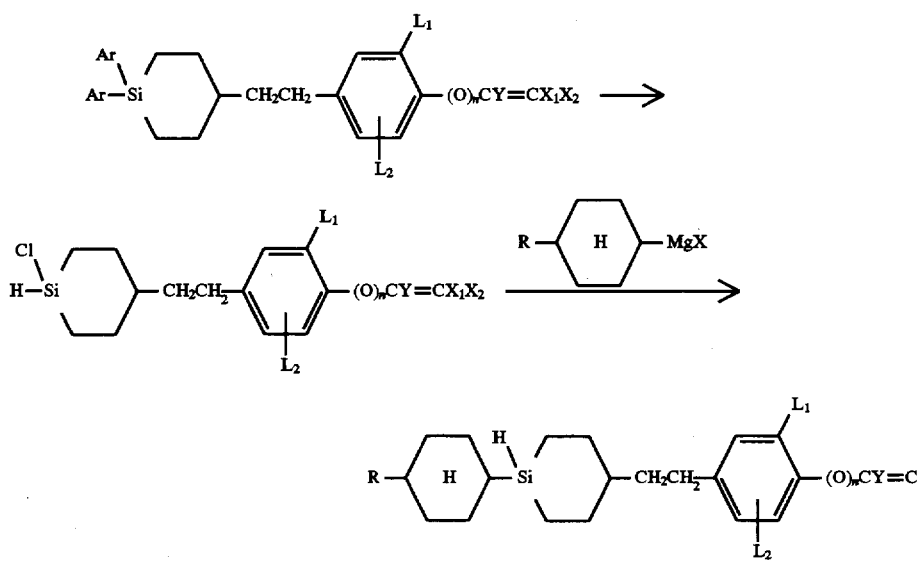

In the above reaction sequences, diarylsilacyclohexane compounds where R is Ar in the foregoing Reactions 1 and 3 are, respectively, provided as starting compounds, and are subjected to halo-de-silylation with an electrophilic reagent, reduction and monohalogenation to obtain hydrohalogenosilane compounds. The compounds are, respectively, reacted with corresponding Grignard reagents to obtain individual intended compounds.

(10) Reaction 7-2: preparation of compounds of the formula

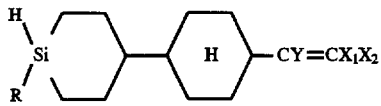

The compound of the above formula may be prepared according to the following procedure:

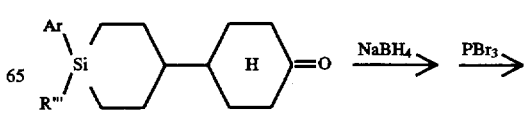

-continued

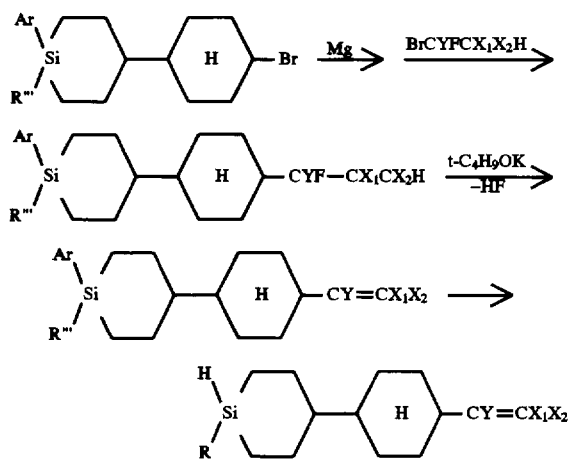

In the same manner as in Reaction 1-1, a silacyclohexylcyclohexanone having the substituents joined to the silicon atom is converted through a corresponding alcohol to a bromide. The bromide is reacted with Mg to provide a Grignard reagent and then reacted with $BrCYFCX_1X_2H$ to obtain a fluloroalkyl-substituted compound. Subsequently, the compound is dehydrofluorinated with a base such as $t-C_4H_9OK$, followed by de-silylation with an electrophilic regent and reduction to obtain the intended compound.

In the foregoing reaction sequences, the preparation of the compounds of the general formulas $(I_1)$ to $(I_{30})$ wherein W, $W_1$ and/or $W_2$ is hydrogen. Compounds of the formulas $(I_1)$ to $(I_{30})$ where W, $W_1$ and/or $W_2$ is other substituent such as Cl, F or $CH_3$ can be prepared in the following manner wherein the related moiety alone is shown for convenience's sake:

tetra-n-butylammonium fluoride or the like to obtain a fluorosilacyclohexylene group. This conversion reaction is effected at a temperature ranging from 0° C. to a refluxing temperature of a solvent. The solvent used may be hexane, heptane, benzene, toluene or the like.

When the dichlorosilacyclohexylene group is reacted with $CH_3L$ where L represents MgP in which P is a halogen atom, ZnP or Li, e.g. a methylmagnesium halide, a methyl group can be introduced as shown. A further reaction with a Grignard agent results in a methylsilacyclohexylene group.

As a matter of course, if the chlorosilacyclohexylene group or fluorosilacyclohexylene group is reacted under mild conditions with metal hydrides such as sodium hydride, calcium hydride, trialkylsilanes, boranes, dialkylaluminium and the like, or complex hydrides such as aluminium lithium hydride, sodium borohydride, lithium borohydride, tributylammonium borohydride and the like. This reduction reaction is preferably effected at a temperature from −50° to 100° C., more preferably from −20° C. to 70° C. This reaction is carried out in solvents including ethers such as diethyl ether, tetrahydrofuran and the like, or aromatic hydrocarbons such as benzene, toluene and the like.

The thus obtained compound consists of a mixture of cis and trans isomers with respect to the steric arrangement of the substituent or substituents of the silacyclohexylene group and/or cyclohexylene group. The mixture is usually purified through any ordinary procedure such as recrystallization, chromatography or the like to obtain an intended trans isomer or trans, trans isomer. These isomers are useful as a liquid crystal substance.

The liquid crystal composition comprising at least one silacyclohexane compound of the formula (I) according to the invention is described. The liquid crystal composition of the invention should preferably comprise at least one silacyclohexane compound of the formula (I) and at least one compound selected from compounds of the afore-indicated general formulas (II) to (VI).

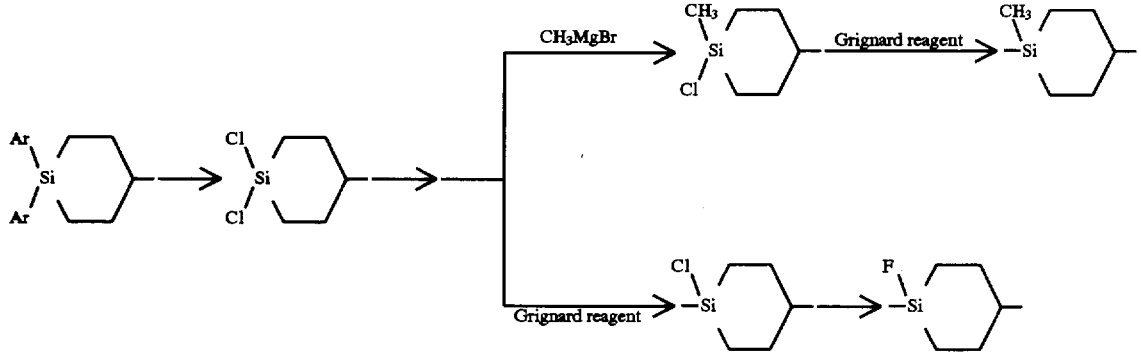

In the above reaction sequence, the diarylsilacyclohexyl group is halo-desilylated with an electrophilic reagent such as iodine monochloride to convert to a dichlorosilacyclohexyl group. This de-silylation reaction is preferably effected at a temperature of from 0° to 80° C., more preferably from 10° to 40° C. The reaction is usually conducted in a hydrocarbon solvent. Specific examples of the hydrocarbon solvent include dichloromethylene, chloroform, carbon tetrachloride and the like.

The thus converted dichlorosilacyclohexylene group may be further reacted with a corresponding Grignard reagent for conversion to a chlorosilacylohexylene group and then reacted with a fluoride such as cesium fluoride, copper (I) fluoride, antimony fluoride, zinc fluoride, calcium fluoride, Specific chemical structures of the compounds of the formula (II) include those of the formulas (IIa) to (IIe) mentioned below:

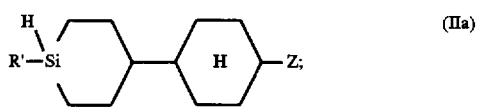

(IIa)

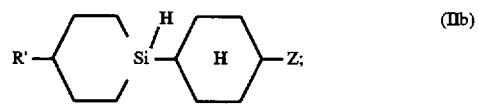

(IIb)

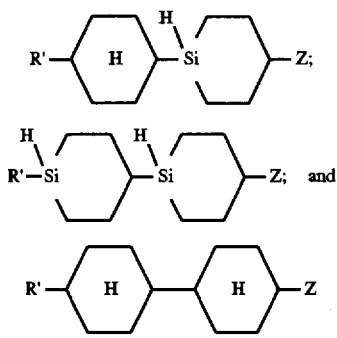

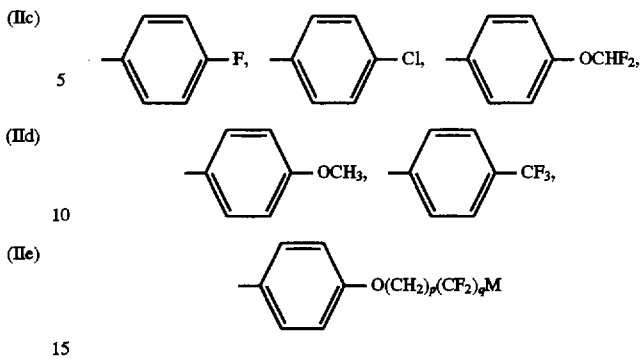

Specific examples of the moiety are shown below:

These compounds should consist of a trans isomer with respect to the steric arrangement of the silacyclohexane ring or rings and the cyclohexane ring or rings.

In the above formulas, R' represents a liner alkyl group having from 1 to 7 carbon atoms, an alkoxyalkyl group having from 2 to 7 carbon atoms, a mono or difluoroalkyl group having from 2 to 7 carbon atoms, and an alkenyl group having from 2 to 8 carbon atoms. Specific examples of the linear alkyl group include methyl, ethyl, n-propyl, n-butyl, n-pentyl, n-hexyl and n-heptyl.

Specific examples of the alkoxyalkyl group include methoxymethyl, 2-methoxyethyl, 3-methoxypropyl, 4-methoxybutyl, 5-methoxypentyl, 6-methoxyhexyl, ethoxymethyl, 2-ethoxyethyl, 3-ethoxypropyl, 4-ethoxybutyl, 5-ethoxypentyl, (n-propoxy)methyl, 2-(n-propoxy)ethyl, 3-(n-propoxy)propyl, 4-(n-propoxy)butyl, (n-butoxy)methyl, 2-(n-butoxy)ethyl, 3-(n-butoxy)propyl, (n-pentoxy)methyl, 2-(n-pentoxy)ethyl, and (n-hexyloxy) methyl.

Specific examples of the mono or difluoroalkyl group include 1-fluoroethyl, 1-fluoropropyl, 1-fluorobutyl, 1-fluoropentyl, 1-fluorohexyl, 1-fluoroheptyl, 2-fluoroethyl, 2-fluoropropyl, 2-fluorobutyl, 2-fluoropentyl, 2-fluorohexyl, 2-fluoroheptyl, 3-fluoropropyl, 3-fluorobutyl, 3-fluoropentyl, 3-fluorohexyl, 3-fluoroheptyl, 4-fluorobutyl, 4-fluoropentyl, 4-fluorohexyl, 4-fluoroheptyl, 5-fluoropentyl, 5-fluorohexyl, 5-fluoroheptyl, 6-fluorohexyl, 6-fluoroheptyl, 7-fluoroheptyl, 1,1-difluoroethyl, 1,1-difluoropropyl, 1,1-difluorobutyl, 1,1-difluoropentyl, 2,2-difluoroethyl, 2,2-difluoropropyl, 2,2-difluorobutyl, 2,2-difluoropentyl, 3,3-difluoropropyl, 3,3-difluorobutyl, 3,3-difluoropentyl, 4,4-difluorobutyl, 4,4-difluoropentyl, and 5,5-difluoropentyl.

Specific examples of the alkenyl group include vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4E-hexenyl, 4Z-hexenyl, 4E-heptenyl, 4Z-heptenyl, 5-hexenyl, 5E-heptenyl, 5Z-heptenyl, and 6-heptenyl.

The silacyclohexane compound of the formula (II) has the moiety of the following formula

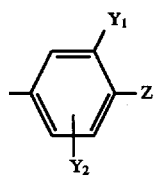

wherein p and q are, respectively 0, 1 or 2 provided that (p+q)=2, 3 or 4, and M is H, F or Cl,

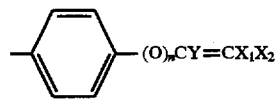

wherein n, Y, $X_1$ and $X_2$ are, respectively, as defined hereinbefore, i.e. n is 0 or 1, $X_1$ and Y, respectively, represent H, F or Cl, and $X_2$ represents F or Cl,

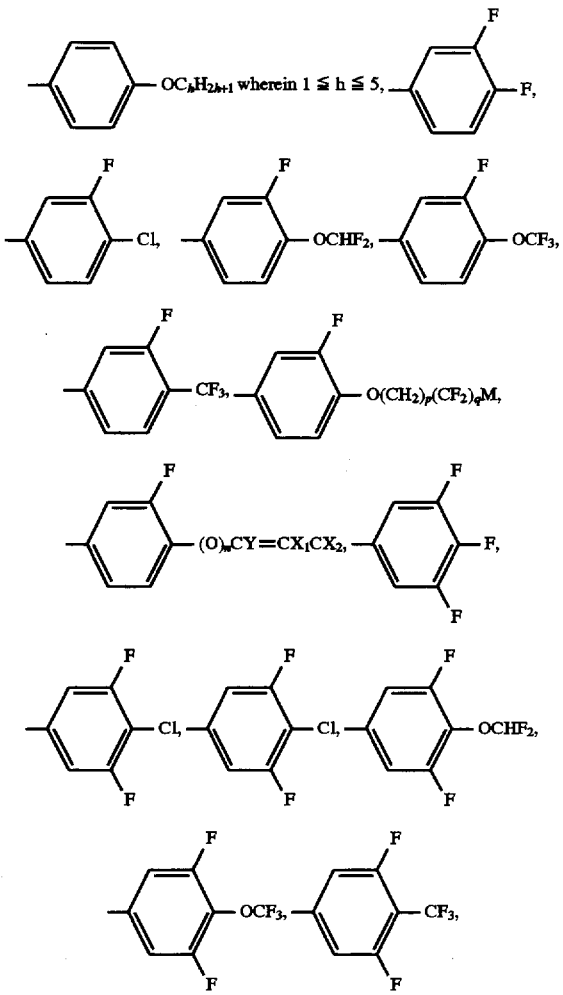

-continued

![structure with two fluorinated phenyl rings connected by O(CH₂)ₚ(CF₂)ₑM and (O)ₘCY=CX₁CX₂]

and

![2,3-difluorophenyl-OCₖH₂ₖ₊₁]

The specific chemical structures of the compound of the formula (III) are those of the formulas (IIIa) to (IIIh) indicated below:

![formula IIIa] (IIIa)

![formula IIIa duplicate] (IIIa)

![formula IIIc] (IIIc)

![formula IIId] (IIId)

![formula IIIe] (IIIe)

![formula IIIf] Z;(IIIf)

-continued

![formula IIIg] (IIIg)

![formula IIIh] (IIIh)

In the above formulas, the steric arrangement is the same as set out with respect to the formulas (IIa) to (IIe). This is true of R' and the moiety of the formula ![moiety with Y₁, Z, Y₂ on phenyl]

The specific chemical structures of the compounds of the formula (IV) include those of the formulas (IVa) to (IVh):

![formula IVa] (IVa)

![formula IVb] (IVb)

![formula IVc] (IVc)

![formula IVd] (IVd)

![formula IVe] (IVe)

-continued

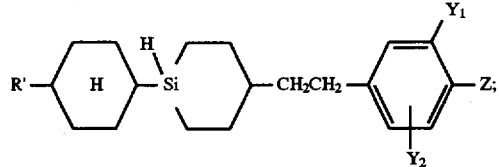 (IVf)

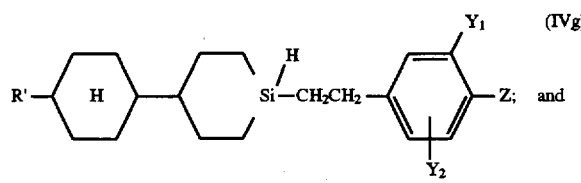 (IVg) and

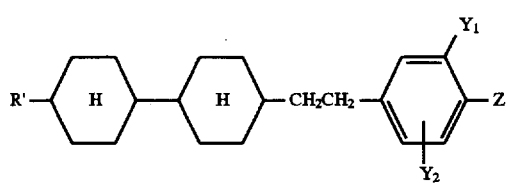 (IVh)

In this case, the steric arrangement, definition of R' and the moiety of the formula

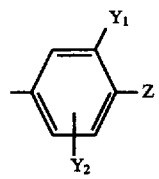

are, respectively, as in the formula (II).

The specific chemical structures of the compound of the formula (V) are those of the formulas (Va) to (Ve) indicated below:

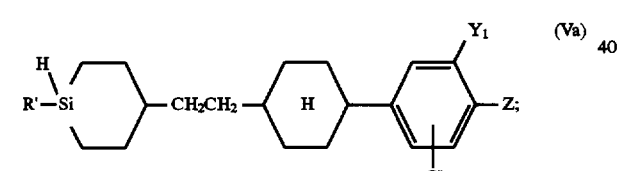 (Va)

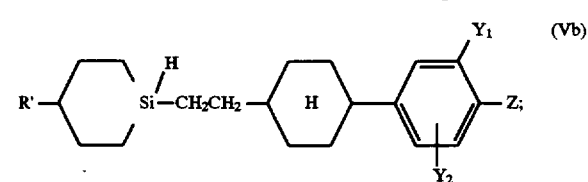 (Vb)

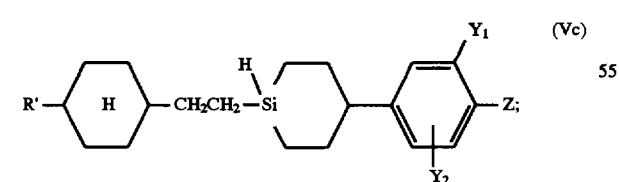 (Vc)

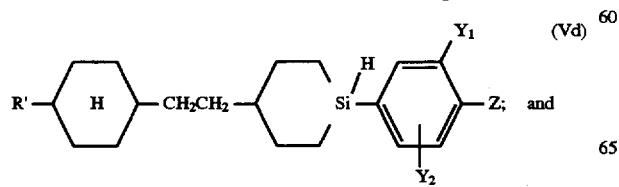 (Vd) and

-continued

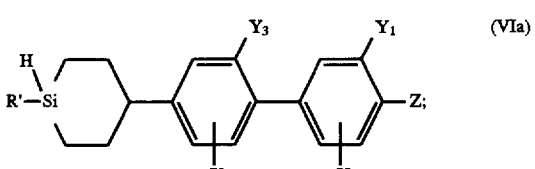 (Ve)

In this case, the steric arrangement, R' and the specific examples of the moiety of the formula

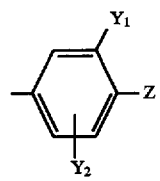

are, respectively, those having set out in the formula (II).

The specific chemical structures of the compounds of the general formula (VI) are those of the following formulas (VIa), (VIb) and (VIc):

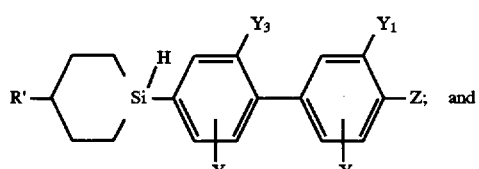 (VIa)

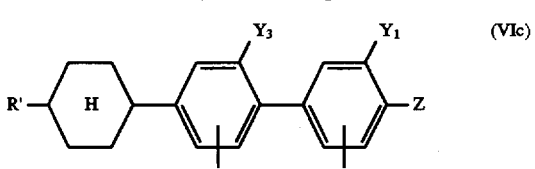 (VIb) and

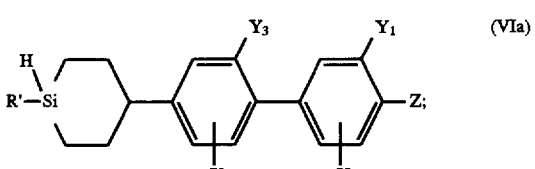 (VIc)

The steric arrangement and the definition of R' are, respectively, as in the foregoing formulas.

Specific examples of the moiety of the formula

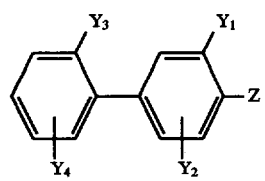

are shown below:

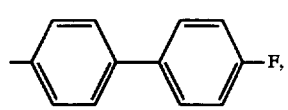

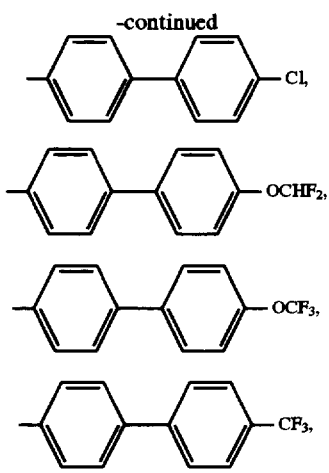
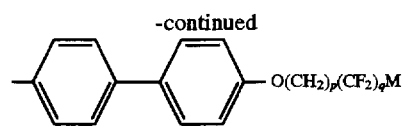
wherein p and q are, respectively, 0, 1 or 2 provided that (p+q)=2, 3 or 4, and M is H, F or Cl,
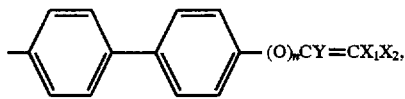
wherein n is 0 or 1, $X_1$ and Y are, respectively, H, F or Cl, and $X_2$ is F or Cl,
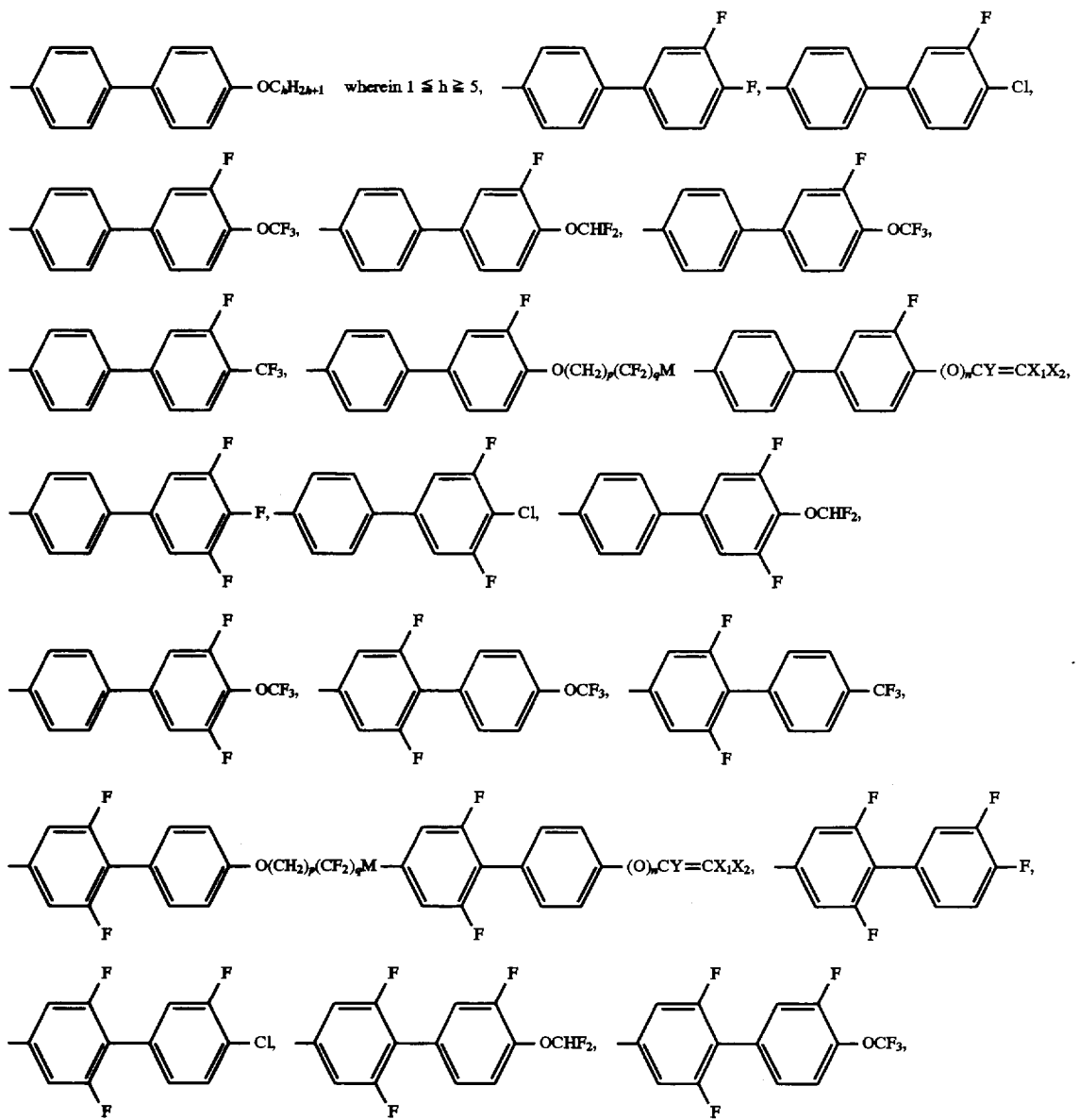

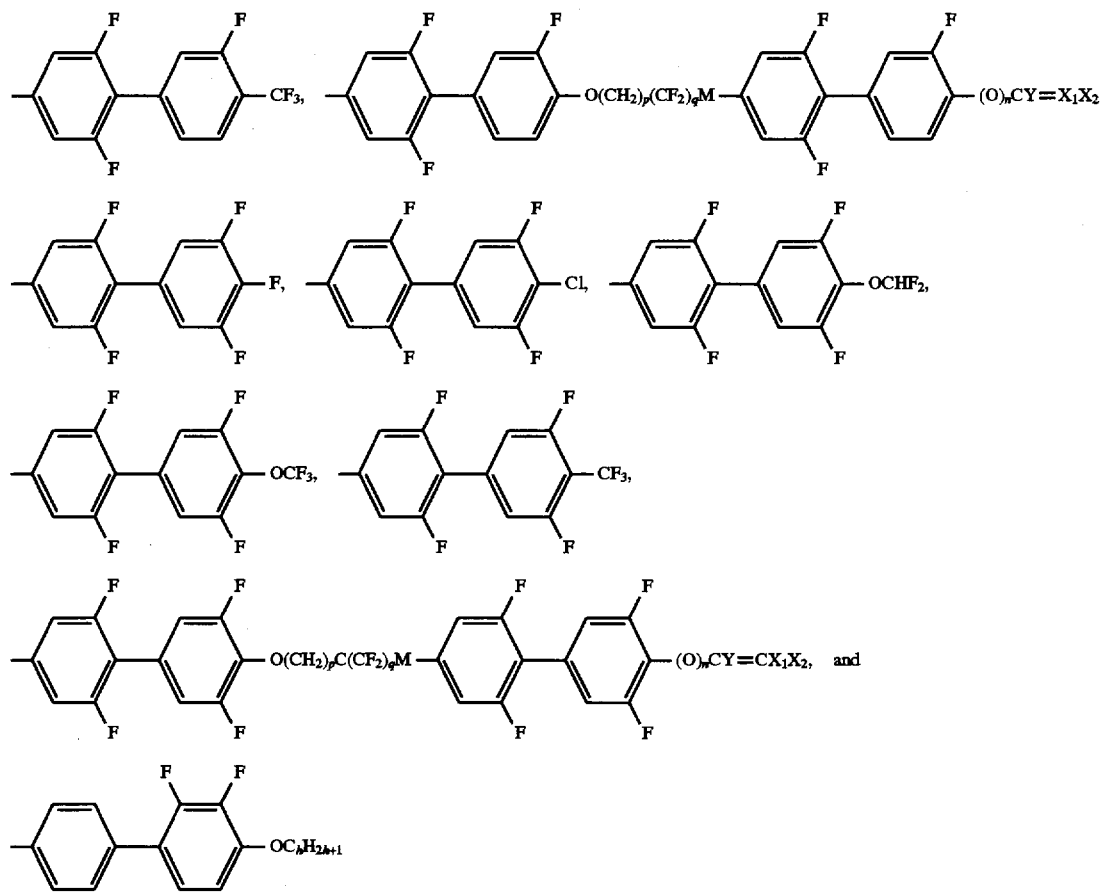
The specific chemical structures of the compounds of the formula (VII) include those shown below:
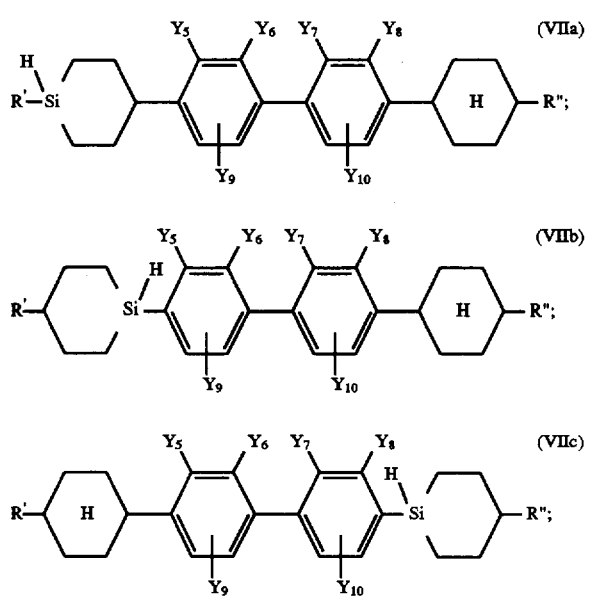
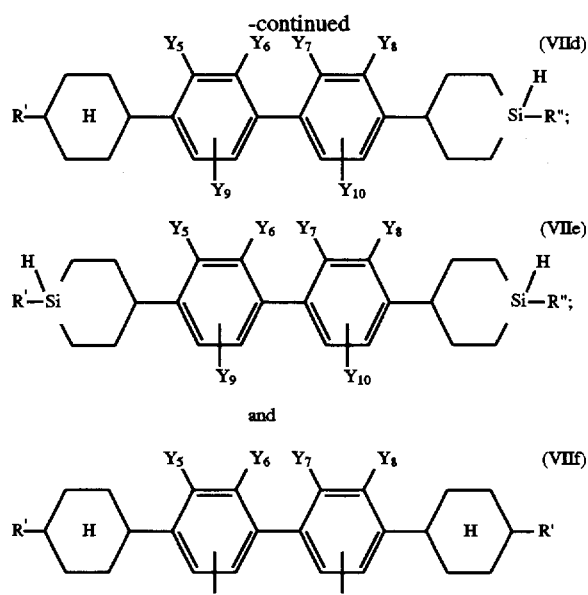
In the above formulas, $Y_5$ to $Y_{10}$ are, respectively, H or F.
The steric arrangement and R' are, respectively, as defined in the formula (II). R" is same as R'.

The moiety of the formula
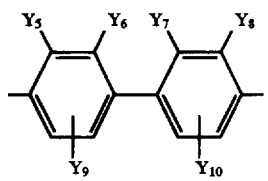
includes ones shown below:
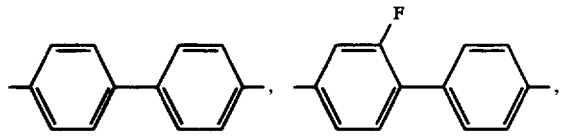
-continued
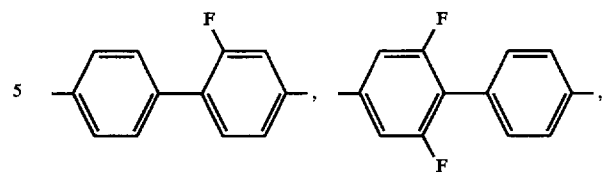
and
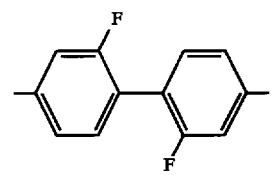
The specific chemical structures of the compounds of the formula (VIII) are those mentioned below:
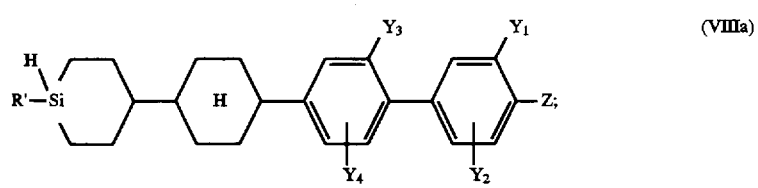
(VIIIa)
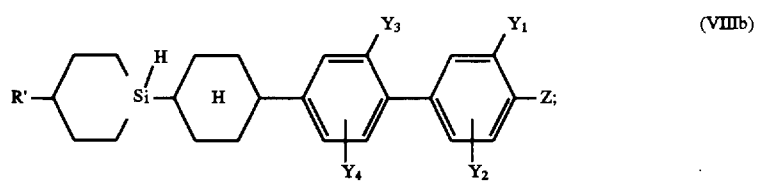
(VIIIb)
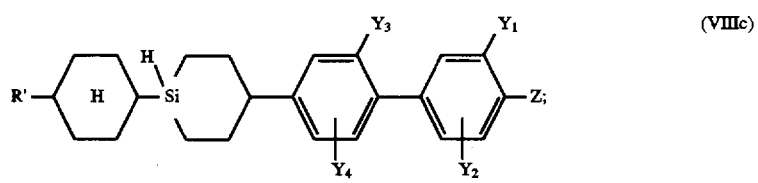
(VIIIc)
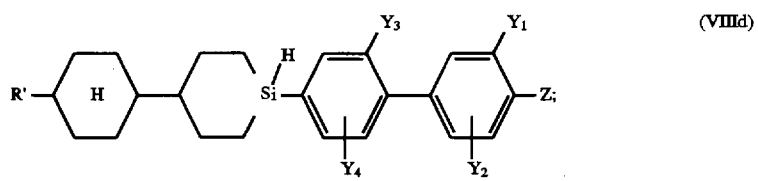
(VIIId)
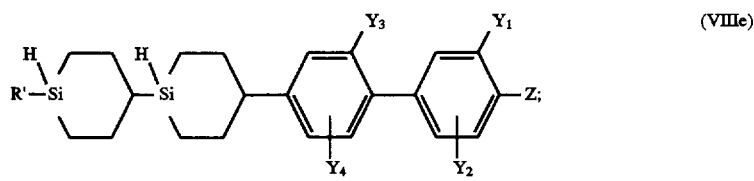
(VIIIe)

-continued

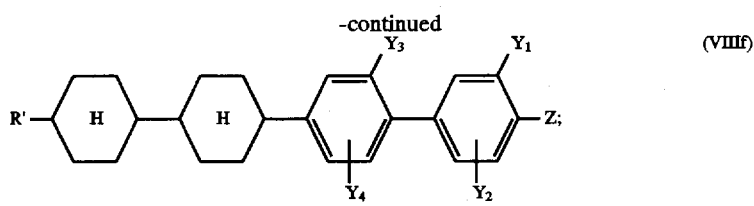

(VIIIf)

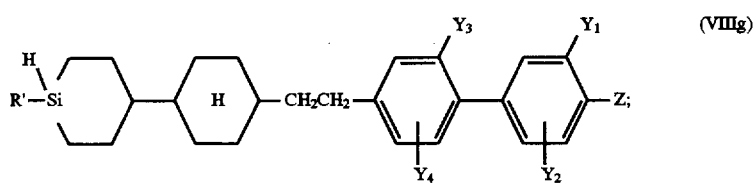

(VIIIg)

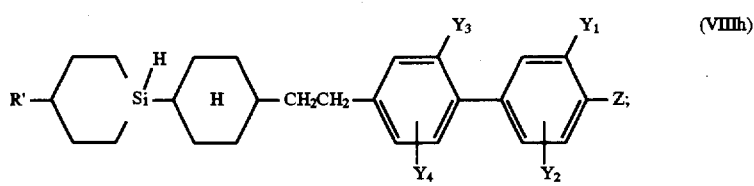

(VIIIh)

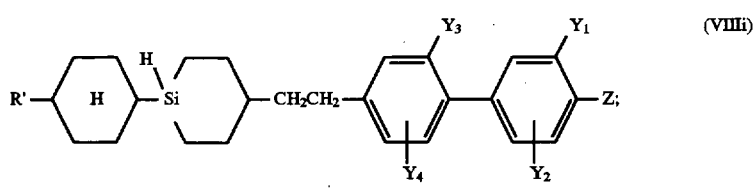

(VIIIi)

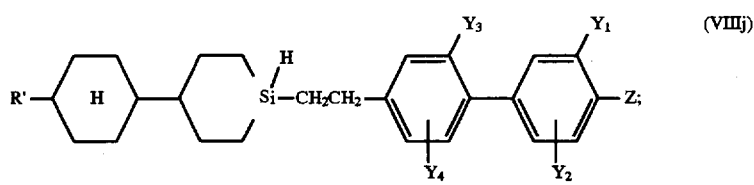

(VIIIj)

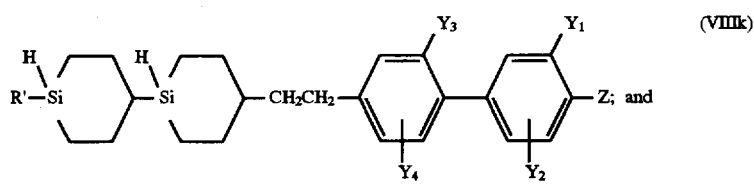

(VIIIk); and

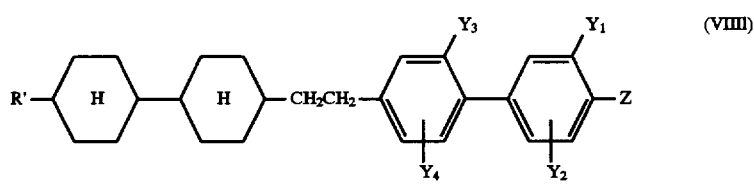

(VIIIl)

The steric arrangement and R' are, respectively, same as in the formula (II).

The moiety of the formula

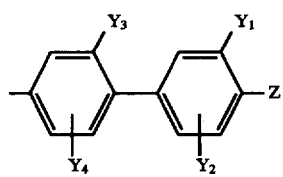

may be the same as those set out with respect to the formula (VI).

In the compounds of the general formulas (II) to (VIII), preferred groups represented by R' are as follows.

Among the linear alkyl groups having from 1 to 7 carbon atoms, ethyl, n-propyl, n-butyl, n-pentyl, n-hexyl and n-heptyl are preferred. Likewise, preferred alkoxyalkyl groups include methoxymethyl, 2-methoxyethyl, 3-methoxypropyl, 5-methoxypentyl, ethoxymethyl, 2-ethoxyethyl, (n-propoxy)methyl, and (n-pentoxy)methyl. Preferred mono or difluoroalkyl groups include 2-fluoroethyl, 2-fluoropropyl, 2-fluorobutyl, 2-fluoropentyl, 5-fluoropentyl, 6-fluorohexyl, 7-fluoroheptyl, 1,1-difluoroethyl, 2,2-difluoroethyl, 2,2-difluoropropyl, 2,2-difluorobutyl, 4,4-difluorobutyl, and 4,4-difluoropentyl. Preferred alkenyl groups include vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4E-hexenyl, 4Z-hexenyl, 4E-heptenyl, 4Z-heptenyl, 5-hexenyl, and 6-heptenyl.

Preferred moieties of the formula

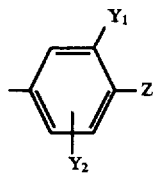

include:

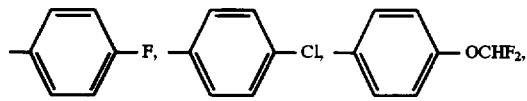

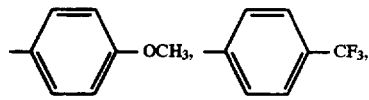

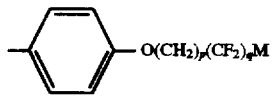

wherein p and q are, respectively 0, 1 or 2 provided that (p+q)=2, 3 or 4, and M is H, F or Cl,

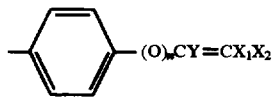

wherein n, Y, $X_1$ and $X_2$ are, respectively, as defined hereinbefore, i.e. n is 0 or 1, $X_1$ and Y, respectively, represent H, F or Cl, and $X_2$ represents F or Cl,

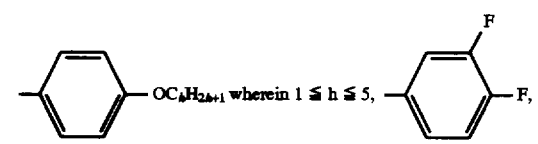

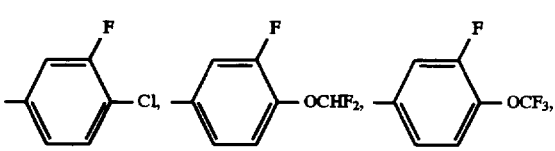

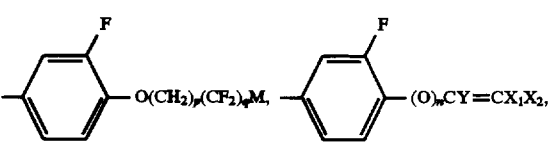

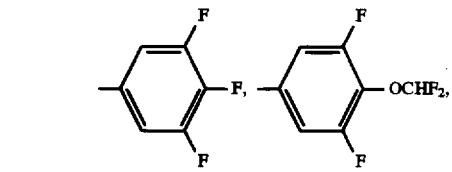

-continued

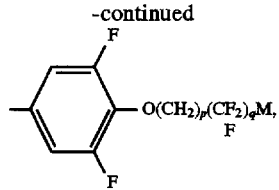

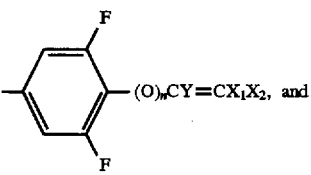

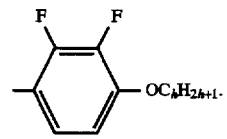

Preferred moieties of the formula

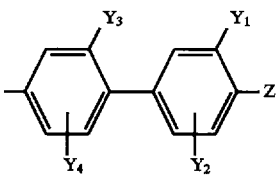

include:

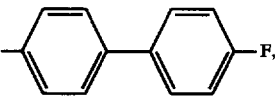

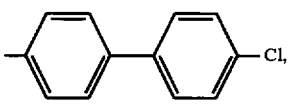

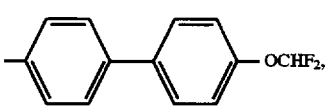

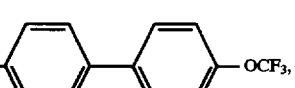

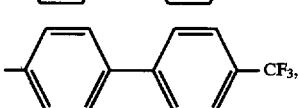

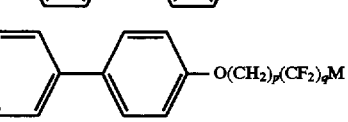

wherein p and q are, respectively, 0, 1 or 2 provided that (p+q)=2, 3 or 4, and M is H, F or Cl,

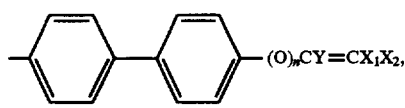
wherein n is 0 or 1, $X_1$ and Y are, respectively, H, F or Cl, and $X_2$ is F or Cl,
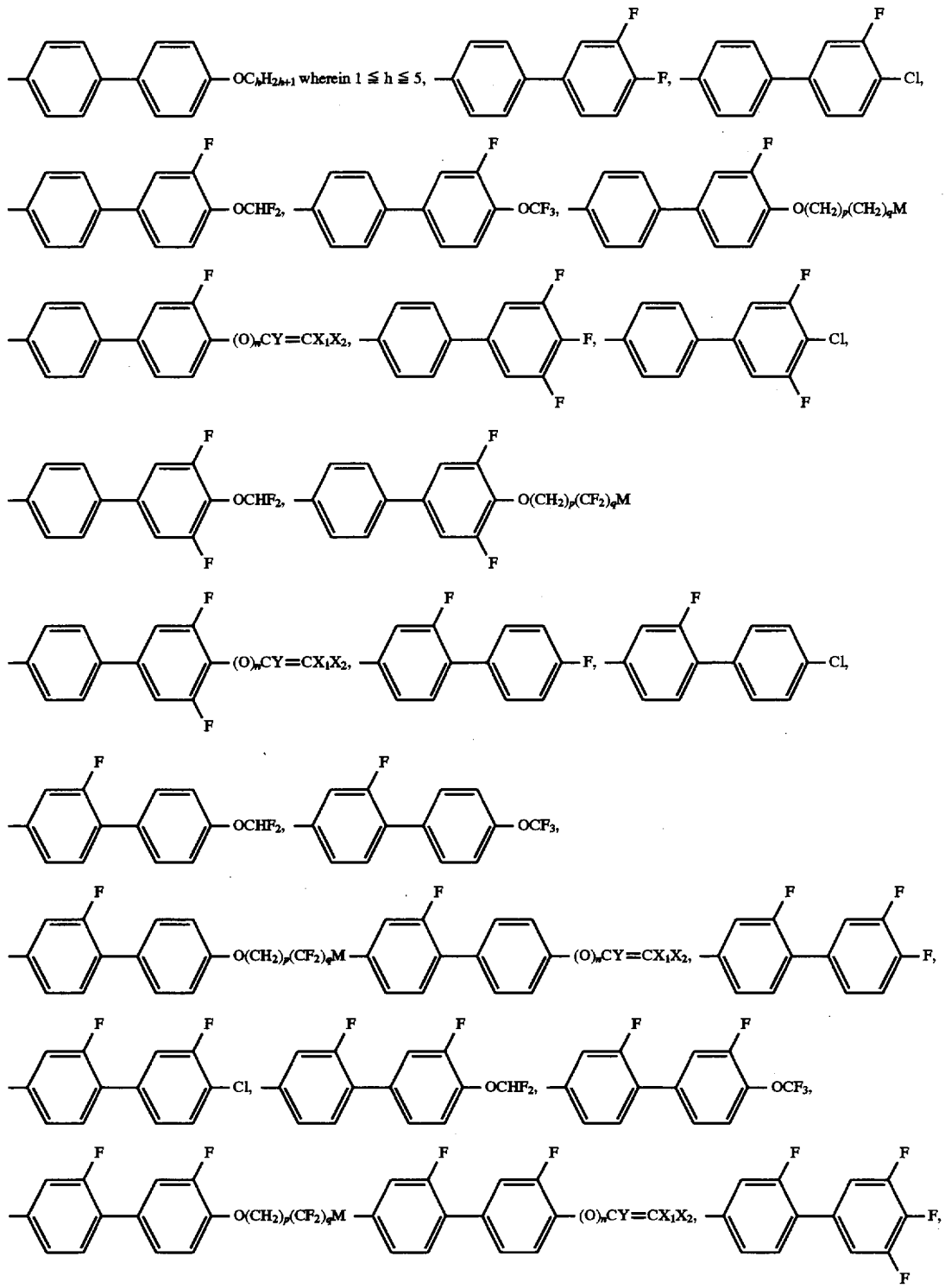

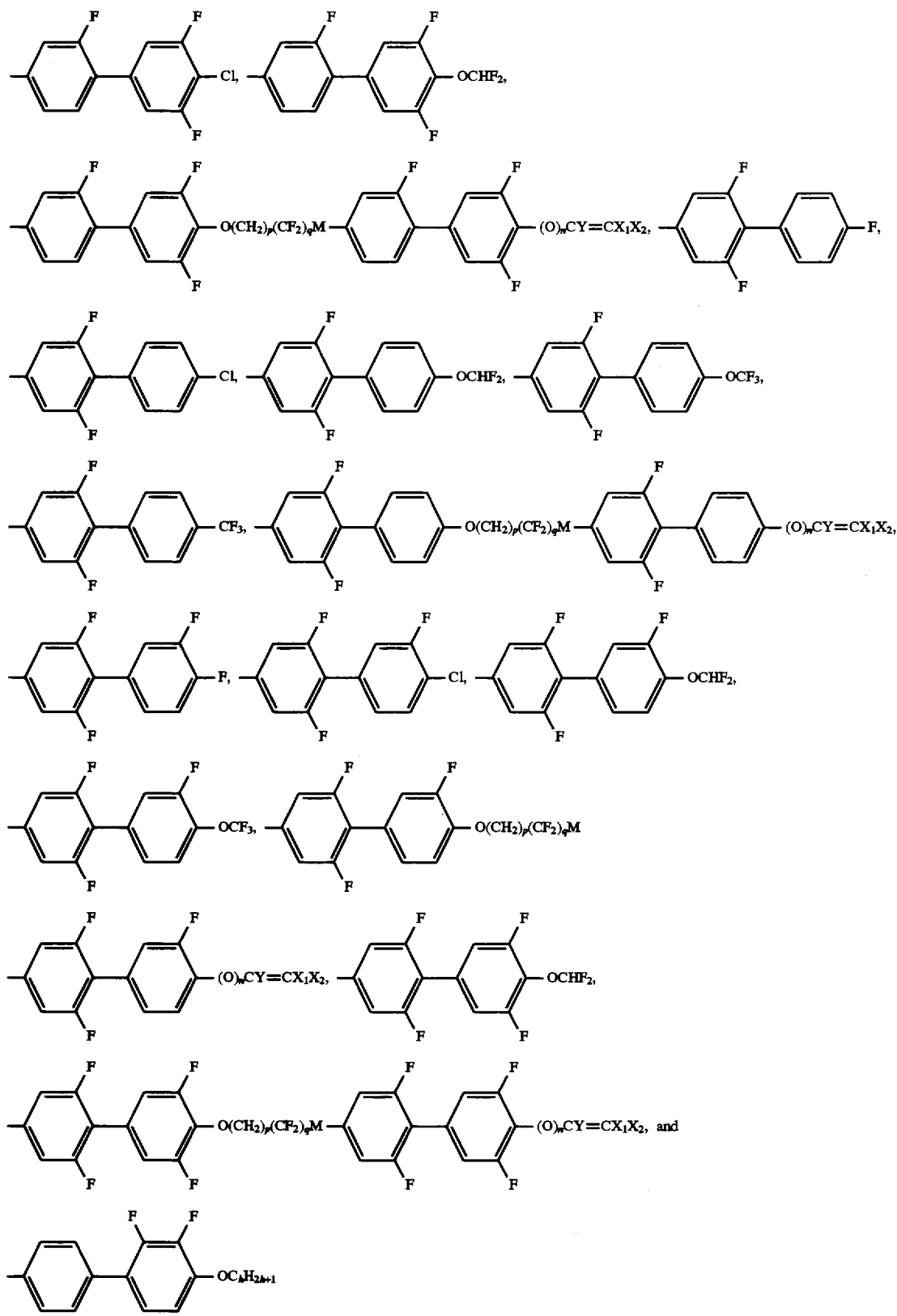

Preferred moieties of the formula

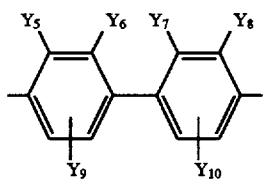

include:

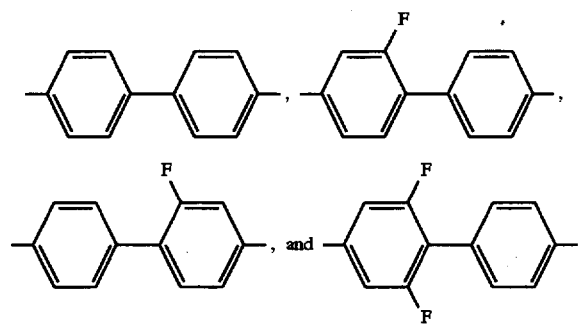

Preferred ring structures include those of the general formulas (IIa), (IIc), (IIe), (IIIa), (IIIc), (IIId), (IIIf), (IIIh), (IVa), (IVc), (IVd), (IVf), (IVh), (Vd), (Vf), (Vh), (VIa), (VIc), (VIIa), (VIId), (VIIe), (VIIf), (VIIIa), (VIIIc), (VIIIf), (VIIIg), (VIIIi), and (VIIII). This is because when applied as a liquid crystal composition, these compounds can impart a nematic liquid crystal phase over a wide working temperature, high response speed, low threshold voltage, good voltage retention and good nematic phase stability at low temperatures.

In preferred embodiments of the invention, the composition should comprise:

(a) 0 to 30 mole %, more preferably from 2 to 20 mole %, of at least one compound selected from the compounds of the general formulas ($I_1$) to ($I_9$) and (IIa) to (IIe), (IIIa) to (IIIc), and (IVa) to (IVc);

(b) 50 to 100 mole %, preferably from 70 to 96 mole %, of a mixture of at least one compound selected from the compounds of the general formulas ($I_{10}$) to ($I_{30}$), and at least one compound selected from the compounds of the formulas (IIId) to (IIIh), (IVd) to (IVh), (Va) to (Ve), and (VIa) to (VIc); and (c) 0 to 20 mole %, more preferably 2 to 15 mole %, of at least one compound selected from the compounds of the general formulas (VIIa) to (VIIf) and (VIIIa) to (VIIII).

The at least one compound selected from the compounds of the general formulas ($I_{10}$) to ($I_{30}$) should preferably be present in amounts of from 20 to 90 mole % in component (b). The component (b) may further comprise up to 30 mole % of component (a) and/or up to 20 mole % of component (c).

The use of the (a) component in excess is advantageous from the standpoint of high response speed and low threshold voltage, but an upper temperature at which the nematic phase can be stably kept lowers, thus causing a liquid crystal temperature range to become narrower. On the contrary, when the (a) component is not present or is small in amount, the response speed may lower. If the (b) component is less than the range defined above, this is disadvantageous in the establishment of a low threshold voltage.

The liquid crystal composition should preferably be composed of the (a) and (b) components. Nevertheless, in order to extend the nematic phase toward a higher temperature side, the (c) component is conveniently added to the composition. In this connection, however, the use of the (c) component in excess is not advantageous from the standpoint of the high response speed, the low threshold voltage, and the stabilization of the nematic phase at low temperatures.

In the preferred compositions of the invention, the at least one compound selected from the compounds of the general formulas ($I_9$) to ($I_{30}$) should be present in an mount of 10 mole % of the composition in minimum.

The refractive index anisotropy ($\Delta n$) which is one of physical properties relating to a panel design, e.g. a visual angle characteristic, can be controlled by addition of a compound of the general formula (IVa) or (IVb) or may be secondarily controlled by addition of a compound or compounds of the formula (Va) to (Ve) and (VIa) to (VIc). It will be noted that the above-mentioned component or components are added in small amounts for the first transmission minimum panel of Gooch and Tarry and added in excess for the second transmission minimum panel.

In recent years, the liquid crystal panels have an increasing demand. A diversity of requirements for physical properties which are necessary individually for office automation apparatus, on-vehicle devices, portable devices and the like have to be satisfied. To this end, the compounds of the general formula (I) and the compounds of the general formulas (II) to (VI) should be properly selected in optimum mounts to provide liquid crystal compositions for intended purposes.

For mixing of these compounds or components, a given mount of a minor component is initially mixed with and thermally melted in a major component. Alternatively, individual components may be separately dissolved in organic solvents such as acetone, methanol, chloroform and the like at concentrations of 1 to 10 equivalents, followed by mixing the solutions and removing the respective solvents by evaporation.

The resultant liquid crystal composition of the invention has a nematic liquid crystal phase whose working temperature ranges as widely as from a nematic phase lower limit temperature of $-20°$ C. to an upper limit temperature of $70°$ to $100°$ C. When stored over a long time at $-20°$ C., the composition does not produce any smectic phase or crystal phase. The threshold voltage is in the range of not higher than 1.6 V, especially from 1.1 to 1.5 V. The voltage retention rate has been found to be 98% or over on measurement at $100°$ C.

As a matter of course, the liquid crystal composition of the invention which is suitably employed in liquid crystal display devices may further comprise polychromatic dyes for forming a coloring guest-host system, or chiral dopants or other additives for imparting the direction and strength of twisting thereto. The additive-containing liquid crystal composition is placed between optically transparent substrates on which an active element such as TFT, MIM or the like is formed, thereby forming a liquid crystal display device as is known in the art.

If necessary, the element may have various types of undercoatings, overcoatings for controlling the alignment, a polarizer, a filter and a reflective layer as is known in the art. Alternatively, a multi-layer cell may be used to incorporate the compounds of the invention. The liquid crystal display device may be used in combination with other types of display devices, semiconductor substrates, and light sources.

The invention is more particularly described by way of examples.

EXAMPLE 1
Preparation of 4-(trans-4-n-pentyl-4-silacyclohexyl)-1-(2,2-difluorovinyl)benzene 18 g of 4-chlorophenyltrimethylsilane was dropped in a mixture of 2.5 g of magnesium and 100 ml of tetrahydrofuran (hereinafter referred to simply as THF), followed by refluxing for 3 hours to obtain a Grignard reagent. A solution of 25 g of 4-phenyl-4-pentyl-4-silacyclohexanone in 50 ml of THF was added to the reagent. After refluxing for 2 hours, the reaction mixture was cooled down to room temperature and poured into an ammonium chloride aqueous solution, followed by extraction with toluene. 1 g of p-toluenesulfonic acid was added to the toluene solution. While refluxing, water generated was removed from the solution. When the generation of water was stopped, the reaction mixture was charged into a sodium hydrogencarbonate aqueous solution, followed by washing, drying and concentration by a usual manner. The resultant residue was purified through silica gel chromatography.

The purified product was dissolved in 200 ml of ethyl acetate and hydrogenated in the presence of 0.2 g of a palladium-carbon catalyst at a pressure of 0.5 MPa. After consumption of the theoretical amount of hydrogen, the catalyst was removed by filtration, followed by concentration of the residue. 200 ml of a methylene chloride solution of 1 mol/liter of iodine monochloride was added to the resultant oily substance, followed by agitation for 1 hour. Thereafter, 20 ml of methanol and 60 ml of triethylamine were added to the solution. After agitation for 1 hour, the mixture was washed, dried and concentrated by a usual manner. The resulting concentrate was dissolved in 100 ml of THF and added to a solution of 5 g of lithium aluminium hydride in 100 ml of THF. The reaction mixture was agitated at room temperature for 3 hours, and washed, dried and concentrated by a usual manner, followed by purification of the resultant residue through silica gel chromatography to obtain 29.8 g of 4-(4-pentyl-4-silacyclohexyl)-1-iodobenzene.

26 g of the thus obtained 4-(4-pentyl-4-silacyclohexyl)-1-iodobenzene was dropped in a mixture of 2.0 g of magnesium and 100 ml of diethyl ether, followed by refluxing for 2 hours to obtain a Grignard reagent. A solution of 9.5 g of zinc chloride in 50 ml of THF was added to the reagent, followed by agitation for 30 minutes and further addition of 0.1 g of tetrakistriphenylphosphine palladium. Then, 2,2-difluoro-1-bromoethylene was bubbled in the reaction mixture. After completion of the reaction, the mixture was washed, dried and concentrated by a usual manner, followed by purification of the resultant residue through silica gel chromatography. The resultant product consisted of a mixture of steric isomers and purified by recrystallization to obtain 8.1 g of the intended compound.

The compound was subjected to measurement of phase transition temperatures and IR analysis. The results are shown below.

Crystal-isotactic phase transition temperature: 4.3° C.
Nematic-isotactic phase transition temperature: 23.6° C.
IR (KBr, disc), $v_{max}$: 2920, 2856, 2100, 1730, 1408, 1248, 1186, 1167, 985, 939, 885, 833 cm$^{-1}$

EXAMPLE 2
Preparation of 4-(trans-4-n-pentyl-4-silacyclohexyl)-1-(1,2,2-trifluorovinyl)benzene The general procedure of Example 1 was repeated using 1,2,2-trifluoro-2-bromoethylene instead of 2,2-difluoro-1-bromoethylene, thereby obtaining the intended compound.

EXAMPLE 3
Preparation of 4-(trans-4-n-pentyl-4-silacyclohexyl)-2,6-difluoro-1-(1-fluoro-2-chlorovinyl)benzene The general procedure of Example 1 was repeated using 1-bromo-2-chloro-1-fluoroethylene instead of 2,2-difluoro-1-bromoethylene and 4-chloro-2,6-difluorophenyltrimethylsilane instead of 4-chlorophenyltrimethylsilane, thereby obtaining the intended compound.

EXAMPLE 4
Preparation of 4-(trans-4-n-pentyl-4-silacyclohexyl)-1-(1,2-difluorovinyl)benzene The general procedure of Example 1 was repeated using 1-bromo-1,2-difluoroethylene instead of 2,2-difluoro-1-bromoethylene, thereby obtaining the intended compound.

EXAMPLE 5
Preparation of 4-(trans-4-n-pentyl-4-silacyclohexyl)-2,6-difluoro-1-(1,2-difluorovinyl)benzene The general procedure of Example 4 was repeated using 4-chloro-2,6-difluorophenyltrimethylsilane instead of 4-chlorophenyltrimethylsilane, thereby obtaining the intended compound.

EXAMPLE 6
Preparation of 4-(trans-4-n-pentyl-4-silacyclohexyl)-1-(1-fluoro-2-chlorovinyl)benzene The general procedure of Example 3 was repeated using 4-chlorophenyltrimethylsilane instead of 4-chloro-2,6-difluorophenyltrimethylsilane, thereby obtaining the intended compound.

EXAMPLE 7
Preparation of 4-(trans-4-n-pentyl-4-silacyclohexyl)-1-(2,2-dichlorovinyl)benzene The general procedure of Example 1 was repeated using 2-bromo-1,1-dichloroethylene instead of 2,2-difluoro-1-bromoethylene, thereby obtaining the intended compound.

The compound had the following phase transition temperatures with the results of IR analysis.

Crystal-isotactic phase transition temperature: 17.6° C.
Nematic-isotactic phase transition temperature: 39.7° C.
IR (KBr, disc), $v_{max}$: 2918, 2852, 2100, 1659, 1408, 1088, 987, 912, 887, 829 cm$^{-1}$

EXAMPLE 8
Preparation of 4-(trans-4-n-heptyl-4-silacyclohexyl)-1-(2,2-difluorovinyl)benzene The general procedure of Example 1 was repeated using 4-phenyl-4-heptyl-4-silacyclohexanone instead of 4-phenyl-4-pentyl-4-silacyclohexanone, thereby obtaining the intended compound.

EXAMPLE 9
Preparation of 4-(trans-4-(5-methoxy-n-pentyl)-4-silacyclohexyl)-1-(1,2-difluorovinyl)benzene The general procedure of Example 1 was repeated using 4-phenyl-4-(5-methoxypentyl)4-silacyclohexanone instead of 4-phenyl-4-pentyl-4-silacyclohexanone, thereby obtaining the intended compound.

EXAMPLE 10
Preparation of 4-(2-(trans-4-n-heptyl-4-silacyclohexyl)ethyl)-1-(1,2-difluorovinyl)benzene 12 g of potassium t-butoxide was added to a mixture of 35 g of methoxymethyltriphenylphosphonium chloride and 200 ml of THF to prepare an orange ylide solution. A solution of 28 g of 4-n-heptyl-4-phenyl-4-silacyclohexanone in 50 ml of THF was added to the solution. After agitation for 2 hours at room temperature, the mixture was poured into iced water and extracted with methylene chloride. The extract was washed, dried and concentrated by a usual manner. n-Hexane was added to the resultant concentrate, followed by removal of the resultant triphenylphosphine oxide crystals by filtration. The resultant filtrate was concentrated. The concentrate was hydrolyzed with 100 ml of 20% hydrochloric acid, followed by washing, drying and concentration by a usual manner to obtain 4-n-heptyl-4-phenyl-4-silacyclohexane carbaldehyde.

The carbaldehyde was added to 200 ml of an aqueous THF solution of 5 g of sodium borohydride and 1 g of sodium hydroxide and agitated for 1 hour, followed by washing, drying and concentration by a usual manner. The resultant alcohol was dropped in a methylene chloride solution of 10 g of phosphorus tribromide and 10 g of pyridine to obtain 4-bromomethyl-1-n-heptyl-1-phenyl-1-silacyclohexane.

Subsequently, 25 g of the thus obtained compound was dropped in a mixture of 2 g of magnesium and 100 ml of THF, followed by refluxing for 3 hours to obtain a Grignard reagent. The reagent was added to a solution, in 50 ml of THF, of 0.2 g of triethyl phosphite, 0.1 g of copper (0) iodide and 16.3 g of 4-bromomethyl-1-(1,2-difluorovinyl)benzene. After refluxing for 2 hours, the reaction mixture was cooled down to room temperature and poured into an ammonium chloride aqueous solution, followed by washing, drying and concentration by a usual manner. 70 ml of a methylene chloride solution of 1 mol/liter of iodine monochloride was added to the resultant oily substance and agitated for 1 hour. Subsequently, 20 ml of methanol and 60 ml of triethylamine were added to the solution. After agitation for 1 hour, the mixture was washed, dried and concentrated by a usual manner. The resultant concentrate was dissolved in 100 ml of THF and added to a solution of 5 g of lithium aluminium hydride in 100 ml of THF. The reaction mixture was agitated at room temperature for 3 hours, and washed, dried and concentrated by a usual manner, followed by purification through silica gel chromatography. The resultant product consisted of a mixture of steric isomers and purified by recrystallization to obtain 10 g of the intended compound.

EXAMPLE 11

Preparation of 4-(2-(trans-4-n-pentyl-4-silacyclohexyl) ethyl)-1-(2,2-difluorovinyl)benzene The general procedure of Example 10 was repeated using 4-phenyl-4-pentyl-4-silacyclohexanone instead of 4-phenyl-4-heptyl-4-silacyclohexanone and 4-bromomethyl-1-(2,2-difluorovinyl)benzene instead of 4-bromomethyl-1-(1,2-difluorovinyl)benzene, thereby obtaining the intended compound.

EXAMPLE 12

Preparation of 4-(2-(trans-4-n-pentyl-4-silacyclohexyl) ethyl)-1-(2,2-difluorovinyloxy)benzene The general procedure of Example 11 was repeated using 4-bromomethylphenyl-2,2-difluorovinyl ether instead of 4-bromomethyl-1-(2,2-difluorovinyl)benzene, thereby obtaining the intended compound.

EXAMPLE 13

Preparation of 4-(2-(trans-4-n-heptyl-4-silacyclohexyl) ethyl)-2,6-difluoro-1-(1,2-difluorovinyl)benzene The general procedure of Example 10 was repeated using 4-bromomethyl-2,6-difluoro-1-(1,2-difluorovinyl)benzene instead of 4-bromomethyl-1-(1,2-difluorovinyl)benzene, thereby obtaining the intended compound.

EXAMPLE 14

Preparation of 4-(2-(trans-4-(4-pentenyl)-4-silacyclohexyl) ethyl)-1-(1,2,2-trifluorovinyl)benzene The general procedure of Example 10 was repeated using 4-phenyl-4-(4-pentenyl)-4-silacyclohexanone instead of 4-phenyl-4-n-heptyl-4-silacyclohexanone and 4-bromomethyl-1-(1,2,2-trifluorovinyl)benzene instead of 4-bromomethyl-1-(1,2-difluorovinyl)benzene, thereby obtaining the intended compound.

EXAMPLE 15

Preparation of 4'-(2-(trans-4-n-propyl-4-silacyclohexyl) ethyl)-3,5-difluoro-4-(2,2-difluorovinyloxy)biphenyl The general procedure of Example 10 was repeated using 4-phenyl-4-propyl-4-silacyclohexanone instead of 4-phenyl-4-heptyl-4-silacyclohexanone and 4-bromomethyl-3',5'-difluoro-4'-(2,2-difluorovinyloxy) biphenyl instead of 4-bromomethyl-1-(1,2-difluorovinyl) benzene, thereby obtaining the intended compound.

EXAMPLE 16

Preparation of 4'-(2-(trans-4-n-pentyl-4-silacyclohexyl) ethyl)-3,5-difluoro-4-(1,2-difluorovinyl)biphenyl The general procedure of Example 10 was repeated using 4-phenyl-4-pentyl-4-silacyclohexanone instead of 4-phenyl-4-heptyl-4-silacyclohexanone and 4-bromomethyl-3',5'-difluoro-4'-(1,2-difluorovinyl)biphenyl instead of 4-bromomethyl-1-(1,2-difluorovinyl)benzene, thereby obtaining the intended compound.

EXAMPLE 17

Preparation of 4'-(2-(trans-4-n-propyl-4-silacyclohexyl) ethyl)-2',3,5-trifluoro-4-(1,2-difluorovinyl)biphenyl The general procedure of Example 15 was repeated using 4-bromomethyl-2,3',5'-trifluoro-4'-(1,2-difluorovinyl) biphenyl instead of 4-bromomethyl-3',5'-difluoro-4'-(2,2-difluorovinyloxy)biphenyl, thereby obtaining the intended compound.

EXAMPLE 18

Preparation of trans-4-(trans-4-n-pentyl-4-silacyclohexyl)-1-(1,2-difluorovinyl)cyclohexane A solution of 40 g of 4-(4-n-pentyl-4-phenyl-4-silacyclohexyl)cyclohexanone in 50 ml of THF was added to 200 ml of an aqueous THF solution of 4 g of sodium borohydride and 1 g of sodium hydroxide and agitated for 1 hour, followed by washing, drying and concentration by a usual manner. The resultant alcohol was dropped in a methylene chloride solution of 10 g of phosphorus trichloride and 10 g of pyridine to obtain 4-(4-n-pentyl-4-phenyl-4-silacyclohexyl)cyclohexyl bromide.

Subsequently, 20 g of the thus obtained compound was dropped in a mixture of 1.5 g of magnesium and 100 ml of THF and refluxed for 3 hours to obtain a Grignard reagent. The reagent is added to a solution, in 50 ml of THF, of 0.2 g of triethyl phosphite, 0.1 g of copper (0) iodide and 15 g of 1-bromo-1,1,2-trifluoroethane. After refluxing for 2 hours, the reaction mixture was cooled down to room temperature and charged into an aqueous ammonium chloride solution, and was washed, dried and concentrated by a usual manner.

12 g of potassium tert-butoxide was added to the concentrate and refluxed in 100 ml of t-butyl alcohol for 5 hours. The reaction mixture was cooled down to room temperature and charged into an aqueous ammonium chloride solution, followed by washing, drying and concentration by a usual manner. 40 ml of a methylene chloride solution of 1 mol/liter of iodine monochloride was added to the resultant oily substance and agitated for 1 hour. 20 ml of methanol and 60 ml of triethylamine were added to the solution. After agitation for 1 hour, the resultant concentrate was dissolved in 100 ml of THF and added to a solution of 5 g of lithium aluminium hydride in 100 ml of THF. The reaction mixture was agitated at room temperature for 3 hours, followed by washing, drying and concentration by a usual manner. The residue was purified through silica gel chromatography. The purified substance consisted of a mixture of steric isomers and was purified by recrystallization to obtain 7.1 g of the intended product.

EXAMPLE 19

Preparation of trans-4-(trans-4-n-pentyl-4-silacyclohexyl)-1-(2,2-difluorovinyl)cyclohexane The general procedure of Example 18 was repeated using 2-bromo-1,1,1-trifluoroethane instead of 1-bromo-1,1,2-trifluoroethane, thereby obtaining the intended compound.

EXAMPLE 20

Preparation of trans-4-(trans-4-n-heptyl-4-silacyclohexyl-1-(1,2,2-trifluorovinyl)cyclohexane The general procedure of Example 18 was repeated using 4-(4-heptyl-4-phenyl-4-silacyclohexyl)cyclohexanone instead of 4-(4-pentyl-4-phenyl-4-silacyclohexyl)cyclohexanone and 2-bromo-1,1,1,2-tetrafluoroethane instead of 1-bromo-1,1,2-trifluoroethane, thereby obtaining the intended compound.

EXAMPLE 21

Preparation of 4-(trans-4-(trans-4-n-pentyl-4-silacyclohexyl)cyclohexyl)-2,6-difluoro-1-(2,2-difluorovinyloxy)benzene 35 g of 4-bromo-2,6-difluoro-1-(t-butyldimethylsiloxy)benzene was dropped in a mixture of 2.5 g of magnesium and 100 ml of THF and refluxed for 3 hours to obtain a Grignard reagent. An aqueous solution of 33 g of 4-(4-n-pentyl-4-phenyl-4-silacyclohexyl)cyclohexanone in 50 ml of THF was added to the reagent. After refluxing for 2 hours, the reaction mixture was cooled down to room temperature and charged into an aqueous ammonium chloride solution, followed by extraction with toluene. 1 g of p-toluenesulfonic acid was added to the resultant toluene solution, after which while refluxing, water being generated was removed. At the time when any water was not distilled off, the reaction mixture was charged into an aqueous sodium hydrogencarbonate solution, followed by washing, drying and concentration by a usual manner. The resultant residue was purified through silica gel chromatography.

The purified substance was dissolved in 200 ml of ethyl acetate and hydrogenated in the presence of 0.2 g of a palladium-carbon catalyst at 0.5 MPa. After it was confirmed that hydrogen was consumed theoretically, the catalyst was removed by filtration, and the filtrate was concentrated. The resultant concentrate was added to 100 ml of a THF solution of 1 mol/liter of tetrabutylammonium fluoride and agitated for 1 hour. The reaction mixture was poured into 100 ml of 20% hydrochloric acid, and washed, dried and concentrated by a usual manner. The resultant residue was purified through silica gel chromatography.

25 g of the resultant phenol and 100 ml of THF were added to a mixture of 1.5 g of sodium hydride and 50 ml of THF and agitated for 1 hour. Subsequently, a solution of 15 g of 1-bromo-2,2,2-trifluoroethane and 50 g of hexamethylphosphorus triamide was added to the mixture and agitated at 60° C. for 5 hours, followed by washing, drying and concentration by a usual manner. 10 g of potassium t-butoxide was added to the resultant residue and refluxed in 100 ml of t-butyl alcohol for 5 hours. The reaction mixture was cooled down to room temperature and charged into an aqueous ammonium chloride solution, followed by washing, drying and concentration by a usual manner.

40 ml of a methylene chloride solution of 1 mol/liter of iodine monochloride was added to the resultant oily substance and agitated for 1 hour. Thereafter, 20 ml of methanol and 60 ml of triethylamine were added to the mixture. After agitation for 1 hour, the mixture was washed, dried and concentrated by a usual manner. The resultant residue was dissolved in 100 ml of THF and added to a solution of 5 g of lithium aluminium hydride in 100 ml of THF. The reaction mixture was agitated at room temperature for 3 hours, followed by washing, drying and concentration by a usual manner. The resultant residue was purified through silica gel chromatography. The pitied substance consisted of a mixture of steric isomers and purified by recrystallization to obtain 9.5 g of the intended compound.

EXAMPLE 22

Preparation of 4-(trans-4-n-pentyl-4-silacyclohexyl)-1-(2,2-difluorovinyloxy)benzene The general procedure of Example 21 was repeated using 4-pentyl-4-phenyl-4-silacyclohexanone instead of 4-(4-pentyl-4-phenyl-4-silacyclohexyl)cyclohexanone and 4-bromo-1-(t-butyldimethylsiloxy)benzene instead of 4-bromo-2,6-difluoro-1-(t-butyldimethylsiloxy)benzene, thereby obtaining the intended compound. The phase transition temperature and the results of IR analysis are shown below.

Crystal-isotactic phase transition temperature: 10.6° C.

IR (liquid film), $v_{max}$: 2920, 2852, 2100, 1768, 1508, 1348, 1248, 1178 987, 933, 887, 818 cm$^{-1}$

EXAMPLE 23

Preparation of 4-(trans-4-(trans-4-n-pentyl-4-silacyclohexyl)cyclohexyl)-1-(1,2,2-trifluorovinyloxy)benzene The general procedure of Example 21 was repeated using 4-bromo-1-(t-butyldimethylsiloxy)benzene instead of 4-bromo-2,6-difluoro-1-(t-butyldimethylsiloxy)benzene and 2-bromo-1,1,1,2-tetrafluoroethane instead of 2-bromo-1,1,1-trifluoroethane, thereby obtaining the intended compound.

EXAMPLE 24

Preparation of 4-(trans-4-(trans-4-n-propyl-4-silacyclohexyl)cyclohexyl)-2,6-difluoro-1-(1,2,2-trifluorovinyl)benzene The general procedure of Example 2 was repeated using 4-(4-propyl-4-phenyl-4-silacyclohexyl)cyclohexanone instead of 4-pentyl-4-phenyl-4-silacyclohexanone and 4-bromo-2,6-difluoro-1-triethylsilylbenzene instead of 4-chloro-1-(trimethylsilyl)benzene, thereby obtaining the intended compound.

EXAMPLE 25

Preparation of 4-(trans-4-(trans-4-n-propyl-4-silacyclohexyl)cyclohexyl)-1-(1-fluoro-2-chlorovinyl)benzene The general procedure of Example 3 was repeated using 4-(4-propyl-4-phenyl-4-silacyclohexyl)cyclohexanone instead of 4-pentyl-4-phenyl-4-silacyclohexanone and 4-bromo-1-(trimethylsilyl)benzene instead of 4-chloro-2,6-difluoro-1-(trimethylsilyl)benzene, thereby obtaining the intended compound.

EXAMPLE 26
Preparation of 4-(trans-4-(trans-4-n-propyl-4-silacyclohexyl)cyclohexyl)-2,6-difluoro-1-(1-fluoro-2-chlorovinyl)benzene The general procedure of Example 25 was repeated using 4-bromo-2,6-difluoro-1-(trimethylsilyl)benzene instead of 4-bromo-1-(trimethylsilyl)benzene, thereby obtaining the intended compound.

EXAMPLE 27
Preparation of 4-(trans-4-(trans-4-n-pentyl-4-silacyclohexyl)cyclohexyl)-2,6-difluoro-1-(2,2-difluorovinyl)benzene The general procedure of Example 26 was repeated using 1,1-difluoro-2-bromoethylene instead of 1-bromo-2-chloro-1-fluoroethylene and 4-(4-pentyl-4-phenyl-4-silacyclohexyl)cyclohexanone instead of 4-(4-propyl-4-phenyl-4-silacyclohexyl)cyclohexanone, thereby obtaining the intended compound.

EXAMPLE 28
Preparation of 4-(trans-4-(trans-4-n-propyl-4-silacyclohexyl)cyclohexyl)-1-(1-fluoro-2,2-dichlorovinyl)benzene The general procedure of Example 25 was repeated using 1-bromo-2,2-dichloro-1-fluoroethylene instead of 1-bromo-2-chloro-1-fluoroethylene, thereby obtaining the intended compound.

EXAMPLE 29
Preparation of 4-(trans-4-(trans-4-(4-pentenyl)-4-silacyclohexyl)cyclohexyl)-2,6-difluoro-1-(1,2,2-trifluorovinyl)benzene The general procedure of Example 24 was repeated using 4-(4-(4-pentenyl)-4-phenyl-4-silacyclohexyl)cyclohexanone instead of 4-(4-propyl-4-phenyl-4-silacyclohexyl)cyclohexane, thereby obtaining the intended compound.

EXAMPLE 30
Preparation of 4-(trans-4-(trans-4-(5-methoxy-n-pentyl)-4-silacyclohexyl)cyclohexyl)-2,6-difluoro-1-(2,2-difluorovinyloxy)benzene The general procedure of Example 21 was repeated using 4-(4-(5-methoxypentyl)-4-phenyl-4-silacyclohexyl)cyclohexanone instead of 4-(4-pentyl-4-phenyl-4-silacyclohexyl)cyclohexanone, thereby obtaining the intended compound.

EXAMPLE 31
Preparation of 4-(trans-4-(trans-4-(4-fluoro-n-butyl)-4-silacyclohexyl)cyclohexyl)-2,6-difluoro-1-(1,2,2-trifluorovinyloxy)benzene The general procedure of Example 21 was repeated using 4-(4-(4-fluorobutyl)-4-phenyl-4-silacyclohexyl)cyclohexanone instead of 4-(4-pentyl-4-phenyl-4-silacyclohexyl)cyclohexanone and 2-bromo-1,1,1,2-tetrafluoroethane instead of 1-bromo-2,2,2-trifluoroethane, thereby obtaining the intended compound.

EXAMPLE 32
Preparation of 4-(trans-4-(trans-4-methyl-4-n-pentyl-4-silacyclohexyl)cyclohexyl)-2-fluoro-1-(1,2-difluorovinyl)benzene The general procedure of Example 28 was repeated using 4-(4-pentyl-4-methyl-4-silacyclohexyl)cyclohexanone instead of 4-(4-propyl-4-phenyl-4-silacyclohexyl) cyclohexanone, 1-bromo-1,2-difluoroethylene instead of 1-bromo-2,2-dichloro-1-fluoroethylene, and 4-bromo-2-fluoro-1-(trimethylsilyl)benzene instead of 4-bromo-1-(trimethylsilyl)benzene, thereby obtaining the intended compound.

EXAMPLE 33
Preparation of 4-(trans-4-(trans-4-n-pentylcyclohexyl)-4-silacyclohexyl)-2,6-difluoro-1-(1,2,2-trifluorovinyloxy) benzene The general procedure of Example 23 was repeated using 4-(4-pentylcyclohexyl)-4-phenyl-4-silacyclohexanone instead of 4-(4-pentyl-4-phenyl-4-silacyclohexyl) cyclohexanone and 4-bromo-2,6-difluoro-1-(t-butyldimethylsiloxy)benzene instead of 4-bromo-1-(t-butyldimethylsiloxy)benzene, thereby obtaining the intended compound.

EXAMPLE 34
Preparation of 4-(trans-4-(trans-4-n-propylcyclohexyl)-4-fluoro-4-silacyclohexyl)-1-(1,2-difluorovinyl)benzene

EXAMPLE 35
Preparation of 4'-(trans-4-n-pentyl-4-silacyclohexyl)-3,5-difluoro-1-(2,2-difluorovinyloxy)biphenyl 19 g of 4-chlorophenyltrimethylsilane was dropped in a mixture of 2.5 g of magnesium and 100 ml of THF and refluxed for 3 hours to obtain a Grignard reagent. A solution of 25 g of 4-phenyl-4-pentyl-4-silacyclohexane in 50 ml of THF was added to the reagent. After refluxing for 2 hours, the reaction mixture was cooled down to room temperature and charged into an aqueous ammonium chloride solution, followed by extraction with toluene. 1 g of p-toluenesulfonic acid was added to the toluene solution, after which water being generated was removed while refluxing. When the generation of water stopped, the reaction mixture was poured into an aqueous sodium hydrogencarbonate solution, and washed, dried and concentrated by a usual manner. The resultant residue was purified through silica gel chromatography.

The purified substance was dissolved in 200 ml of ethyl acetate and hydrogenated in the presence of catalyst consisting of 0.2 g of palladium-carbon at 0.5 MPa. 200 ml of a methylene chloride solution of 1 mol/liter of bromine was added to the resultant oily substance and agitated for 1 hour. Subsequently, 200 ml of methanol and 60 ml of triethylamine were added to the solution. After agitation for 1 hour, the mixture was washed, dried and concentrated by a usual manner. The resultant concentrate was dissolved in 100 ml of THF and added to a solution of 5 g of lithium aluminium hydride in 100 ml of THF. The reaction mixture was agitated at room temperature for 3 hours, and washed, dried and concentrated, followed by purification through silica gel chromatography to obtain 23 g of 4-(4-pentyl-4-silacyclohexyl)-1-bromobenzene.

20 g of the thus obtained bromobenzene was dropped in a mixture of 1.5 g of magnesium and 100 ml of THF and refluxed for 3 hours to obtain a Grignard reagent. A solution of 8.5 g of zinc chloride in 50 ml of THF was added to the reagent and agitated for 30 minutes. The mixture was then added to a THF solution of 0.1 g of tetrakistriphenylphosphine palladium and 17 g of 4-bromo-2,6-difluoro-(2,2-difluorovinyloxy)benzene. After completion of the reaction, the mixture was washed, dried and concentrated by a usual manner, and the residue was purified through silica gel chromatography. The resultant product consisted of a mixture of steric isomers and was purified by recrystallization to obtain 11 g of the intended compound.

EXAMPLE 36

Preparation of 4'-(trans-4-n-pentyl-4-silacyclohexyl)-2',3,5-trifluoro-4-(1,2,2-trifluorovinyl)biphenyl The general procedure of Example 35 was repeated using 4-chloro-2-fluorophenyltrimethylsilane instead of 4-chlorophenyltrimethylsilane and 4-bromo-2,6-difluoro-1-(1,2,2-trifluorovinyl)benzene instead of 4-bromo-2,6-difluoro-1-(2,2-difluorovinyloxy)benzene, thereby obtaining the intended compound.

EXAMPLE 37

Preparation of 4'-(trans-4-n-propyl-4-silacyclohexyl)-2',6',3,5-tetrafluoro-4-(1,2-difluorovinyl)biphenyl The general procedure of Example 35 was repeated using 4-propyl-4-phenyl-4-silacyclohexanone instead of 4-pentyl-4-phenyl-4-silacyclohexanone, 4-chloro-2,6-difluorophenyltrimethylsilane instead of 4-chlorophenyltrimethylsilane, and 4-bromo-2,6-difluoro-1-(1,2-difluorovinyl)benzene instead of 4-bromo-2,6-difluoro-1-(2,2-difluorovinyloxy)benzene, thereby obtaining the intended compound.

EXAMPLE 38

Preparation of 4'-(trans-4-n-propyl-4-silacyclohexyl)-4-(1,2-dichlorovinyl)biphenyl The general procedure of Example 35 was repeated using 4-propyl-4-phenyl-4-silacyclohexanone instead of 4-pentyl-4-phenyl-4-silacyclohexanone, and 4-bromo-2,6-difluoro-1-(1,2-dichlorovinyl)benzene instead of 4-bromo-2,6-difluoro-1-(2,2-difluorovinyloxy)benzene, thereby obtaining the intended compound.

EXAMPLE 39

Preparation of 4'-(trans-4-n-pentyl-4-silacyclohexyl)-2',3,5-trifluoro-4-(2,2-difluorovinyl)biphenyl The general procedure of Example 36 was repeated using 4-bromo-2,6-difluoro-1-(2,2-difluorovinyl)benzene instead of 4-bromo-2,6-difluoro-1-(1,2,2-trifluorovinyl)benzene, thereby obtaining the intended compound.

EXAMPLE 40

Preparation of 4'-(trans-4-n-propyl-4-silacyclohexyl)-2',3-difluoro-4-(1,2,2-trifluorovinyloxy)biphenyl The general procedure of Example 36 was repeated using 4-propyl-4-phenyl-4-silacyclohexanone instead of 4-pentyl-4-phenyl-4-silacyclohexanone and 4-bromo-2-fluoro-1-(1,2,2-trifluorovinyloxy)benzene instead of 4-bromo-2,6-difluoro-1-(1,2,2-trifluorovinyl)benzene, thereby obtaining the intended compound.

EXAMPLE 41

Preparation of 4'-(trans-4-(3-methyl-n-butyl)-4-silacyclohexyl)-4-(1,2-difluorovinyl)biphenyl The general procedure of Example 35 was repeated using 4-(3-methylbutyl)-4-phenyl-4-silacyclohexanone instead of 4-pentyl-4-phenyl-4-silacyclohexanone and 4-bromo-1-(1,2-difluorovinyl)benzene instead of 4-bromo-2,6-difluoro-1-(2,2-difluorovinyloxy)benzene, thereby obtaining the intended compound.

EXAMPLE 42

Preparation of 4'-(trans-4-(4-fluoro-n-pentyl)-4-silacyclohexyl)-3,5-difluoro-4-(2,2-difluorovinyloxy)biphenyl The general procedure of Example 35 was repeated using 4-(4-fluoropentyl)-4-phenyl-4-silacyclohexanone instead of 4-pentyl-4-phenyl-4-silacyclohexanone, thereby obtaining the intended compound.

EXAMPLE 43

Preparation of 4'-(trans-4-(5-methoxy-n-pentyl)-4-silacyclohexyl)-2',6',3-trifluoro-4-(1,2-difluorovinyl)biphenyl The general procedure of Example 37 was repeated using 4-(5-methoxypentyl)-4-phenyl-4-silacyclohexanone instead of 4-propyl-4-phenyl-4-silacyclohexanone, and 4-bromo-2-fluoro-1-(1,2-difluorovinyl)benzene instead of 4-bromo-2,6-difluoro-1-(1,2-difluorovinyl)benzene, thereby obtaining the intended compound.

EXAMPLE 44

Preparation of 4'-(trans-4-methyl-4-n-propyl-4-silacyclohexyl)-4-(1,2-difluorovinyl)biphenyl The general procedure of Example 35 was repeated using 4-propyl-4-methyl-4-silacyclohexanone instead of 4-pentyl-4-phenyl-4-silacyclohexanone, and 4-bromo-1-(1,2-difluorovinyl)benzene instead of 4-bromo-2,6-difluoro-1-(2,2-difluorovinyloxy)benzene, thereby obtaining the intended compound.

EXAMPLE 45

Preparation of 4-(2-(trans-4-(trans-4-n-pentyl-4-silacyclohexyl)cyclohexyl)ethyl)-1-(1,2,2-trifluorovinyloxy)benzene 12 g of potassium t-butoxide was added to a mixture of 35 g of methoxymethyltriphenylphosphonium chloride and 200 ml of THF to prepare an orange ylide solution. A solution of 34 g of 4-(4-n-pentyl-4-phenyl-4-silacyclohexyl)cyclohexanone in 50 ml of THF was added to the ylide solution and agitated at room temperature for 2 hours. Thereafter, the mixture was poured into iced water and extracted with methylene chloride, followed by washing, drying and concentration by a usual manner. n-Hexane was added to the residue, and the resultant crystals of triphenylphosphine oxide were removed by filtration. The filtrate was concentrated, and the resultant residue was hydrolyzed with 100 ml of 20% hydrochloric acid, followed by washing, drying and concentration by a usual manner to obtain 4-(4-n-pentyl-4-phenyl-4-silacyclohexyl)cyclohexane carbaldehyde.

The carbaldehyde was added to 200 ml of an aqueous THF solution of 5 g of sodium borohydride and 1 g of sodium hydroxide and agitated for 1 hour, followed by washing, drying and concentration by a usual manner. The resultant alcohol was dropped in a methylene chloride solution of 10 g of phosphorus tribromide and 10 g of pyridine to obtain 4-(4-n-pentyl-4-phenyl-4-silacyclohexyl)-1-bromomethylcyclohexane.

25 g of the thus obtained compound was dropped in a mixture of 1.5 g of magnesium and 100 ml of THF and refluxed for 3 hours to obtain a Grignard reagent. The reagent was added to a solution of 0.2 g of triethyl phosphite, 0.1 g of copper (O) iodide and 16 g of 4-bromomethyl-1-(1,2,2-trifluorovinyloxy)benzene in 50 ml of THF. After refluxing for 2 hours, the reaction mixture was cooled down to room temperature and charged into an aqueous ammonium chloride solution, followed by washing, drying and concentration by a usual manner. 60 ml of a methylene chloride solution of 1 mol/liter of iodine monochloride was added to the resultant oily substance and agitated for 1 hour. Subsequently, 20 ml of methanol and 60 ml of triethylamine were added to the solution. After agitation for 1 hour, the mixture was washed, dried and concentrated by a usual manner. The resultant residue was dissolved in 100 ml of THF and added to a solution of 5 g of lithium aluminium hydride in 100 ml of THF. The reaction mixture was agitated at room temperature for 3 hours, and washed, dried and concentrated by a usual manner, followed by purification of the resulting residue through silica gel chromatography. The purified product consisted of a mixture of steric isomers and was purified by recrystallization to obtain 11 g of the intended compound.

EXAMPLE 46

Preparation of 4-(2-(trans-4-(trans-4-n-propyl-4-silacyclohexyl)cyclohexyl)ethyl)-2,6-difluoro-1-(1,2,2-trifluorovinyl)benzene The general procedure of Example 45 was repeated using 4-(4-propyl-4-phenyl-4-silacyclohexyl)cyclohexanone instead of 4-(4-pentyl-4-phenyl-4-silacyclohexyl)cyclohexanone, and 4-bromomethyl-2,6-difluoro-1-(1,2,2-trifluorovinyl)benzene instead of 4-bromomethyl-1-(1,2,2-trifluorovinyloxy)benzene, thereby obtaining the intended compound.

EXAMPLE 47

Preparation of 4-(2-(trans-4-(trans-4-n-propyl-4-silacyclohexyl)cyclohexyl)ethyl)-1-(1-fluoro-2-chlorovinyl)benzene The general procedure of Example 45 was repeated using 4-(4-propyl- 4-phenyl-4-silacyclohexyl)cyclohexanone instead of 4-(4-pentyl-4-phenyl-4-silacyclohexyl)cyclohexane, and 4-bromomethyl-1-(2-chloro-1-fluorovinyl)benzene instead of 4-bromomethyl-1-(1,2,2-trifluorovinyloxy)benzene, thereby obtaining the intended compound.

EXAMPLE 48

Preparation of 4-(2-(trans-4-(trans-4-n-propyl-4-silacyclohexyl)cyclohexyl)ethyl)-2,6-difluoro-1-(1-fluoro-2-chlorovinyl)benzene The general procedure of Example 45 was repeated using 4-(4-propyl-4-phenyl-4-silacyclohexyl)cyclohexanone instead of 4-(4-pentyl-4-phenyl-4-silacyclohexyl)cyclohexane, and 4-bromomethyl-2,6-difluoro-1-(2-chloro-1-fluorovinyl)benzene instead of 4-bromomethyl-1-(1,2,2-trifluorovinyloxy)benzene, thereby obtaining the intended compound.

EXAMPLE 49

Preparation of 4-(2-(trans-4-(trans-4-(4-fluoro-n-butyl)-4-silacyclohexyl)cyclohexyl)ethyl)-2-fluoro-1-(2,2-difluorovinyl)benzene The general procedure of Example 45 was repeated using 4-(4-(4-fluorobutyl)-4-phenyl-4-silacyclohexyl)cyclohexanone instead of 4-(4-pentyl-4-phenyl-4-silacyclohexyl)cyclohexane, and 4-bromomethyl-2-fluoro-1-(2,2-difluorovinyl)benzene instead of 4-bromomethyl-1-(1,2,2-trifluorovinyloxy)benzene, thereby obtaining the intended compound.

EXAMPLE 50

Preparation of 4-(2-(trans-4-(trans-4-(5-methoxy-n-pentyl)-4-silacyclohexyl)cyclohexyl)ethyl)-2,6-difluoro-1-(2,2-difluorovinyloxy)benzene The general procedure of Example 45 was repeated using 4-(4-(5-methoxypentyl)-4-phenyl-4-silacyclohexyl)cyclohexanone instead of 4-(4-pentyl-4-phenyl-4-silacyclohexyl)cyclohexane, and 4-bromomethyl-2,6-difluoro- 1-(2,2-difluorovinyloxy)benzene instead of 4-bromomethyl-1-(1,2,2-trifluorovinyloxy)benzene, thereby obtaining the intended compound.

EXAMPLE 51

Preparation of 4-(2-(trans-4-(trans-4-methyl-n-pentyl-4-silacyclohexyl)cyclohexyl)ethyl-1-(1,2-difluorovinyl)benzene The general procedure of Example 45 was repeated using 4-(4-pentyl-4-methyl-4-silacyclohexyl)cyclohexanone instead of 4-(4-pentyl-4-phenyl-4-silacyclohexyl)cyclohexane, and 4-bromomethyl-1-(1,2-difluorovinyl)benzene instead of 4-bromomethyl-1-(1,2,2-trifluorovinyloxy)benzene, thereby obtaining the intended compound.

EXAMPLE 52

Preparation of 4-(2-(trans-4-(trans-4-n-pentylcyclohexyl)-4-silacyclohexyl)ethyl)-2,6-difluoro-1-(1-fluoro-2-chlorovinyl)benzene The general procedure of Example 45 was repeated using 4-(4-pentylcyclohexyl)-4-phenyl-silacyclohexanone instead of 4-(4-pentyl-4-phenyl-4-silacyclohexyl)cyclohexane, and 4-bromomethyl-2,6-difluoro-1-(2-chloro-1-fluorovinyl)benzene instead of 4-bromomethyl-1-(1,2,2-trifluorovinyloxy)benzene, thereby obtaining the intended compound.

EXAMPLE 53

Preparation of 4-(2-(trans-4-(trans-4-(4-pentenyl)cyclohexyl)-4-methyl-4-silacyclohexyl)ethyl)-1-(2,2-difluorovinyl)benzene The general procedure of Example 45 was repeated using 4-(4-(4-pentenyl)cyclohexyl)-4-phenyl-4-silacyclohexanone instead of 4-(4-pentyl-4-phenyl-4-silacyclohexyl)cyclohexane, and 4-bromomethyl-1-(2,2-difluorovinyl)benzene instead of 4-bromomethyl-1-(1,2,2-trifluorovinyloxy)benzene, thereby obtaining the intended compound.

EXAMPLE 54

Preparation of 4-(trans-4-(2-(trans-4-n-pentyl-4-silacyclohexyl)ethyl)cyclohexyl)-2,6-difluoro-1-(2,2-difluorovinyloxy)benzene 12 g of potassium t-butoxide was added to a mixture of 35 g of methoxymethyltriphenylphosphonium chloride and 200 ml of THF to prepare an orange ylide solution. A solution of 23 g of 4-n-propyl-4-phenyl-4-silacyclohexanone in 50 ml of THF was added to the ylide solution and agitated at room temperature for 2 hours. Thereafter, the mixture was poured into iced water and extracted with methylene chloride, followed by washing, drying and concentration by a usual manner. n-Hexane was added to the residue, and the resultant crystals of triphenylphosphine oxide were removed by filtration. The filtrate was concentrated, and the resultant residue was hydrolyzed with 100 ml of 20% hydrochloric acid, followed by washing, drying and concentration by a usual manner to obtain 4-n-propyl-4-phenyl-4-silacyclohexane carbaldehyde.

The carbaldehyde was added to 200 ml of an aqueous THF solution of 5 g of sodium borohydride and 1 g of sodium hydroxide, and agitated for 1 hour, followed by washing, drying and concentration by a usual manner. The resultant alcohol was dropped in a methylene chloride solution of 10 g of phosphorus tribromide and 10 g of pyridine to obtain 4-bromomethyl-1-n-propyl-1-phenyl-1-silacyclohexane.

20 g of the thus obtained compound was dropped in a mixture of 1.5 g of magnesium and 100 ml of THF and refluxed for 3 hours to obtain a Grignard reagent. The reagent was added to a solution of 0.2 g of triethyl phosphite, 0.1 g of copper (0) iodide and 18.5 g of 4-(trans-4- bromomethylcyclohexyl)-2,6-difluoro-1-(2,2-difluorovinyloxy)benzene in 50 ml of THF. After refluxing for 2 hours, the reaction mixture was cooled down to room temperature and charged into an aqueous ammonium chloride solution, followed by washing, drying and concentration by a usual manner. 60 ml of a methylene chloride solution of 1 mol/liter of iodine monochloride was added to the resultant oily substance and agitated for 1 hour. Subsequently, 20 ml of methanol and 60 ml of triethylamine were added to the solution. After agitation for 1 hour, the mixture was washed, dried and concentrated by a usual manner. The resultant residue was dissolved in 100 ml of THF and added to a solution of 5 g of lithium aluminium hydride in 100 ml of THF. The reaction mixture was agitated at room temperature for 3 hours, and washed, dried and concentrated by a usual manner, followed by purification of the resulting residue through silica gel chromatography. The purified product consisted of a mixture of steric isomers and was purified by recrystallization to obtain 12 g of the intended compound.

EXAMPLE 55

Preparation of 4-(trans-4-(2-(trans-4-n-pentyl-4-silacyclohexyl)ethyl)cyclohexyl)-2-fluoro-1-(1,2,2-trifluorovinyl)benzene The general procedure of Example 54 was repeated using 4-pentyl-4-phenyl-4-silacyclohexanone instead of 4-propyl-4-phenyl-4-silacyclohexanone, and 4-(trans-4-bromomethylcyclohexyl)-2-fluoro-1-(1,2,2-trifluorovinyl)benzene instead of 4-(trans-4-bromomethylcyclohexyl)-2,6-difluoro-1-(2,2-difluorovinyloxy)benzene, thereby obtaining the intended compound.

EXAMPLE 56

Preparation of 4-(trans-4-(2-(trans-4-(4-fluoro-n-butyl)-4-silacyclohexyl)ethyl)cyclohexyl)-2-fluoro-1-(1,1-difluorovinyl)benzene The general procedure of Example 54 was repeated using 4-(4-fluorobutyl)-4-phenyl-4-silacyclohexanone instead of 4-propyl-4-phenyl-4-silacyclohexanone, and 4-(trans-4-bromomethylcyclohexyl)-2-fluoro-1-(1,2-difluorovinyl)benzene instead of 4-(trans-4-bromomethylcyclohexyl)-2,6-difluoro-1-(2,2-difluorovinyloxy)benzene, thereby obtaining the intended compound.

EXAMPLE 57

Preparation of 4-(trans-4-(2-(trans-4-(5-methoxy-n-pentyl)-4-silacyclohexyl)ethyl)cyclohexyl)-2,6-difluoro-1-(1,2,2-trifluorovinyloxy)benzene The general procedure of Example 54 was repeated using 4-(5-methoxypentyl)-4-phenyl-4-silacyclohexanone instead of 4-propyl-4-phenyl-4-silacyclohexanone, and 4-(trans-4-bromomethylcyclohexyl)-2,6-difluoro-1-(1,2,2-trifluorovinyloxy)benzene instead of 4-(trans-4-bromomethylcyclohexyl)-2,6-difluoro-1-(2,2-difluorovinyloxy)benzene, thereby obtaining the intended compound.

EXAMPLE 58

Preparation of 4-(trans-4-(2-(trans-4-(4-pentenyl)-4-silacyclohexyl)ethyl)cyclohexyl)-2-fluoro-1-(1-fluoro-2-chlorovinyl)benzene The general procedure of Example 54 was repeated using 4-(4-pentenyl)-4-phenyl-4-silacyclohexanone instead of 4-propyl-4-phenyl-4-silacyclohexanone, and 4-(trans-4-bromomethylcyclohexyl)-2-fluoro-1-(2-chloro-1-fluorovinyl)benzene instead of 4-(trans-4-bromomethylcyclohexyl)-2,6-difluoro-1-(2,2-difluorovinyloxy)benzene, thereby obtaining the intended compound.

EXAMPLE 59

Preparation of 4-(trans-4-(2-(trans-4-methyl-4-n-pentyl-4-silacyclohexyl)ethyl)cyclohexyl)-1-(2,2-difluorovinyl)benzene The general procedure of Example 54 was repeated using 4-pentyl-4-methyl-4-phenyl-4-silacyclohexanone instead of 4-propyl-4-phenyl-4-silacyclohexanone, and 4-(trans-4-bromomethylcyclohexyl)-1-(1,2-difluorovinyl)benzene instead of 4-(trans-4-bromomethylcyclohexyl)-2,6-difluoro-1-(2,2-difluorovinyloxy)benzene, thereby obtaining the intended compound.

EXAMPLE 60

Preparation of 4-(trans-4-(2-(trans-4-n-propylcyclohexyl)ethyl)-4-silacyclohexyl)-2,6-difluoro-1-(1,2-difluorovinyl)benzene The general procedure of Example 54 was repeated using 4-propylcyclohexanone instead of 4-propyl-4-phenyl-4-silacyclohexanone, and 4-(trans-4-chloromethyl-4-silacyclohexyl)-2,6-difluoro-1-(1,2-difluorovinyl)benzene instead of 4-(trans-4-bromomethylcyclohexyl)-2,6-difluoro-1-(2,2-difluorovinyloxy)benzene, thereby obtaining the intended compound.

EXAMPLE 61

Preparation of 4-(trans-4-(2-(trans-4-n-pentylcyclohexyl)ethyl)-4-fluoro-4-silacyclohexyl)-1-(2,2-difluorovinyl)benzene In the following examples, the liquid crystal compositions of the invention are particularly described in which percent is by mole.

EXAMPLE 62

4-(trans-4-n-pentyl-4-silacyclohexyl)-1-(2,2-difluoro-1-ethenyl)benzene 5%

4-(trans-4-n-heptyl-4-silacyclohexyl)-1-(2,2-difluoro-1-ethenyl)benzene 5%

4-(trans-4-(trans-4-n-propyl-4-silacyclohexyl)cyclohexyl)-1-trifluoromethoxybenzene 20%

4-(trans-4-(trans-4-n-pentyl-4-silacyclohexyl)cyclohexyl)-1-trifluoromethoxybenzene 10%

4-(trans-4-(trans-4-n-propyl-4-silacyclohexyl)cyclohexyl)-1,2,6-trifluorobenzene 10%

4-(trans-4-(trans-4-n-pentyl-4-silacyclohexyl)cyclohexyl)-1,2,6-trifluorobenzene 5%

4-(trans-4-(trans-4-n-propyl-4-silacyclohexyl)cyclohexyl)-2,6-difluoro-1-(2,2-difluoro-1-ethenyloxy)benzene 6%

4-(trans-4-(trans-4-n-butyl-4-silacyclohexyl)cyclohexyl)-2,6-difluoro-1-(2,2-difluoro-1-ethenyloxy)benzene 9%

4-(trans-4-(trans-4-n-pentyl-4-silacyclohexyl)cyclohexyl)-2,6-difluoro-1-(2,2-difluoro-1-ethenyloxy)benzene 10%

4'-(trans-4-n-propyl-4-silacyclohexyl)-3-fluoro-4-difluoromethoxybiphenyl 5%

4'-(trans-4-n-pentyl-4-silacyclohexyl)-3-fluoro-4-difluoromethoxybiphenyl 5%

4'-(trans-4-n-propyl-4-silacyclohexyl)-2'-fluoro-4-trifluoromethoxybiphenyl 4%

4'-(trans-4-n-pentyl-4-silacyclohexyl)-2'-fluoro-4-trifluoromethoxybiphenyl 6%

EXAMPLE 63

4-(trans-4-n-pentyl-4-silacyclohexyl)-1-methoxybenzene 10%

4-(trans-4-(trans-4-n-propyl-4-silacyclohexyl)cyclohexyl)-1-trifluoromethoxybenzene 15%

4-(trans-4-(trans-4-n-pentyl-4-silacyclohexyl)cyclohexyl)-1-trifluoromethoxybenzene 10%

4-(trans-4-(trans-4-n-propyl-4-silacyclohexyl)cyclohexyl)-1,2,6-trifluorobenzene 10%

4-(trans-4-(trans-4-n-pentyl-4-silacyclohexyl)cyclohexyl)-1,2,6-trifluorobenzene 5%

4-(trans-4-(trans-4-n-propyl-4-silacyclohexyl)cyclohexyl)-2,6-difluoro-1-(1,2,2-trifluoro-1-ethenyloxy)benzene 13%

4-(trans-4-(trans-4-n-pentyl-4-silacyclohexyl)cyclohexyl)-2,6-difluoro-1-(1,2,2-trifluoro-1-ethenyloxy)benzene 12%

4-(trans-4-n-propyl-4-silacyclohexyl)-3,5-difluoro-4-(2,2-difluoroethoxy)biphenyl 5%

4'-(trans-4-n-pentyl-4-silacyclohexyl)-3,5-difluoro-4-(2,2-difluoroethoxy)biphenyl 5%

4'-(trans-4-n-propyl-4-silacyclohexyl)-3,5-difluoro-4-(2,2-difluoro-1-ethenyloxy)biphenyl 5%

4'-(trans-4-n-pentyl-4-silacyclohexyl)-3,5-difluoro-4-(2,2-difluoro-1-ethenyloxy)biphenyl 5% trans, trans-4'-(4-(4-n-propyl-4-silacyclohexyl)cyclohexyl)-3,4-difluorobiphenyl 3% trans, trans-4'-(4-(4-n-pentyl-4-silacyclohexyl)cyclohexyl)-3,4-difluorobiphenyl 2%

EXAMPLE 64

4-(trans-4-n-pentylcyclohexyl)-1-(1,2-difluoro-1-ethenyl)benzene 5%

4-(trans-4-n-heptylcyclohexyl)-1-(1,2-difluoro-1-ethenyl)benzene 5%

4-(trans-4-(trans-4-n-propylcyclohexyl)cyclohexyl)-1,2,6-trifluorobenzene 15%

4-(trans-4-(trans-4-n-pentylcyclohexyl)cyclohexyl)-1,2,6-trifluorobenzene 10%

4-(trans-4-(trans-4-n-propyl-4-silacyclohexyl)cyclohexyl)-2,6-difluoro-1-(2,2-difluoro-1-ethenyloxy)benzene 7%

4-(trans-4-(trans-4-n-butyl-4-silacyclohexyl)cyclohexyl)-2,6-difluoro-1-(2,2-difluoro-1-ethenyloxy)benzene 7%

4-(trans-4-(trans-4-n-pentyl-4-silacyclohexyl)cyclohexyl)-2,6-difluoro-1-(2,2-difluoro-1-ethenyloxy)benzene 6%

4-(trans-4-(trans-4-n-propyl-4-silacyclohexyl)cyclohexyl)-2,6-difluoro-1-(1,2,2-trifluoro-1-ethenyloxy)benzene 10%

4-(trans-4-(trans-4-n-pentyl-4-silacyclohexyl)cyclohexyl)-2,6-difluoro-1-(1,2,2-trifluoro-1-ethenyloxy)benzene 10%

4'-(trans-4-n-propylcyclohexyl)-2',6',3,5-tetrafluoro-4-(2,2-difluoro-1-ethenyloxy)biphenyl 10%

4'-(trans-4-n-pentylcyclohexyl)-2',6',3,5-tetrafluoro-4-(2,2-difluoro-1-ethenyloxy)biphenyl 15%

EXAMPLE 65

4-(trans-4-n-pentyl-4-silacyclohexyl)-1-(2,2-difluoro-1-ethenyl)benzene 5%

4-(trans-4-n-heptyl-4-silacyclohexyl)-1-(2,2-difluoro-1-ethenyl)benzene 5%

4-(trans-4-(trans-4-n-propyl-4-silacyclohexyl)cyclohexyl)-1-trifluoromethoxybenzene 10%

4-(trans-4-(trans-4-n-pentyl-4-silacyclohexyl)cyclohexyl)-1-trifluoromethoxybenzene 10%

4-(trans-4-(trans-4-n-propyl-4-silacyclohexyl)cyclohexyl)-1,2,6-trifluorobenzene 10%

4-(trans-4-(trans-4-n-pentyl-4-silacyclohexyl)cyclohexyl)-1,2,6-trifluorobenzene 10%

4'-(trans-4-n-propyl-4-silacyclohexyl)-2',3,5-trifluoro-4-(2,2-difluoroethoxy)biphenyl 10%

4'-(trans-4-n-pentyl-4-silacyclohexyl)-2',3,5-trifluoro-4-(2,2-difluoroethoxy)biphenyl 10%

4-(trans-4-(trans-4-n-propylcyclohexyl)cyclohexyl)-2,6-difluoro-1-(1,2,2-trifluoro-1-ethenyl)benzene 12%

4-(trans-4-(trans-4-n-pentylcyclohexyl)cyclohexyl)-2,6-difluoro-1-(1,2,2-trifluoro-1-ethenyl)benzene 12%

4,4'-bis-(trans-4-(trans-4-n-propylcyclohexyl)-2-fluorobiphenyl 2%

4-(trans-4-(n-pentylcyclohexyl)-4'-(trans-4-n-propylcyclohexyl)-2-fluorobiphenyl 2%

4,4'-bis-(trans-4-n-pentylcyclohexyl)-2-fluorobiphenyl 2[[]ps

What is claimed is:

1. A silacyclohexane compound of the following general formula ($I_1$)

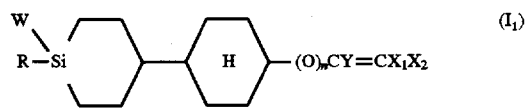

wherein R represents a linear alkyl group having from 1 to 10 carbon atoms, a branched alkyl group having from 3 to 8 carbon atoms, an alkoxyalkyl group having from 2 to 7 carbon atoms, an alkenyl group having from 2 to 8 carbon atoms, or a mono or difluoroalkyl group having from 1 to 10 carbon atoms, W represents H, F, Cl or $CH_3$, n is 0 or 1, $X_1$ and Y independently represent H, F or Cl, and $X_2$ represents F or Cl.

2. A silacyclohexane compound of the following general formula ($I_3$)

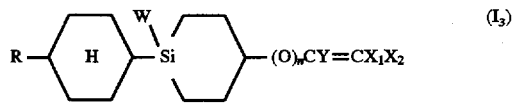

wherein R represents a linear alkyl group having from 1 to 10 carbon atoms, a branched alkyl group having from 3 to 8 carbon atoms, an alkoxyalkyl group having from 2 to 7 carbon atoms, an alkenyl group having from 2 to 8 carbon atoms, or a mono or difluoroalkyl group having from 1 to 10 carbon atoms, W represents H, F, Cl or $CH_3$, n is 0 or 1 $X_1$ and Y independently represent H, F or Cl, and $X_2$ represents F or Cl.

3. A silacyclohexane compound of the following general formula ($I_4$)

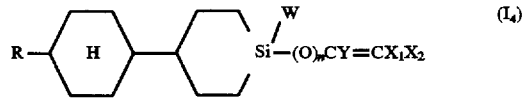

wherein R represents a linear alkyl group having from 1 to 10 carbon atoms, a branched alkyl group having from 3 to 8 carbon atoms, an alkoxyalkyl group having 2 to 7 carbon atoms, an alkenyl group having from 2 to 8 carbon atoms, or a mono or difluoroalkyl group having from 1 to 10 carbon atoms, W represents H, F, Cl or $CH_3$, n is 0 or 1, $X_1$ and Y independently represent H, F, or Cl, and $X_2$ represents F or Cl.

4. A silacyclohexane compound of the following general formula ($I_5$)

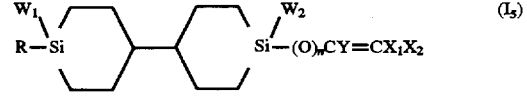

wherein R represents a linear alkyl group having from 1 to 10 carbon atoms, a branched alkyl group having from 3 to 8 carbon atoms, an alkoxyalkyl group having from 2 to 7 carbon atoms, an alkenyl group having from 2 to 8 carbon atoms, or a mono or difluoroalkyl group having from 1 to 10 carbon atoms, $W_1$ and $W_2$ independently represent H, F, Cl or $CH_3$, n is 0 or 1, $X_1$ and Y independently represent H, F or Cl, and $X_2$ represents F or Cl.

5. A silacyclohexane compound of the following general formula ($I_6$)

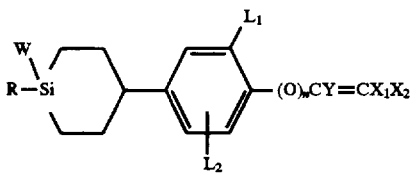

($I_6$)

wherein R represents a linear alkyl group having from 1 to 10 carbon atoms, a branched alkyl group having from 3 to 8 carbon atoms, an alkoxyalkyl group having from 2 to 7 carbon atoms, an alkenyl group having from 2 to 8 carbon atoms, or a mono or difluoroalkyl group having from 1 to 10 carbon atoms, W represents H, F, Cl or $CH_3$, $L_1$ and $L_2$ independently represent H or F, n is 0 or 1, $X_1$ and Y independently represent H, F or Cl, and $X_2$ represents F or Cl.

6. A silacyclohexane compound of the following general formula ($I_{10}$)

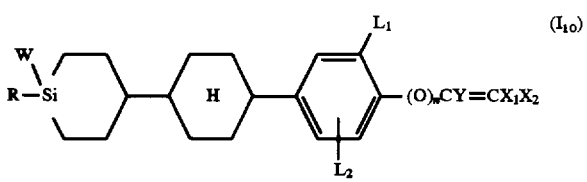

($I_{10}$)

wherein R represents a linear alkyl group having from 1 to 10 carbon atoms, a branched alkyl group having from 3 to 8 carbon atoms, an alkoxyalkyl group having from 2 to 7 carbon atoms, an alkenyl group having from 2 to 8 carbon atoms, or a mono or difluoroalkyl group having from 1 to 10 carbon atoms, W represents H, F, Cl or $CH_3$, $L_1$ and $L_2$ independently represent H or F, n is 0 or 1, $X_1$ and Y independently represent H, F or Cl, and $X_2$ represents F and Cl.

7. A silacyclohexane compound of the following general formula ($I_{12}$)

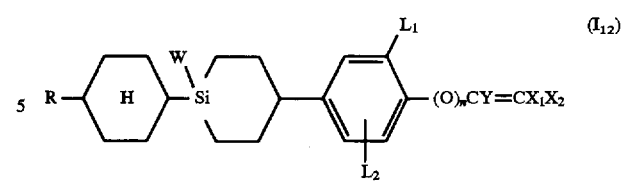

($I_{12}$)

wherein R represents a linear alkyl group having from 1 to 10 carbon atoms, a branched alkyl group having from 3 to 8 carbon atoms, an alkoxyalkyl group having from 2 to 7 carbon atoms, an alkenyl group having from 2 to 8 carbon atoms, or a mono or difluoroalkyl group having from 1 to 10 carbon atoms, W represents H, F, Cl or $CH_3$, $L_1$ and $L_2$ independently represent H or F, n is 0 or 1, $X_1$ and Y independently represent H, F or Cl, and $X_2$ represents F or Cl.

8. A silacyclohexane compound of the following general formula ($I_{15}$)

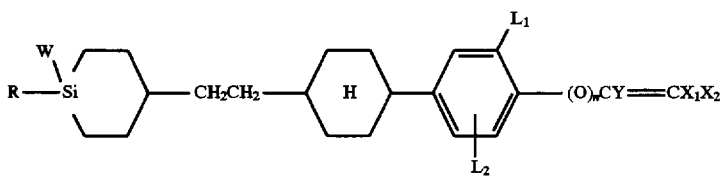

($I_{15}$)

wherein R represents a linear alkyl group having from 1 to 10 carbon atoms, a branched alkyl group having from 3 to 8 carbon atoms, an alkoyalkyl group having from 2 to 7 carbon atoms, an alkenyl group having from 2 to 8 carbon atoms, or a mono or difluoroalkyl group having from 1 to 10 carbon atoms, W represents E, F, Cl or $CH_3$, $L_1$ and $L_2$ independently represent H or F, n is 0 or 1, $X_1$ and Y independently represent H, F or Cl, and $X_2$ represents F or Cl.

9. A silicylohexane compound of the following general formula ($I_{17}$)

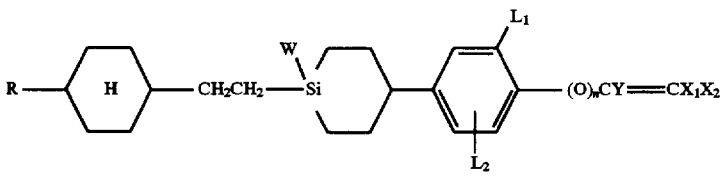

($I_{17}$)

wherein R represents a linear alkyl group having from 1 to 10 carbon atoms, a branched alkyl group having from 3 to 8 carbon atoms, an alkoxyalkyl group having from 2 to 7 carbon atoms, an alkenyl group having from 2 to 8 carbon atoms, or a mono or difluoroalkyl group having from 1 to 10 carbon atoms, W represents H, F, Cl or $CH_3$, $L_1$ and $L_2$ independently represent H or F, n is 0 or 1, $X_1$ and Y independently represent H, F or Cl, and $X_2$ represents F or Cl.

10. A silacyclohexane compound of the following general formula ($I_{20}$)

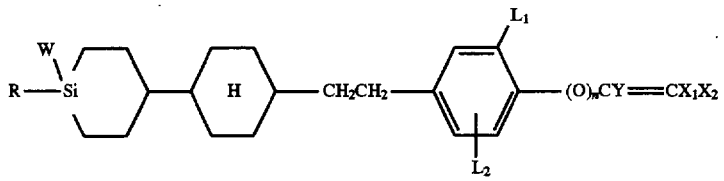

(I₂₀)

wherein R represents a linear alkyl group having from 1 to 10 carbon atoms, a branched alkyl group having from 3 to 8 carbon atoms, an alkoxyalkyl group having from 2 to 7 carbon atoms, an alkenyl group having from 2 to 8 carbon atoms, or a mono or difluoroalkyl group having from 1 to 10 carbon atoms, W represents H, F, Cl or $CH_3$, $L_1$ and $L_2$ independently represent H or F, n is 0 or 1, $X_1$ and Y independently represent H, F or Cl, and $X_2$ represents F or Cl.

11. A silacyclohexane compound of the following general formula (I₂₂)

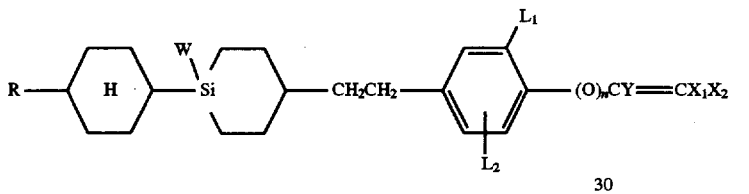

(I₂₂)

wherein R represents a linear alkyl group having from 1 to 10 carbon atoms, a branched alkyl group having from 3 to 8 carbon atoms, an alkoxyalkyl group having from 2 to 7 carbon atoms, an alkenyl group having from 2 to 8 carbon atoms, or a mono or difluoroalkyl group having from 1 to 10 carbon atoms, W represents H, F, Cl or $CH_3$, $L_1$ and $L_2$ independently represent H or F, n is 0 or 1, $X_1$ and Y independently represent H, F or Cl, and $X_2$ represents F or Cl.

12. A silacyclohexane compound of the following general formula (I₂₅)

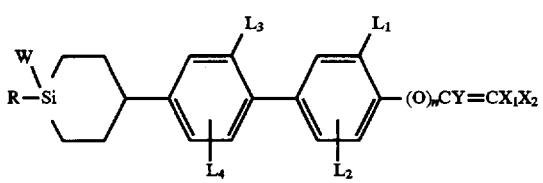

(I₂₅)

wherein R represents a linear alkyl group having from 1 to 10 carbon atoms, a branched alkyl group having from 3 to 8 carbon atoms, an alkoxyalkyl group having from 2 to 7 carbon atoms, an alkenyl group having from 2 to 8 carbon atoms, or a mono or difluoroalkyl group having from 1 to 10 carbon atoms, W represents H, F, Cl or $CH_3$, $L_1$, $L_2$, $L_3$ and $L_4$ independently represent H or F, n is 0 or 1, $X_1$ and Y independently represent H, F or Cl, and $X_2$ represents F or Cl.

13. A silacyclohexane compound of the following general formula (I₂₉)

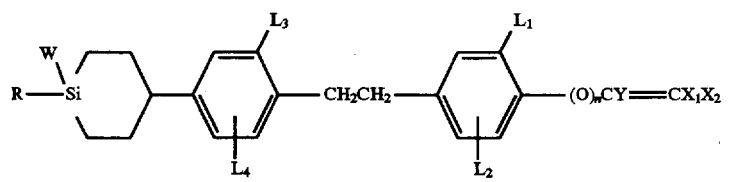

(I₂₉)

wherein R represents a linear alkyl group having from 1 to 10 carbon atoms, a branched alkyl group having from 3 to 8 carbon atoms, an alkoxyalkyl group having from 2 to 7 carbon atoms, an alkenyl group having from 2 to 8 carbon atoms, or a mono or difluoroalkyl group having from 1 to 10 carbon atoms, W represents E, F, Cl or $CH_3$, $L_1$, $L_2$, $L_3$ and $L_4$ independently represent H or F, n is 0 or 1, $X_1$ and Y independently represent H, F or Cl, and $X_2$ represents F or Cl.

14. A liquid crystal composition which comprises the silacyclohexane compound defined in any one of claims 1 to 13.

15. A liquid crystal device which comprises the liquid crystal composition defined in claim 14.

16. A liquid crystal composition which comprises at least one compound selected from the group consisting of silacyclohexane compounds of the following formulas:

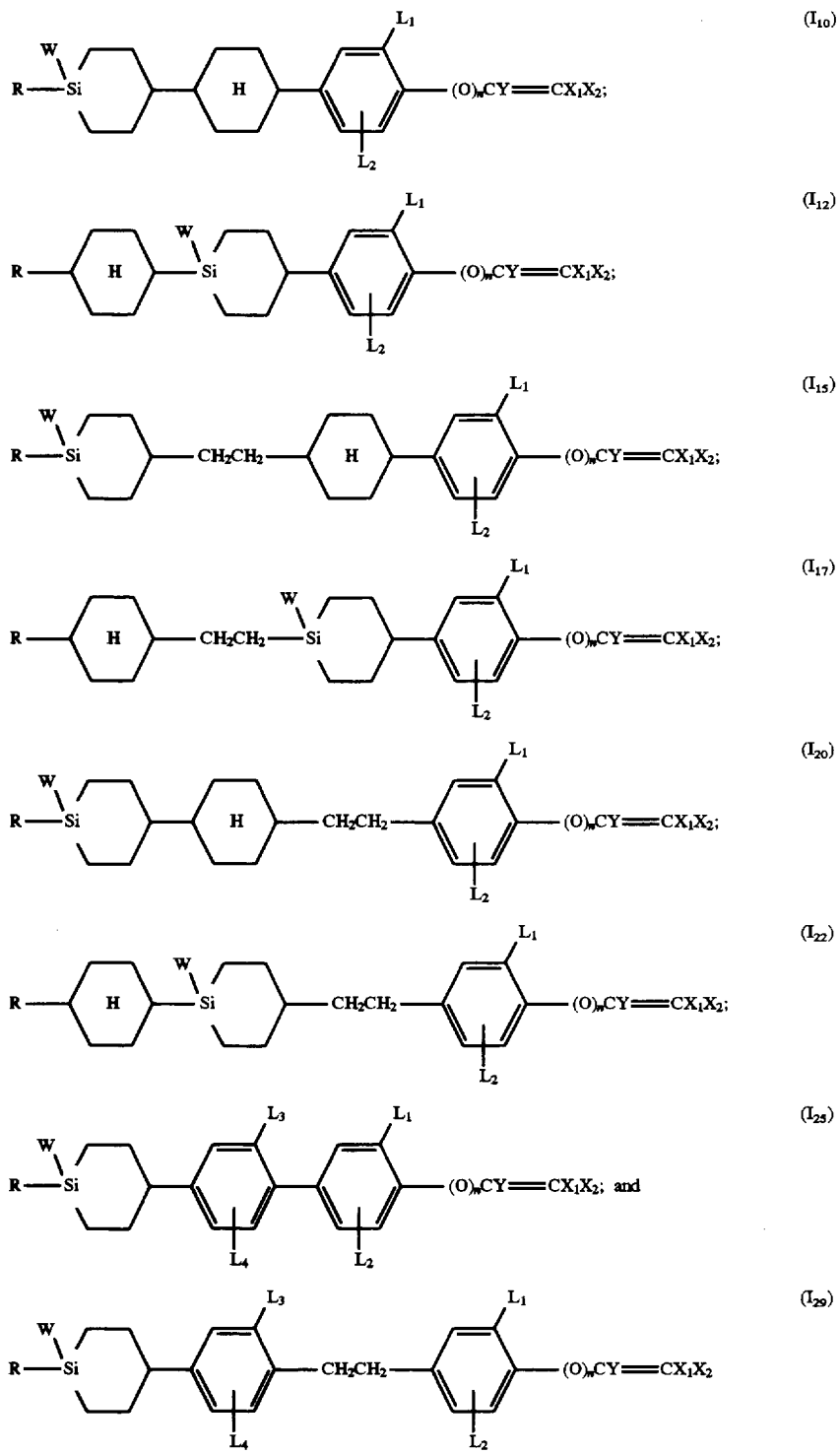

wherein R represents a linear alkyl group having from 1 to 10 carbon atoms, a branched alkyl group having from 3 to 8 carbon atoms, an alkoxyalkyl group having from 2 to 7 carbon atoms, an alkenyl group having from 2 to 8 carbon atoms, or a mono or difluoroalkyl group having from 1 to 10 carbon atoms, W, $W_1$ and $W_2$ independently represent H, F, Cl or $CH_3$, $L_1$, $L_2$, $L_3$ and $L_4$ independently represent H or F, n is 0 or 1, $X_1$ and Y independently represent H, F or Cl, and $X_2$ represents F or Cl.

17. A liquid crystal device which comprises the composition defined in claim 16.

18. A liquid crystal composition which comprises a mixture of at least one silacyclohexane compounds of the formulas ($I_{10}$), ($I_{12}$), ($I_{15}$), ($I_{17}$), ($I_{20}$), ($I_{22}$), ($I_{25}$) and ($I_{29}$) defined in claim 44 and at least one compound selected from the group consisting of compounds of the formulas (IIId) to (IIIh), (IVd) to (IVh), (Va) to (Ve) and (VIa) to (VIc)

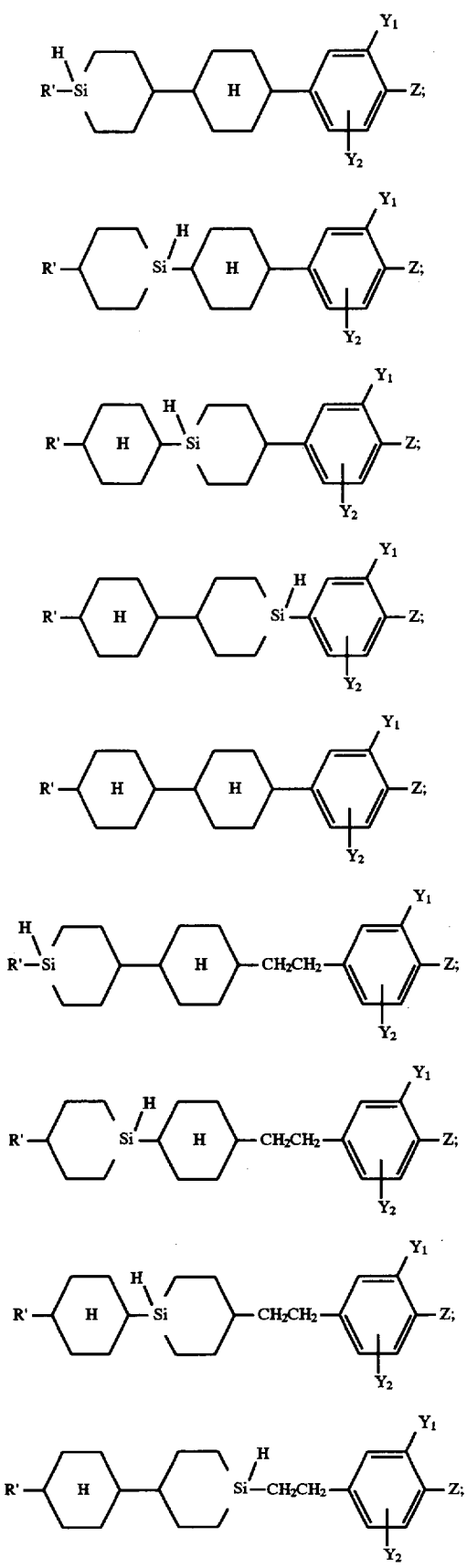
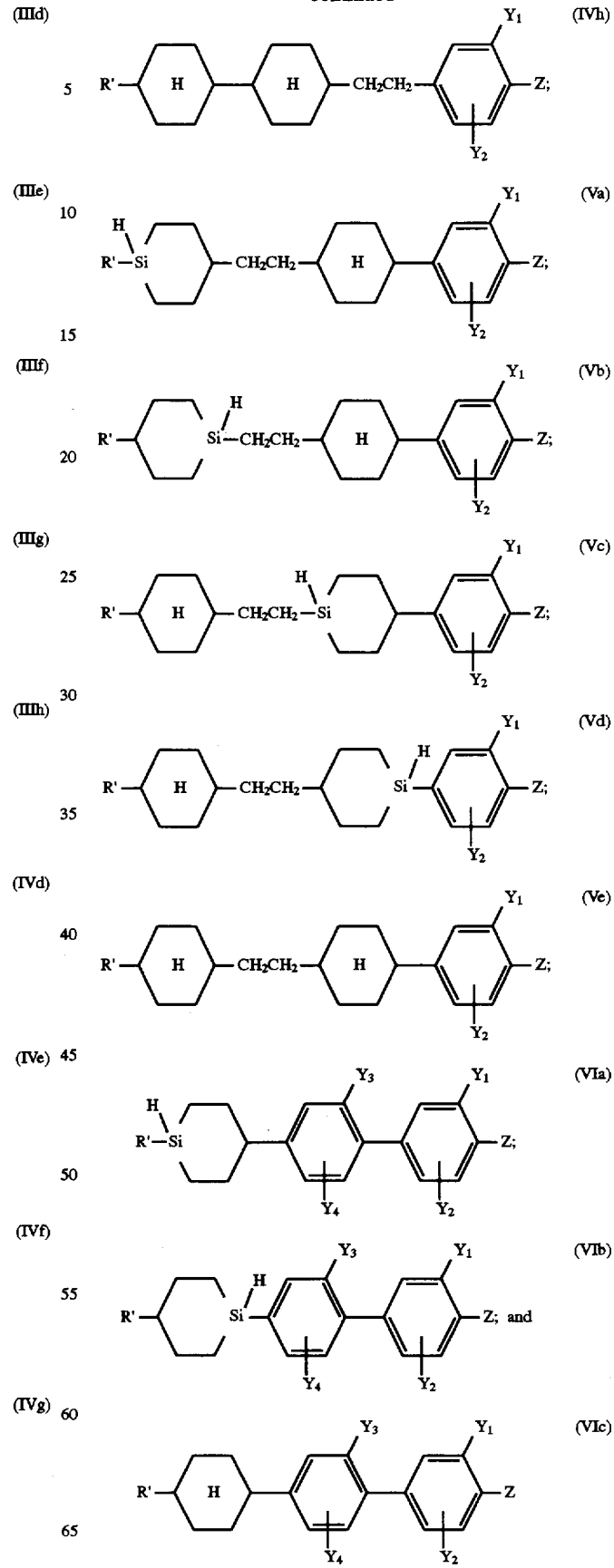

wherein R' represents a linear alkyl group having from 1 to 7 carbon atoms, an alkoxyalkyl group having from 2 to 7 carbon atoms, a mono or difluoroalkyl group having from 2 to 7 carbon atoms, and an alkenyl group having from 2 to 8 carbon atoms, Z represents F, Cl, OCHF$_2$, OCF$_3$, O(CH$_2$)$_p$(CF$_2$)$_q$M, in which p and q are each 0, 1 or 2, provided that (p+q)=2, 3 or 4, and M represents H, F or Cl, CF$_3$ or alkoxy group having up to 5 carbon atoms, and Y$_1$, Y$_2$, Y$_3$ and Y$_4$ independently represent H or F.

19. A liquid crystal display device comprising the composition defined in claim 18.

20. A liquid crystal composition according to claim 18, wherein said at least one silacyclohexane compound is present in an amount of from 20 to 90 mole %.

21. A liquid crystal composition according to claim 18, further comprising up to 30 mole % of at least one compound selected from those compounds of general formulas (I$_1$), (I$_4$), (I$_5$), (I$_6$), (IIa) to (IIe), (IIIa) to (IIIc) and (IVa) to (IVc):

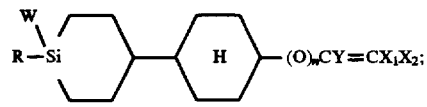   (I$_1$)

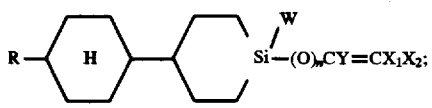   (I$_4$)

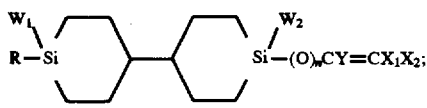   (I$_5$)

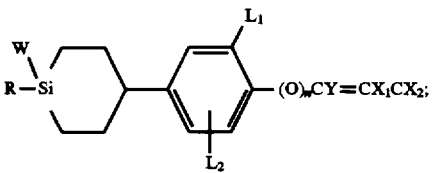   (I$_6$)

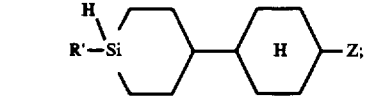   (IIa)

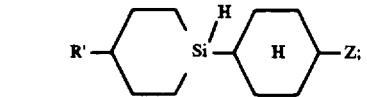   (IIb)

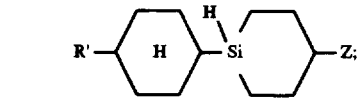   (IIc)

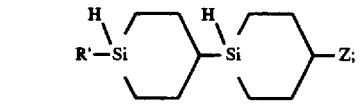   (IId)

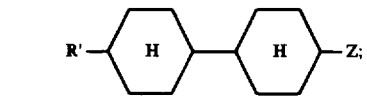   (IIe)

-continued

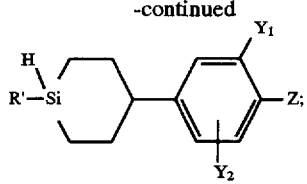   (IIIa)

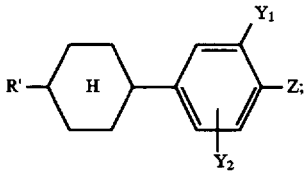   (IIIc)

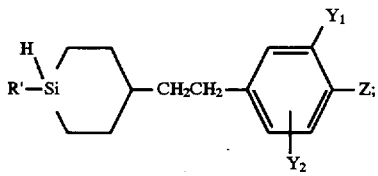   (IVa)

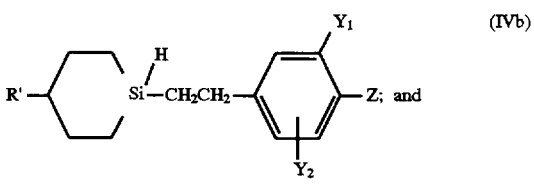   (IVb)

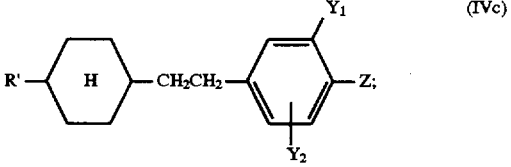   (IVc)

wherein R represents a linear alkyl group having from 1 to 10 carbon atoms, a branched alkyl group having from 3 to 8 carbon atoms, an alkoxyalkyl group having from 2 to 7 carbon atoms, an alkenyl group having from 2 to 8 carbon atoms, or a mono or difluoroalkyl group having from 1 to 10 carbon atoms, W, W$_1$ and W$_2$ independently represent H, F, Cl or CH$_3$, L$_1$ and L$_2$ independently represent H or F, n is 0 or 1, X$_1$ and Y independently represent H, F or Cl, and X$_2$ represents F or Cl, and R', Z, Y$_1$, Y$_2$, Y$_3$ and Y$_4$ are each as defined in claim 18, with the balance being said mixture.

22. A liquid crystal display device comprising the composition of claim 21.

23. A liquid crystal composition according to claim 21, further comprising up to 20 mole % of at least one compound selected from those compounds of the general formulas (VIIa) to (VIIf) and (VIIIa) to (VIIIl)

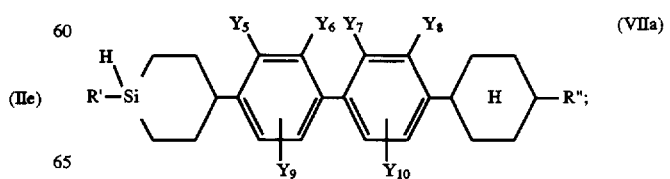   (VIIa)

-continued
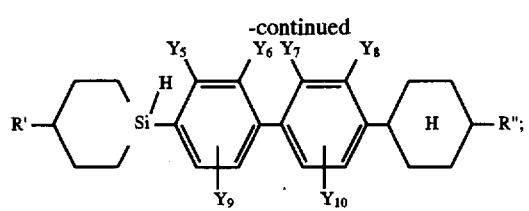 (VIIb)
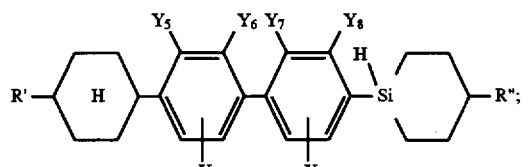 (VIIc)
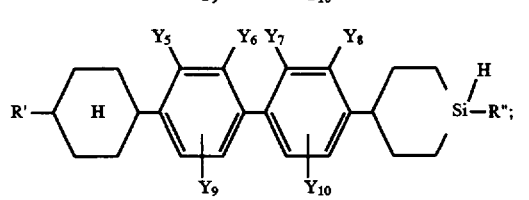 (VIId)
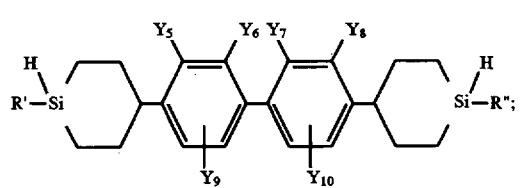 (VIIe)
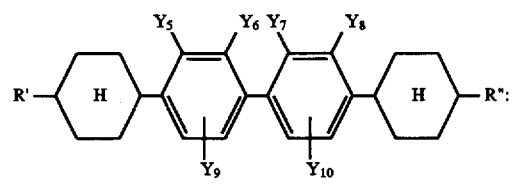 (VIIf)
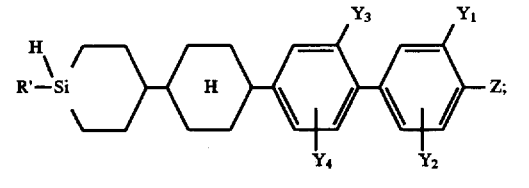 (VIIIa)
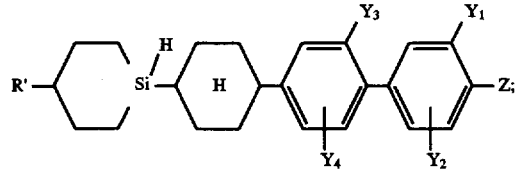 (VIIIb)
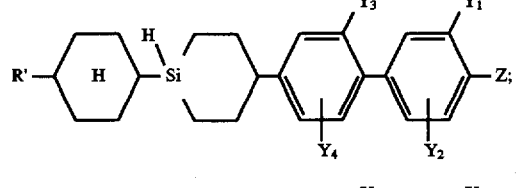 (VIIIc)
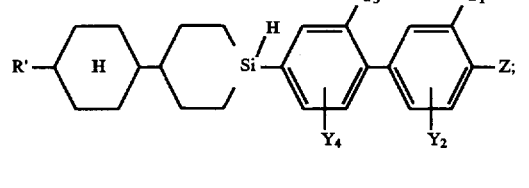 (VIIId)
-continued
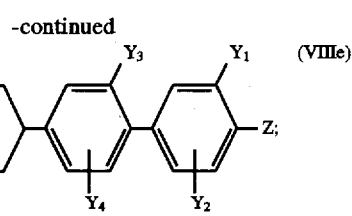 (VIIIe)
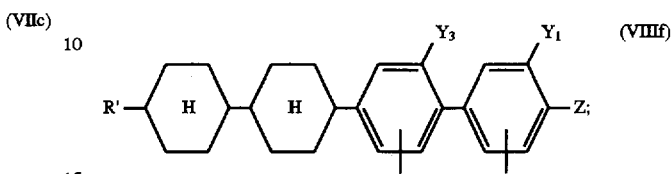 (VIIIf)
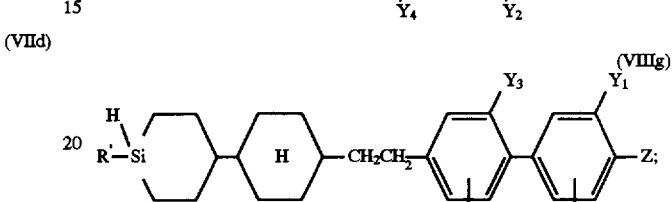 (VIIIg)
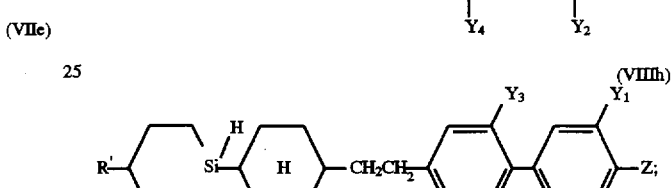 (VIIIh)
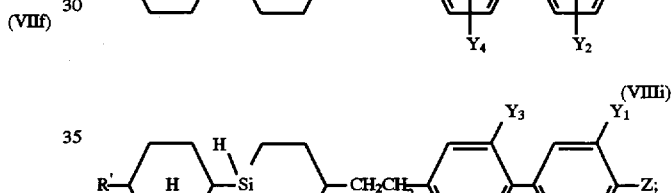 (VIIIi)
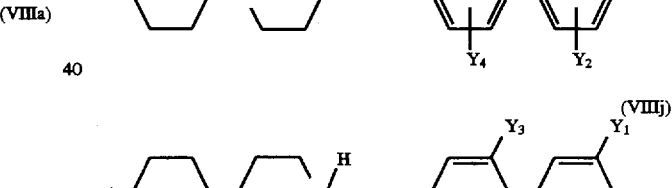 (VIIIj)
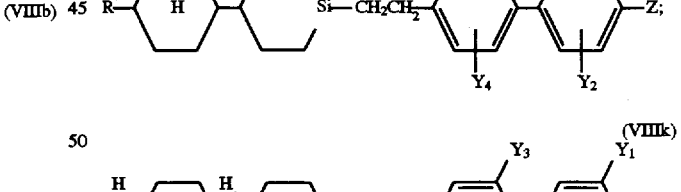 (VIIIk)
and
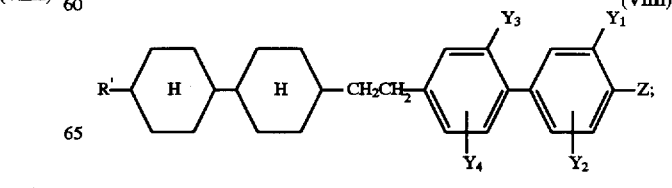 (VIIIl)

wherein R' and R" independently represent an alkyl group from having from 1 to 7, and alkoxyalkyl group, a mono or difluoroalkyl group or an alkenyl group each having from 2 to 7 carbon atoms, Z represents F, Cl, OCHF$_2$, OCF$_3$, O(CH$_2$)$_p$(CF$_2$)$_q$M in which p and q are each 0, 1 or 2 provided that (p+q)=2, 3 or 4, and M represents H, F or Cl, CF$_3$ or an alkoxy group having up to 5 carbon atoms, and Y$_1$ to Y$_{10}$ each represent H or F.

24. A liquid crystal display device comprising the composition of claim 23.

25. A liquid crystal composition according to claim 18, further comprising up to 20 mole % of at least one compound selected from those compounds of the general formulas (VIIa) to (VIIf) and (VIIIa) to (VIIIl)

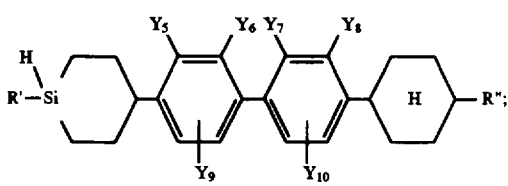
(VIIa)

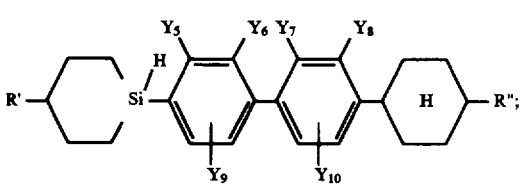
(VIIb)

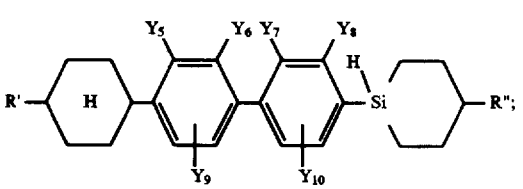
(VIIc)

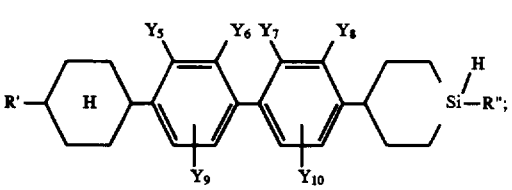
(VIId)

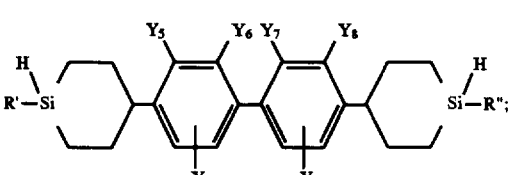
(VIIe)

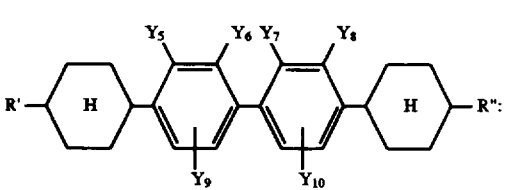
(VIIf)

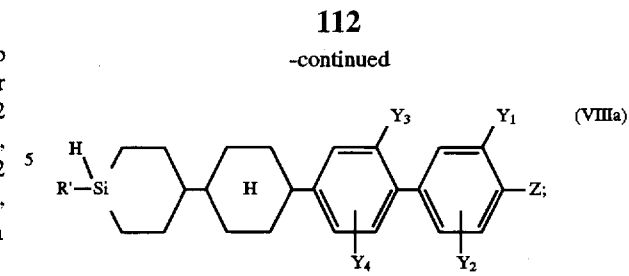
(VIIIa)

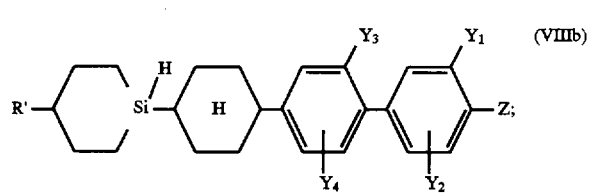
(VIIIb)

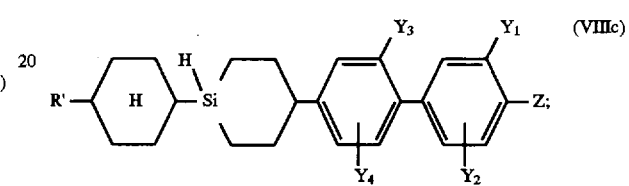
(VIIIc)

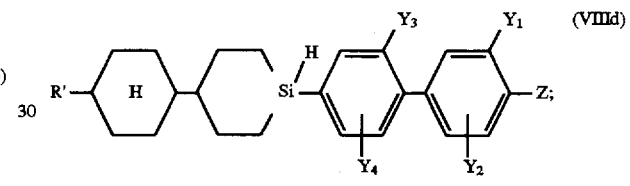
(VIIId)

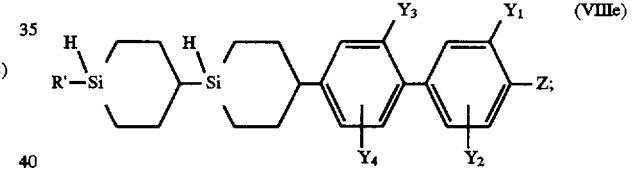
(VIIIe)

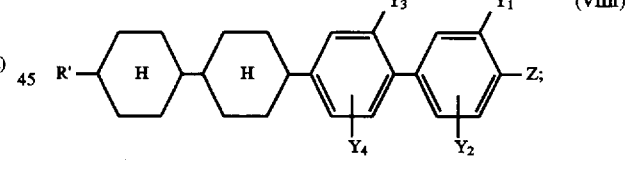
(VIIIf)

(VIIIg)

(VIIIh)

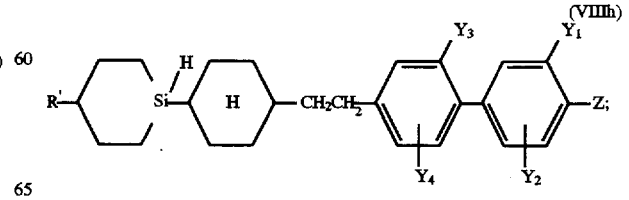

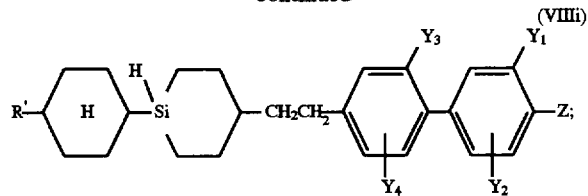
(VIIIi)

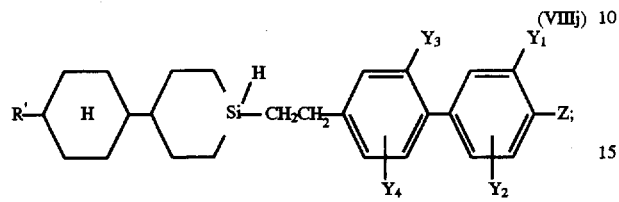
(VIIIj)

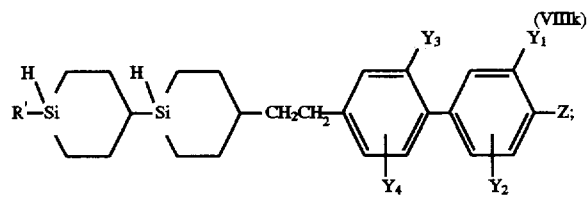
(VIIIk)

and

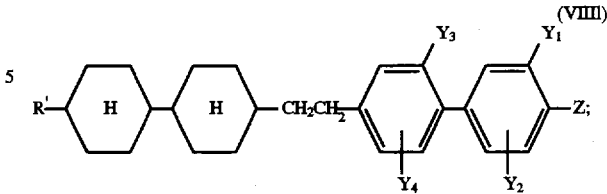
(VIIII)

wherein R' and R" independently represent an alkyl group having from 1 to 7, and an alkoxyalkyl group, a mono or difluoroalkyl group or an alkenyl group each having from 2 to 7 carbon atoms, Z represents F, Cl, OCHF$_2$, OCF$_3$, O(CH$_2$)$_p$(CF$_2$)$_q$M, in which p and q are each 0, 1 or 2 provided that (p+q)=2, 3 or 4, and M represents H F or Cl, CF$_3$ or an alkoxy group having up to 5 carbon atoms, and Y$_1$ to Y$_{10}$ independently represent H or F.

26. A liquid crystal display device comprising the composition of claim 25.

* * * * *